(12) United States Patent
Krag et al.

(10) Patent No.: US 8,452,375 B2
(45) Date of Patent: May 28, 2013

(54) SYSTEMS AND METHODS FOR LOCATING AND DEFINING A TARGET LOCATION WITHIN A HUMAN BODY

(75) Inventors: David Krag, Shelbume, VT (US); Eric Meier, Bellevue, WA (US); Steve Dimmer, Bellevue, WA (US); Duane Durbin, San Diego, CA (US); Trevor Moody, Seattle, WA (US); Fred Silverstein, Seattle, WA (US); Rosemary Harry, Seattle, WA (US); Richard Frecksa, Seattle, WA (US); Amy Kinsella, Seattle, WA (US); Jon Gilbert, Seattle, WA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 10/745,104

(22) Filed: Dec. 23, 2003

(65) Prior Publication Data
US 2004/0138555 A1 Jul. 15, 2004

Related U.S. Application Data

(63) Continuation of application No. 10/438,500, filed on May 14, 2003, which is a continuation of application No. PCT/US00/31667, filed on Nov. 17, 2000, and a continuation-in-part of application No. 09/078,982, filed on May 14, 1998, now Pat. No. 6,363,940.

(51) Int. Cl.
*A61B 5/055* (2006.01)
*A61B 19/00* (2006.01)

(52) U.S. Cl.
USPC .......................................... 600/424; 128/899

(58) Field of Classification Search
USPC ...... 600/421, 422, 426, 302; 128/899; 378/65; 324/260
See application file for complete search history.

(56) References Cited

U.S. PATENT DOCUMENTS

| 3,577,160 A | 5/1971 | White |
| 3,752,960 A | 8/1973 | Walton |

(Continued)

FOREIGN PATENT DOCUMENTS

| DE | 19914455 A1 | 10/2000 |
| EP | 0531081 A1 | 1/1992 |

(Continued)

OTHER PUBLICATIONS

U.S. Appl. No. 10/416,827, filed Nov. 17, 2000, David Krag.

(Continued)

*Primary Examiner* — Michael Rozanski
(74) *Attorney, Agent, or Firm* — Perkins Coie LLP

(57) ABSTRACT

Systems and methods for locating and defining a target location within a human body. The system can include at least one marker, a probe, and a detector for use in locating the markers by providing information to a surgeon that is representative of changes in proximity between the probe and the marker. The marker can have various detection characteristics, e.g., gamma radiation, that are detectable by an associated probe and detector. The tissue volume is removed by manipulating a cutting tool based on the proximity information provided by the detector, which can be used by the surgeon to define the boundary of the tissue volume. The systems and methods of the invention are particularly useful in locating and then removing a tissue volume or other target location from amorphous, pliable tissue (e.g., breast tissue) or other body parts.

19 Claims, 28 Drawing Sheets

U.S. PATENT DOCUMENTS

| | | |
|---|---|---|
| 3,794,840 A | 2/1974 | Scott |
| 3,836,842 A | 9/1974 | Zimmermann et al. |
| 3,967,161 A | 6/1976 | Lichtblau |
| 3,969,629 A | 7/1976 | McIntyre |
| 4,017,858 A | 4/1977 | Kuipers |
| 4,023,167 A | 5/1977 | Wahlstrom |
| 4,065,753 A | 12/1977 | Paul, Jr. |
| 4,114,601 A | 9/1978 | Abels |
| 4,123,749 A | 10/1978 | Hartmann et al. |
| 4,127,110 A | 11/1978 | Bullara |
| 4,160,971 A | 7/1979 | Jones et al. |
| 4,222,374 A | 9/1980 | Sampson |
| 4,230,123 A | 10/1980 | Hawkins |
| 4,260,990 A | 4/1981 | Lichtblau |
| 4,393,872 A | 7/1983 | Reznik et al. |
| 4,395,910 A | 8/1983 | Thomenius |
| 4,466,075 A | 8/1984 | Groch |
| 4,618,822 A * | 10/1986 | Hansen .................... 324/207.16 |
| 4,618,978 A | 10/1986 | Cosman |
| 4,633,250 A | 12/1986 | Anderson |
| 4,636,380 A | 1/1987 | Wong |
| 4,642,786 A | 2/1987 | Hansen |
| 4,643,196 A | 2/1987 | Tanaka |
| 4,696,287 A * | 9/1987 | Hortmann et al. .............. 607/57 |
| 4,737,794 A | 4/1988 | Jones |
| 4,755,680 A | 7/1988 | Logan |
| 4,795,995 A | 1/1989 | Eccleston |
| 4,799,495 A | 1/1989 | Hawkins |
| 4,832,055 A | 5/1989 | Palestrant |
| 4,849,692 A | 7/1989 | Blood |
| 4,909,789 A | 3/1990 | Taguchi |
| 4,936,823 A | 6/1990 | Colvin |
| 4,945,305 A | 7/1990 | Blood |
| 4,992,794 A | 2/1991 | Brouwers |
| 4,994,079 A | 2/1991 | Genese |
| 5,019,713 A | 5/1991 | Schmidt et al. |
| 5,031,634 A | 7/1991 | Simon |
| 5,050,608 A | 9/1991 | Watanabe |
| 5,057,095 A * | 10/1991 | Fabian .......................... 604/362 |
| 5,062,847 A | 11/1991 | Barnes |
| 5,073,781 A | 12/1991 | Stickelbrocks |
| 5,095,224 A | 3/1992 | Renger |
| 5,099,845 A | 3/1992 | Besz |
| 5,107,862 A | 4/1992 | Fabian |
| 5,142,292 A | 8/1992 | Chang |
| 5,170,055 A | 12/1992 | Carroll |
| 5,188,368 A | 2/1993 | Ryan |
| 5,189,690 A | 2/1993 | Samuel |
| 5,193,539 A * | 3/1993 | Schulman et al. .............. 607/61 |
| 5,197,466 A | 3/1993 | Marchosky |
| 5,198,877 A | 3/1993 | Schulz |
| 5,205,289 A | 4/1993 | Hardy |
| 5,207,223 A | 5/1993 | Adler |
| 5,211,129 A | 5/1993 | Taylor |
| 5,211,164 A | 5/1993 | Allen |
| 5,221,269 A | 6/1993 | Miller |
| 5,223,851 A | 6/1993 | Hadden |
| 5,230,338 A | 7/1993 | Allen |
| 5,233,990 A | 8/1993 | Barnea |
| 5,240,011 A | 8/1993 | Assa |
| 5,246,005 A | 9/1993 | Carroll |
| 5,262,772 A | 11/1993 | Urbas |
| 5,285,772 A | 2/1994 | Rattner et al. |
| 5,325,873 A | 7/1994 | Hirschi |
| 5,342,283 A | 8/1994 | Good |
| 5,353,804 A | 10/1994 | Kornberg et al. |
| 5,358,514 A * | 10/1994 | Schulman et al. .............. 607/61 |
| 5,377,678 A | 1/1995 | Dumoulin |
| 5,386,191 A | 1/1995 | McCarten et al. |
| 5,396,889 A | 3/1995 | Ueda et al. |
| 5,396,905 A | 3/1995 | Newman et al. |
| 5,397,329 A | 3/1995 | Allen |
| 5,400,787 A | 3/1995 | Marandos |
| 5,409,004 A | 4/1995 | Sloan |
| 5,411,026 A | 5/1995 | Carol |
| 5,417,210 A | 5/1995 | Funda |
| 5,423,334 A * | 6/1995 | Jordan ........................... 128/899 |
| 5,425,367 A * | 6/1995 | Shapiro et al. ................. 600/424 |
| 5,425,382 A | 6/1995 | Golden |
| 5,446,548 A | 8/1995 | Gerig |
| 5,453,686 A | 9/1995 | Anderson |
| 5,509,900 A | 4/1996 | Kirkman |
| 5,515,853 A | 5/1996 | Smith |
| 5,526,812 A | 6/1996 | Dumoulin |
| 5,528,651 A | 6/1996 | Leksell |
| 5,546,951 A | 8/1996 | Ben-Haim |
| 5,558,091 A | 9/1996 | Acker |
| 5,559,435 A | 9/1996 | Harada |
| 5,568,809 A | 10/1996 | Ben-haim |
| 5,572,999 A | 11/1996 | Funda |
| 5,617,857 A | 4/1997 | Chader |
| 5,621,779 A | 4/1997 | Hughes et al. |
| 5,622,170 A | 4/1997 | Schulz |
| 5,622,187 A | 4/1997 | Carol |
| 5,629,967 A | 5/1997 | Leksell |
| 5,630,431 A | 5/1997 | Taylor |
| 5,636,255 A | 6/1997 | Ellis et al. |
| 5,638,819 A | 6/1997 | Manwaring et al. |
| 5,645,065 A | 7/1997 | Shapiro |
| 5,680,106 A | 10/1997 | Schrott |
| 5,681,326 A | 10/1997 | Lax |
| 5,697,384 A | 12/1997 | Miyawaki |
| 5,707,362 A | 1/1998 | Yoon |
| 5,707,390 A | 1/1998 | Bonutti |
| 5,724,030 A | 3/1998 | Urbas et al. |
| 5,727,552 A | 3/1998 | Ryan |
| 5,735,795 A * | 4/1998 | Young et al. .................. 600/410 |
| 5,745,545 A | 4/1998 | Hughes |
| 5,749,887 A | 5/1998 | Heske et al. |
| RE35,816 E | 6/1998 | Schulz |
| 5,764,052 A | 6/1998 | Renger |
| 5,769,861 A | 6/1998 | Vilsmeier |
| 5,779,638 A | 7/1998 | Vesely |
| 5,782,775 A | 7/1998 | Milliman |
| 5,797,849 A | 8/1998 | Vesely |
| 5,805,661 A | 9/1998 | Leksell |
| 5,810,851 A * | 9/1998 | Yoon ............................. 606/148 |
| 5,813,985 A | 9/1998 | Carroll |
| 5,815,076 A | 9/1998 | Herring |
| 5,817,022 A | 10/1998 | Vesely |
| 5,817,092 A | 10/1998 | Behl |
| 5,820,553 A | 10/1998 | Hughes |
| 5,823,192 A | 10/1998 | Kalend |
| 5,828,770 A | 10/1998 | Leis |
| 5,830,144 A | 11/1998 | Vesely |
| 5,840,148 A * | 11/1998 | Campbell et al. .......... 156/275.5 |
| 5,868,673 A | 2/1999 | Vesely |
| 5,868,675 A | 2/1999 | Henrion |
| 5,879,297 A | 3/1999 | Haynor |
| 5,879,357 A | 3/1999 | Heaton |
| 5,895,235 A | 4/1999 | Droz |
| 5,902,238 A | 5/1999 | Golden |
| 5,902,310 A | 5/1999 | Foerster |
| 5,907,395 A | 5/1999 | Schulz |
| 5,910,144 A | 6/1999 | Hayashi |
| 5,913,820 A | 6/1999 | Bladen et al. |
| 5,923,417 A | 7/1999 | Leis |
| 5,928,137 A | 7/1999 | Green |
| 5,951,481 A | 9/1999 | Evans |
| 5,963,132 A | 10/1999 | Yoakum |
| 5,964,223 A * | 10/1999 | Baran ....................... 128/207.14 |
| 5,987,349 A | 11/1999 | Schulz |
| 5,989,265 A | 11/1999 | Bouquet De La Joliniere |
| 6,015,390 A | 1/2000 | Krag |
| 6,019,725 A | 2/2000 | Vesely |
| 6,026,818 A * | 2/2000 | Blair et al. ..................... 128/899 |
| 6,033,721 A | 3/2000 | Nassuphis |
| 6,049,587 A | 4/2000 | Leksell |
| 6,052,477 A | 4/2000 | Wang |
| 6,059,734 A | 5/2000 | Yoon |
| 6,061,644 A | 5/2000 | Leis |
| 6,064,904 A | 5/2000 | Yanof |
| 6,067,465 A | 5/2000 | Foo |
| 6,076,008 A | 6/2000 | Bucholz |
| 6,082,366 A | 7/2000 | Andra |
| 6,094,007 A | 7/2000 | Faul |
| 6,097,007 A | 8/2000 | Wang |

| | | | |
|---|---|---|---|
| 6,097,994 A | 8/2000 | Navab | |
| 6,129,658 A | 10/2000 | Delfino | |
| 6,129,668 A | 10/2000 | Haynor et al. | |
| 6,130,612 A | 10/2000 | Castellano | |
| 6,140,740 A | 10/2000 | Porat | |
| 6,144,875 A | 11/2000 | Schweikard | |
| 6,173,715 B1 | 1/2001 | Sinanan | |
| 6,198,963 B1 | 3/2001 | Haim | |
| 6,230,038 B1 | 5/2001 | von Gutfeld et al. | |
| 6,239,724 B1 | 5/2001 | Doron | |
| 6,246,900 B1 | 6/2001 | Cosman et al. | |
| 6,363,940 B1 | 4/2002 | Krag | |
| 6,363,982 B1 | 4/2002 | Nixon, Jr. | |
| 6,371,379 B1 | 4/2002 | Dames | |
| 6,385,482 B1 | 5/2002 | Boksberger | |
| 6,400,338 B1 | 6/2002 | Mejia | |
| 6,401,722 B1 | 6/2002 | Krag | |
| 6,405,072 B1 | 6/2002 | Cosman | |
| 6,416,520 B1 | 7/2002 | Kynast et al. | |
| 6,441,741 B1 | 8/2002 | Yoakum | |
| 6,445,856 B1 | 9/2002 | Yang | |
| 6,455,856 B1 | 9/2002 | Gagnon | |
| 6,474,341 B1 | 11/2002 | Hunter | |
| 6,518,884 B1 | 2/2003 | Tanji | |
| 6,675,810 B2 | 1/2004 | Krag | |
| 6,696,686 B1 | 2/2004 | Wainer et al. | |
| 6,698,433 B2 | 3/2004 | Krag | |
| 6,701,179 B1 | 3/2004 | Martinelli et al. | |
| 6,734,795 B2 | 5/2004 | Price | |
| 6,750,020 B2 | 6/2004 | Shuber | |
| 6,812,842 B2 | 11/2004 | Dimmer | |
| 6,905,245 B2 | 6/2005 | Cresens | |
| 6,918,919 B2 | 7/2005 | Krag | |
| 6,937,696 B1 | 8/2005 | Mostafavi | |
| 7,684,849 B2 | 3/2010 | Wright et al. | |
| 7,803,172 B2 | 9/2010 | Khosravi et al. | |
| 7,856,463 B2 | 12/2010 | Yamaguchi et al. | |
| 2001/0018594 A1 | 8/2001 | Krag | |
| 2002/0061298 A1 | 5/2002 | Coffey et al. | |
| 2002/0193685 A1 | 12/2002 | Mate | |
| 2003/0052785 A1 | 3/2003 | Gisselberg | |
| 2003/0088178 A1 | 5/2003 | Owens et al. | |
| 2003/0117269 A1 | 6/2003 | Dimmer | |
| 2003/0117270 A1 | 6/2003 | Dimmer | |
| 2003/0192557 A1 | 10/2003 | Krag | |
| 2004/0015075 A1 | 1/2004 | Kimchy et al. | |
| 2004/0074974 A1 | 4/2004 | Senba | |
| 2004/0125916 A1 | 7/2004 | Herron et al. | |
| 2004/0127787 A1 | 7/2004 | Dimmer | |
| 2004/0199072 A1 | 10/2004 | Sprouse et al. | |
| 2006/0093089 A1* | 5/2006 | Vertatschitsch et al. | 378/65 |
| 2007/0055090 A1 | 3/2007 | Neustadter et al. | |
| 2007/0205373 A1 | 9/2007 | Kornblau et al. | |
| 2007/0265491 A1 | 11/2007 | Krag et al. | |
| 2009/0131734 A1 | 5/2009 | Neustadter et al. | |
| 2009/0216113 A1* | 8/2009 | Meier et al. | 600/424 |

FOREIGN PATENT DOCUMENTS

| | | |
|---|---|---|
| EP | 0719420 | 7/1996 |
| EP | 1034738 | 9/2000 |
| EP | 1094752 A1 | 5/2001 |
| FR | 26335259 | 2/1990 |
| FR | 2686499 | 7/1993 |
| GB | 2 224 183 | 4/1990 |
| GB | 2 258 589 | 2/1993 |
| JP | 8166446 * | 6/1996 |
| WO | WO-88/08282 | 11/1988 |
| WO | WO-92/08513 | 5/1992 |
| WO | WO-95/25475 | 9/1995 |
| WO | WO-95/33519 | 12/1995 |
| WO | WO-96/08208 | 3/1996 |
| WO | WO-96/08999 | 3/1996 |
| WO | WO-96/27328 | 9/1996 |
| WO | WO-97/12553 | 4/1997 |
| WO | WO-97/36192 | 10/1997 |
| WO | WO-97/48438 | 12/1997 |
| WO | WO-98/30166 | 7/1998 |
| WO | WO-98/38908 | 9/1998 |
| WO | WO-98/40026 A | 9/1998 |
| WO | WO-99/13775 | 3/1999 |
| WO | WO-99/17133 | 4/1999 |
| WO | WO-99/27839 | 6/1999 |
| WO | WO-99/30182 | 6/1999 |
| WO | WO-99/33406 | 7/1999 |
| WO | WO-99/35966 | 7/1999 |
| WO | WO-99/40869 | 8/1999 |
| WO | WO-99/44506 | 9/1999 |
| WO | WO-99/58044 | 11/1999 |
| WO | WO-99/58055 | 11/1999 |
| WO | WO-99/58065 | 11/1999 |
| WO | WO 00/12009 | 3/2000 |
| WO | WO-00/24332 | 5/2000 |
| WO | WO-00/38579 | 6/2000 |
| WO | WO-00/51514 | 9/2000 |
| WO | WO-00/53115 | 9/2000 |
| WO | WO-00/65989 A | 11/2000 |
| WO | WO-00/71047 | 11/2000 |
| WO | WO-01/34049 | 5/2001 |
| WO | WO-01/54765 | 8/2001 |
| WO | WO-02/19908 | 3/2002 |
| WO | WO-02/39917 A1 | 5/2002 |
| WO | WO-0239918 A1 | 5/2002 |
| WO | WO-02/100485 | 12/2002 |
| WO | WO-2006/016368 A2 | 2/2006 |
| WO | WO-2007/094001 A2 | 8/2007 |

OTHER PUBLICATIONS

U.S. Appl. No. 10/745,097, filed Dec. 23, 2003, Steven C. Dimmer.
U.S. Appl. No. 10/746,888, filed Dec. 23, 2003, Margo Gisselberg.
U.S. Appl. No. 10/791,662, filed Mar. 2, 2004, David Krag.
International Search Report dated Jul. 16, 1999, PCT Application No. PCT/US99/10683.
International Search Report dated Apr. 13, 2001, PCT Application No. PCT/US00/31673.
International Search Report dated Oct. 8, 2002, PCT Application No. PCT/US02/17876.
PCT Written Opinion dated Jul. 8, 2003, PCT Application No. PCT/US00/31667.
Hsiao, K., "Fast Multi-Axis Tracking of Magnetically-Resonant Passive Tags: Methods and Applications," Feb. 2001, Massachusetts Institute of Technology, Dept. of Electrical Engineering and Computer Science.
International Search Report dated Jan. 24, 2003, PCT Application No. PCT/US02/29390.
International Search Report dated Jul. 3, 2001, PCT Application No. PCT/US00/31667—corresponding to the present application.
The World's Most Versatile Biopsy System Offered Only by USSC, ABBI System Features, © 1997, United States Surgical Corporation, www.ussurg.com/health-care/procedures/abbi.
Kelley, William E., MD, Image-Guided Breast Biopsy: The ABBI System, 1997, www.ussurg.com/health-care/procedures/abbi.
Supplementary Partial European Search Report; Application No. EP00980492; Mar. 23, 2006; 6 pages; European Patent Office.
European Search Report for EP99923067; Calypso Medical Technologies, Inc.; dated Feb. 13, 2007; European Patent Office; 7 pgs.
Final Office Action; U.S. Appl. No. 12/697,139; Mailed on Apr. 27, 2011; 9 pages.s.
Final Office Action; U.S. Appl. No. 12/697,160; Mailed on May 5, 2011; 10 pages.

* cited by examiner

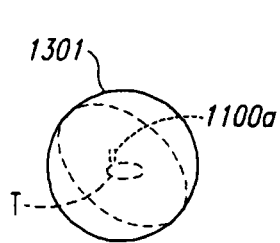 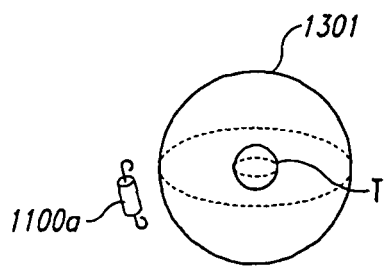
*Fig. 34*     *Fig. 35*
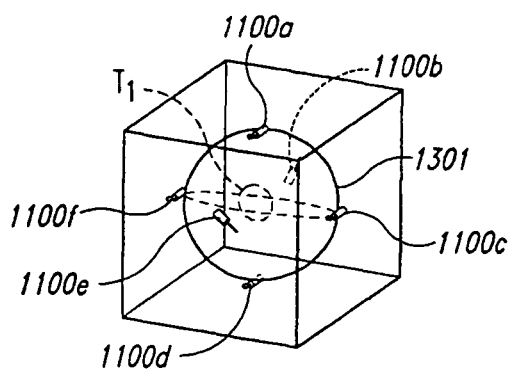 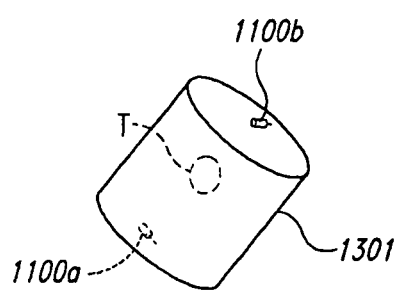
*Fig. 36*     *Fig. 37*
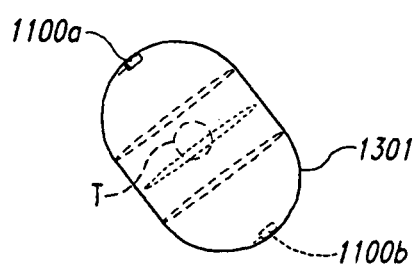 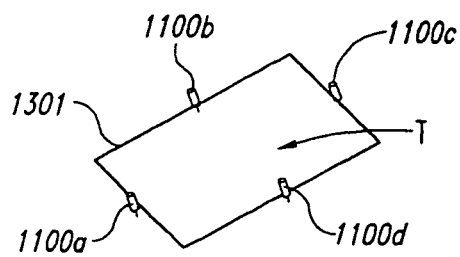
*Fig. 38*     *Fig. 39*

SYSTEMS AND METHODS FOR LOCATING AND DEFINING A TARGET LOCATION WITHIN A HUMAN BODY

CROSS REFERENCE TO RELATED APPLICATIONS

This application is a continuation of U.S. application Ser. No. 10/438,500, filed May 14, 2003, which is a continuation of International Application No. PCT/US00/31667, filed Nov. 17, 2000, which designated the United States and is a continuation-in-part of U.S. application Ser. No. 09/078,982, filed May 14, 1998, now U.S. Pat. No. 6,363,940.

TECHNICAL FIELD

Several aspects of the present invention relate to systems and methods for locating a target tissue within a human body with wireless markers. Other aspects of the invention relate to wireless markers, instruments, user interfaces, and methods for using such systems in treating or monitoring a target location.

BACKGROUND

Many medical procedures require monitoring or treating an internal tissue mass or other body part within a human body. In such applications, medical procedures must accurately locate a small target location within a soft tissue region, an organ, a bone structure, or another body part (e.g., colon, vascular system, etc.). The small target location can be a lesion, polyp, tumor, or another area of interest for monitoring or treating a patient. One particular application involving the surgical treatment of cancer is particularly challenging because physicians often need to treat small, non-palpable lesions that cannot be observed. This problem is compounded in soft tissue applications because the soft tissue is mobile and can move with respect to a reference point on the patient. In the case of breast cancer, for example, the location of a non-palpable lesion in the breast is identified at a pre-operative stage using an imaging system. The actual surgical procedure, however, occurs in an operating room at a subsequent point in time, and the patient is typically in a different position during the surgical procedure than during the pre-operative imaging stage. The breast and the lesion may accordingly be in a different location relative to a reference point on the patient during the surgical procedure than the imaging stage. The physician, therefore, generally estimates the location of lesion during surgery.

One problem with treating non-palpable lesions in soft tissues is that the physicians may incorrectly estimate the location of the lesions. As a result, the physician may not remove all of the lesion, which is not desirable because some of the lesion will accordingly remain in the soft tissue. Another result is that the physicians may remove a significant amount of tissue proximate to the lesion, which can cause undesirable collateral damage to healthy tissue. Therefore, it would be desirable to know the precise location of the lesion or other type of target location during the surgical procedure.

A current technique for performing an excisional biopsy of a non-palpable breast lesion that has been identified by mammogram or other method involves placement of a needle or guide wire (e.g., a "Kopanz wire"), with or without blue dye, to guide the surgeon to the lesion. The tip of the needle is generally placed directly in or as close as possible to the lesion. When larger or more complex lesions are encountered, two or more guide wires are sometimes placed at each edge of the lesion. The entry point of the needle through the skin of the breast is usually several centimeters from the lesion due to the logistics of needle placement. The surgeon does not cut along the shaft of the needle from the skin because the distance is too great. Instead, the surgeon must estimate where in the breast the lesion is located by making reference to the location of the needle.

This technique is not optimal because it can be difficult to properly define the margins of the tissue that is to be removed, both during and after insertion of the needle(s), in tissue that is amorphous and pliable (e.g., breast tissue). Also, it is often difficult for the surgeon to detect the exact depth of the lesion based on the placement of the needles. For these reasons it is not uncommon that the biopsied tissue does not contain the mammographically positive specimen. In other cases, as a result of the difficulty of estimating the proper location of the boundaries of the volume of tissue to be removed, the lesion ends up being eccentrically positioned within the volume of tissue excised. This calls into question the adequacy of the margin of normal tissue surrounding the lesion. In still other cases, more normal tissue is removed than is required, which is disadvantageous in this era of tissue-conserving therapies.

In other fields of surgery it is known to target portions of a human body using various devices, and then refer to such devices in connection with the removal or treatment of such portions. For example, U.S. Pat. No. 5,630,431 to Taylor (the "'431 patent") describes a surgical manipulator that is controlled, in part, by information received from beacons that are positioned proximate to a region of a human body to be treated. As another example, U.S. Pat. No. 5,397,329 to Allen (the "'329 patent") describes fiducial implants for a human body that are detectable by an imaging system. The fiducial implants are implanted beneath the skin and are spaced sufficiently from one another to define a plane that is detectable by the imaging system and is used in connection with creation of images of a body portion of interest. These images are then used, for instance, in eliminating a tumor by laser beam.

Unfortunately, the devices described in the '431 and '329 patents are vastly more complex, and hence expensive, than is appropriate for many surgical procedures. This problem is particularly disadvantageous with the emphasis on containing costs in managed health care. Furthermore, due to the amorphous, pliable nature of certain tissue, the systems of the '431 and '329 patents cannot be used effectively. Systems of the type described in the '431 and '329 patents require that the devices (e.g., beacons or fiducial implants) defining the body portions of interest be substantially fixed relative to one another and relative to such body portions. These systems generally function effectively when the devices defining the body portion of interest are inserted in bone, e.g., in a skull in connection with brain surgery or treatment, but are not believed to operate as intended when the devices are inserted in amorphous, pliable tissue.

Breast lesions are typically excised with a scalpel manipulated directly by the surgeon. With the current emphasis on surgical therapies that conserve breast tissue, the above-described procedure for removing a breast lesion is typically performed through a narrow opening in the skin created by slitting and then pulling apart the skin. It tends to be difficult to manipulate the scalpel within this opening so as to remove the desired volume of tissue. The amorphous, pliable nature of breast tissue exacerbates removal of such tissue inasmuch as application of force to the scalpel causes movement of the breast tissue relative to the opening in the skin.

Circular cutting tools are not widely used in surgery. Recently, however, United States Surgical Corporation of Norwalk, Conn., introduced a relatively small diameter, e.g., 5-20 mm, circular cutting tool identified by the trademark ABBI for removing a cylinder of breast tissue for biopsy purposes. The ABBI tool includes an oscillating, motorized, circular cutting blade that incises the breast tissue. While use of the ABBI tool is believed to be a relatively effective way to perform a core biopsies of breast tissue, it is not apparently designed to remove cylinders of tissue having a diameter much in excess of about 20 mm. As such, it is not adapted for use in surgeries involving the removal of relatively large tissue portions in a single cutting sequence. In addition, the effectiveness of the ABBI tool in therapeutic, rather than diagnostic, surgeries has not been confirmed.

Detectors are used to locate organs or other portions of the body that have taken up a radioactive material, e.g., an antibody labeled with a radioactive material. For example, the gamma ray probe described in U.S. Pat. Nos. 5,170,055 and 5,246,005, both to Carroll et al., and sold by Care Wise Medical Products Corporation, Morgan Hill, Calif., and identified by the trademark C-TRAK, provides an audio output signal, the pitch of which varies with changes in relative proximity between the probe and a body portion that has taken up an antibody labeled with a gamma ray producing material, e.g., technetium 99. Once the body portion is detected, it is removed by known surgical techniques.

Even with the systems and techniques described above, it remains difficult for a surgeon to remove a tissue mass in amorphous, pliable tissue, such as breast tissue, so as to ensure that the entire tissue mass is removed while at the same time conserving portions of adjacent tissue. As a result, more tissue surrounding the targeted tissue mass is typically removed than is desired.

SUMMARY

The present invention is directed toward methods, systems, and system components for finding a target location within a human body. In one aspect of the invention, a system comprises a first wireless implantable marker configured to be implanted within the human body at a location relative to the target location, an instrument having a function-site and a first instrument marker connected to the instrument at a first predetermined site relative to the function-site, a position detection system, and a user interface. The position detection system can have a sensor that detects (a) a position of the first wireless implantable marker relative to a reference location and (b) a position of the first instrument marker relative to the reference location. The position detecting system can also include a computer that determines a relative position between the first wireless implantable marker and the first instrument marker based on the positions of the first wireless marker and the first instrument marker relative to the reference location. The user interface is operatively coupled to the position detection system. The user interface can have an indicator that denotes the position of the function-site of the instrument relative to the target location based on the relative position between the first wireless implantable marker and the first instrument marker.

In another aspect of the invention, a wireless implantable marker comprises a biocompatible casing configured to be implanted into a human body relative to a target location within the human body, a signal element in the casing, and a fastener. The signal element is configured to emit a response energy in reaction to an excitation energy. The fastener is configured to hold the wireless marker at a reference location in a human body relative to the target location within the human body.

Yet another aspect of the invention is an instrument for manipulation within a human or proximate to the human. The instrument can comprise a handle, a function-site coupled to the handle, and a first wireless instrument marker. The function-site is aligned with an alignment axis, and the first wireless instrument marker can be positioned along the alignment axis. The first wireless instrument marker is also configured to emit a wireless signal that can be detected by a position detection system to determine a position of the first wireless instrument marker relative to a reference location.

The systems and components can be used in many applications in which it is desirable to accurately know the relative position between an instrument and a target location within a human body. For example, one embodiment of a method of treating a target location within a human body comprises exciting a wireless marker implanted in the body by emitting an excitation energy in a manner that causes the marker to emit a response energy. The method can continue by sensing the response energy and determining a position of the wireless marker relative to a reference location based on the sensed response energy. In other aspects, the method can also include determining a position of an instrument with a marker relative to the reference location, and displaying the relative position between the instrument and the target location. Other aspects of the invention are described in the following detailed description of the invention and the claims, and the accompanying drawings illustrate several embodiments of the invention.

BRIEF DESCRIPTION OF THE DRAWINGS

FIG. 3b is a block diagram of the RF exciter used with the marker illustrated in FIG. 3a.

FIGS. 34-39 are isometric views of arrangements for implanting the wireless implantable markers relative to a target location T in accordance with embodiments of the invention.

DETAILED DESCRIPTION

The following description is directed toward systems and methods for locating and defining a target location within a human body. Several aspects of one system in accordance with an embodiment of the invention directed toward bracketing a target location with at least one marker are described below in Section I. Similarly, aspects of other systems in accordance with embodiments of the invention directed toward locating a target mass within a human body using the relative orientation between an implanted marker and an instrument are described below in Section II. Other aspects of embodiments of the invention directed toward defining and displaying a virtual boundary relative to a target location based on the location of an implanted marker are also described below in Section II.

I. Systems and Methods for Delineating a Target Location Using Bracketing

FIGS. 1-20 illustrate a system and several components for delineating a target location within a human body in accordance with several embodiments of invention. Several of the components described below with reference to FIGS. 1-20 can also be used in the systems set forth with respect to FIGS. 21-61. Therefore, like reference numbers refer to like components and features throughout the various figures.

Figure 1:
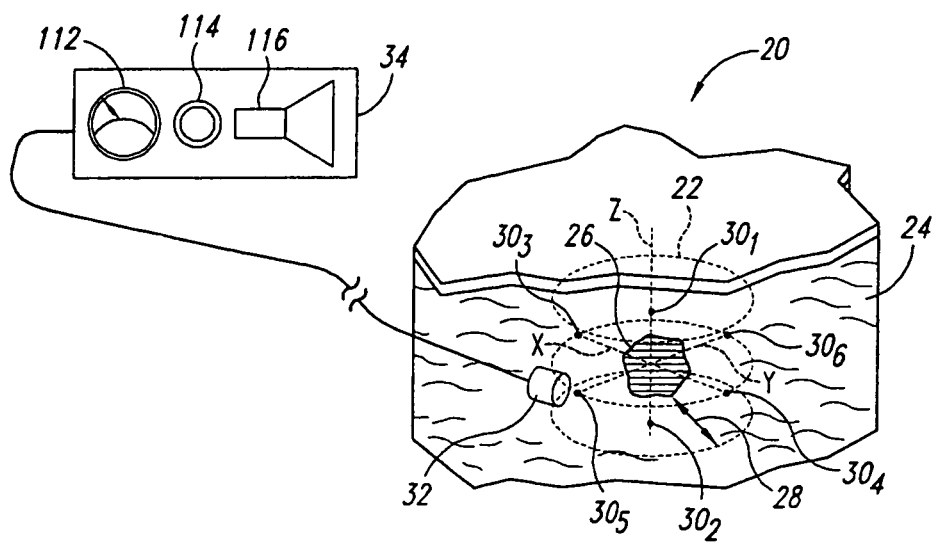
FIG. 1 is an isometric view representative of a tissue mass and surrounding tissue volume that is bracketed by the markers, with two markers being positioned on opposite ends of each of mutually orthogonal X, Y and Z-axes intersecting the tissue mass so as to define the boundary of the tissue volume, and with the probe and detector being positioned adjacent the tissue volume in accordance with one embodiment of the invention.

Referring to FIG. 1, one aspect of the present invention is a system 20 for defining the boundaries of, i.e., bracketing, a tissue volume 22 in a tissue portion 24. Typically, tissue volume 22 will include a tissue mass 26, e.g., a breast lesion, that is targeted for removal and a tissue margin 28 of unaffected tissue surrounding the tissue mass. After tissue volume 22 is bracketed, system 20 can be used to locate the defined boundaries of the tissue volume, e.g., in connection with the surgical removal of tissue mass 26. It will be appreciated that the invention can have other applications including radiation therapy, colo-rectal treatments, and many other applications in which it is useful to locate a target location other than a tissue volume within a human body.

As described in more detail below, other aspects of the present invention are also directed to a method of bracketing tissue volume 22 using system 20, and a method of removing tissue volume 22 using system 20. These methods can be accomplished with other aspects of the present invention, such as markers, instruments, stabilizers/anchors, position detection systems and user interfaces described below.

System 20 comprises a plurality of markers 30, a probe 32 and a detector 34 connected to the probe. As described in more detail below, markers 30 are implanted in tissue portion 24 under the guidance of a conventional imaging system not forming part of the present invention, so as to bracket tissue volume 22. Such imaging systems may include ultrasound, magnetic resonance imaging ("MRI"), computer-aided tomography ("CAT") scan, and X-ray systems. Markers 30 are imageable with the imaging energy generated by the imaging system. For example, if an ultrasound imaging system is used to implant markers 30, the latter are configured and made from a material that strongly reflects ultrasound energy. Materials that are imageable with the energy generated by such systems are well known to those skilled in the art, and so are not described in detail here. Following implantation of markers 30, probe 32 and detector 34 are used to locate the markers, as described in more detail below.

The terms "probe 32" and "detector 34" are used generically herein to refer to all embodiments of the probe and detector described below. Specific embodiments of the probe 32 and detector 34 are identified using a prime notation described below, i.e., probe 32' or detector 34". Additionally, the probes described below define one type of instrument, and the detectors described below define one type of position detection system in accordance with embodiments of the invention.

A. Markers

The markers 30 can be biologically inert (biocompatible) and are relatively small so that they do not impair procedures for removing or treating a tissue volume 22. Markers 30 may have different geometric configurations, e.g., spherical, disk-like, cylindrical, and other shapes. In one particular embodiment, the greatest dimension of a marker 30 measured along a Y-axis extending through the marker from one surface to an opposite surface is not more than about 5 mm. The markers 30 can be even smaller, e.g., the greatest dimension is about 1-2 mm, or they can also be larger. Although several of the markers with respect to FIGS. 2-8 are described in connection with this aspect of the invention, they can also be used in connection with other aspects.

In addition, markers 30 each have a detection characteristic to enable detection by probe 32 and detector 34, or by a separate detection system with an array of sensors relative to a reference location. The detection characteristics of the various embodiments of markers 30 can be characterized as active or passive. In the active category, the detection characteristic of a first embodiment of marker 30, illustrated in FIG. 2a as marker 30a, is gamma radiation 40. In this regard, marker 30a may include materials such as technetium 99, cobalt isotopes or iodine isotopes. Such materials may be obtained from DuPont of Billerica, Mass. Preferably, each marker 30a generates gamma radiation 40 having a field strength in the range of 1-100 microCuries.

Figure 2A:
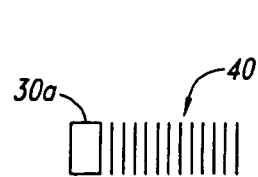
FIGS. 2a-2g are schematic representations of various embodiments of the markers of the present invention and their associated detection characteristics.
Figure 2B:
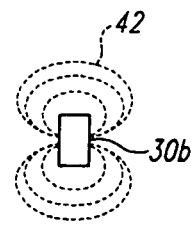

Also in the active category, in a second embodiment of marker 30, illustrated in FIG. 2b as marker 30b, the detection characteristic is magnetic field 42. Markers 30b of the second embodiment thus contain ferromagnetic materials in which a magnetic field can be induced, or alternatively are permanently magnetized and so have an associated permanent magnetic field. In FIG. 2b, magnetic field 42 represents both the induced and inherent magnetic fields. Strong permanent magnets, such as those made from Samarium-Cobalt, can be suitable magnets for markers 30b. Alternatively, the markers may communicate with the position detection system by resonating markers (e.g., AC magnetic coupling using coils of wire as receiving and emitting antenna), as described below with reference to FIGS. 23A-D.

Figure 2C:
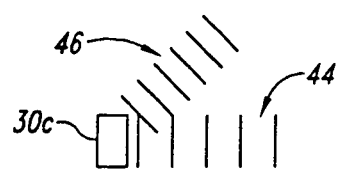

Referring to FIG. 2c, in a third embodiment, again in the active category, marker 30c emits radio frequency ("RF") signal 44 in response to a triggering signal 46. Various energy sources may be used for triggering signal 46, including a magnetic field, ultrasound or radio frequency energy. In this latter case, marker 30c is preferably designed to receive triggering signal 46 which has a first RF wavelength, and in response thereto, emit signal 44 of a second RF wavelength. In the simplest case, no data, other than the specific radio frequency itself, is carried in signal 44. Alternatively, markers 30c may all transmit signal 44 at a single frequency, with data uniquely identifying each marker being carried in signal 44 emitted by each marker.

Figure 3A:
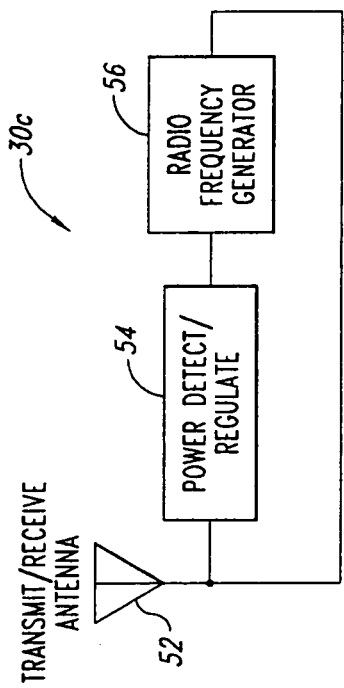
FIG. 3a is a block diagram of the elements of one embodiment of the marker illustrated in FIG. 2c.

A suitable marker 30c is illustrated in FIG. 3a. This marker 30c includes a transmit/receive antenna 52 for receiving an RF signal at a first frequency and transmitting an RF signal at a second frequency. Also included is a power detect/regulate circuit 54 connected to antenna 52 that detects the presence of, and regulates, the RF signal received by the antenna. The regulated RF signal is provided from circuit 54 to drive radio frequency generator 56 which generates an RF signal at a second frequency. As discussed in more detail below, when multiple markers 30c are used together in a given bracketing procedure, preferably each marker transmits RF signals at a second frequency which is unique to the marker. The frequency of the received RF signal 46, however, is preferably common with respect to all of the markers 30c used in the bracketing procedure. The RF signal generated by radio frequency generator 56 is then provided to antenna 52 where it is transmitted as an RF signal.

Figure 3B:
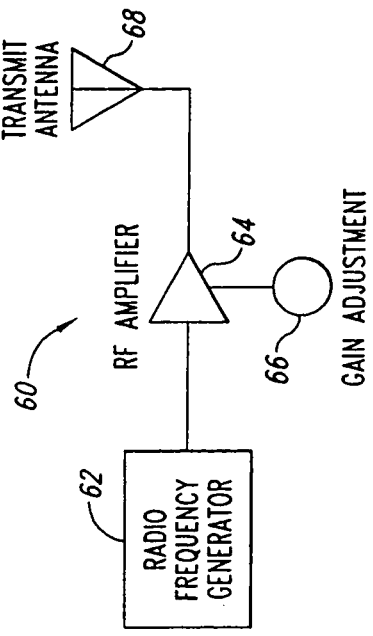
Figure 4:
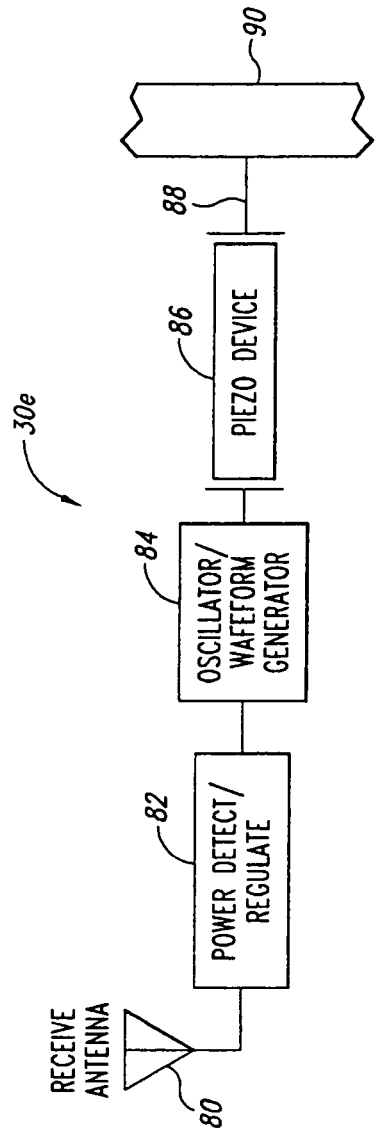
FIG. 4 is a block diagram of the elements of one embodiment of the marker illustrated in FIG. 2e.

Referring to FIG. 3b, an RF exciter device 60 for generating RF signal 46 is illustrated. RF exciter 60 includes a radio frequency generator 62 for generating RF signal 46 at a predetermined frequency and an RF amplifier 64 for amplifying the output from the radio frequency generator. The sensitivity of amplifier 64 may be controlled using gain adjustment 62 coupled to the amplifier. The output of RF amplifier 64 is provided to transmit antenna 68 which transmits RF signal 46. Transmit antenna 68 of RF exciter 60 is preferably placed in relatively close proximity to marker 30c, with appropriate gain adjustment of RF amplifier 64 being achieved by control gain adjustment 66 until a suitable return signal is absorbed from detector 34", discussed below and illustrated in FIG. 8.

Figure 2D:

In a fourth embodiment, again in the active category, marker 30d, illustrated in FIG. 2d, continuously emits signal 44 at specific frequencies in the radio frequency spectrum. The marker 30c illustrated in FIG. 3A and described above can be satisfactorily employed as marker 30d by adding a battery (not shown) in place of power detector portion of circuit 54 of marker 30c. RF exciter 60 is not required in connection with marker 30d, insofar as the battery generates the energy used by the marker in producing RF signal 44. The embodiments of the RF Markers are one example of a resonating marker having an electrical circuit in accordance with an embodiment of a wireless implantable marker.

Figure 2E:
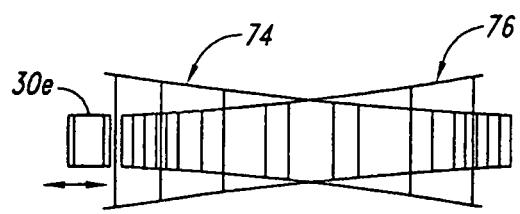

As a fifth embodiment in the active category, marker 30e, illustrated in FIG. 2e, is designed to vibrate following implantation. This vibration is a detection characteristic that is chosen to enhance image contrast when marker 30 is intended to be detected using a probe 32 and detector 34 that perform ultrasound imaging. More specifically, incoming ultrasound signal 74 is reflected off marker 30e as reflected ultrasound signal 76, with a Doppler shift component being added to the reflected signal due to the vibration of the marker to enhance imageability of the marker. The vibration frequency of marker 30e will vary depending upon the frequency of ultrasound energy generated by probe 32, but is preferably lower than the frequency of incoming ultrasound signal 74 which is typically 7.5 MHz, i.e., the vibration frequency is preferably in the 50 Hz to 50 kHz range. This embodiment is an example of a mechanical resonating marker in accordance with another embodiment of a wireless implantable marker.

A suitable marker 30e that achieves the functionality described above is illustrated in FIG. 4. This marker 30e includes an antenna 80 for receiving an RF signal that provides the energy driving the marker. A power detection and regulation circuit 82 is connected to antenna 80 for detecting when the antenna is receiving an RF signal and for regulating the signal for use by oscillator and waveform generator circuit 84 connected to circuit 82. Circuit 84 converts the regulated RF signal received from circuit 82 into an oscillating electrical signal, preferably in the audio frequency range (i.e., 20 Hz-20 kHz), having a waveform that is optimized to drive piezoelectric device 86 connected to circuit 84. Piezoelectric device 86 is a conventional piezoelectric device of the type that converts an oscillating electrical input signal into mechanical oscillations. Piezoelectric device 86 is attached via support 88 to outer housing 90 of marker 30e. Housing 90 is designed to resonate at the mechanical oscillation frequency of piezoelectric device 86.

Figure 5:
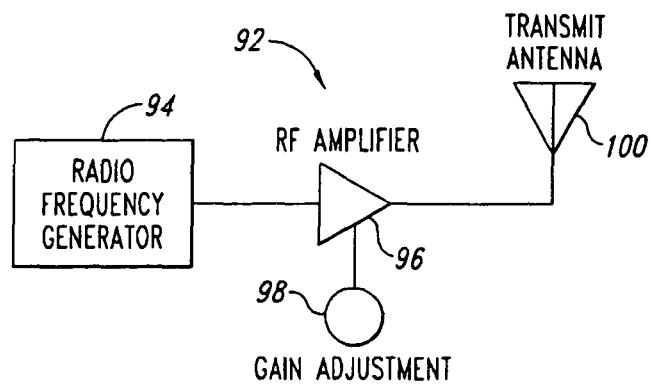
FIG. 5 is a block diagram of the RF exciter used with the marker illustrated in FIG. 4.

Referring to FIG. 5, an RF coupled acoustic exciter 92 is provided for generating the RF signal received by antenna 80 of marker 30e. Exciter 92 includes a radio frequency generator 94 for generating an RF signal. RF amp 96, with a gain adjustment 98 connected thereto, is provided for receiving and amplifying the output signal from generator 94. A transmit antenna 100 is provided for receiving the output of amp 96 and transmitting the RF signal used to drive marker 30e. In use, gain 98 of amp 96 is adjusted to amplify the RF signal produced by generator 94 such that marker 30e is caused to mechanically oscillate so it is most clearly observable by the ultrasound imaging system (not shown) used in conjunction with marker 30e.

As those skilled in the art will appreciate, other circuit configurations may be used in marker 30e to cause piezoelectric device 86 to vibrate. For example, a frequency divider circuit (not shown) may be used in place of oscillator/waveform generator circuit 84. With such alternative, exciter 92 is modified to include a variable frequency oscillator (not shown) in place of radio frequency generator 94.

Figure 2F:
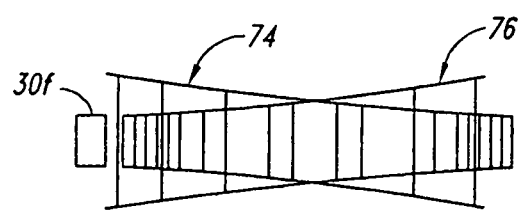

In the passive category, the detection characteristic in a sixth embodiment of marker 30, illustrated as marker 30f in FIG. 2f, is opacity to incoming ultrasound signal 74. That is, marker 30f reflects incoming sound energy sufficiently to create a strong image in reflected signal 76 so as to enhance imageability using a conventional ultrasound imaging system. In many cases, it will be advantageous to incorporate the detection characteristics of marker 30f in marker 30e.

Figure 6:
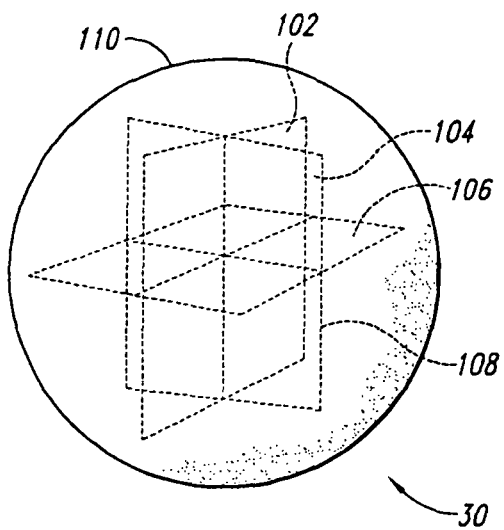
FIG. 6 is a perspective view of one embodiment of the marker illustrated in FIG. 2F, with details of internal construction being illustrated in phantom view.

While those skilled in the art are familiar with materials and configurations that can be used for marker 30f, one suitable marker 30f is illustrated in FIG. 6. This marker 30f includes plate 102, plate 104 and plate 106, all of which are preferably arranged in mutually orthogonal relationship. It is preferred that each of the plates 102-106 has a square configuration and the length of each edge of the plates, e.g., the length of edge 108 of plate 104, is preferably about twice the wavelength of incoming ultrasound signal 74. For example, when incoming ultrasound signal 74 has a wavelength of 7.5 MHz, edge 108 has a length of about 2 mm. Plates 102-106 are made from a material that strongly reflects ultrasound energy, e.g., aluminum, and typically have a thickness in the range of 10-100 µm. Plates 102-106 ideally are enclosed in a biologically non-reactive casing 110. The latter is preferably made from a material that does not have strong ultrasound reflection characteristics, e.g., a soft polymer.

Figure 2G:
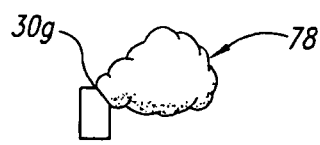

Also in the passive category, marker 30g of the seventh embodiment, illustrated in FIG. 2g, comprises a capsule (not shown) filled with a colored dye 78, e.g., a vital dye. Either or both the capsule and dye 78 of marker 30g are made from a material that is imageable by the imaging system, e.g., ultrasound, used to implant the markers, as described in more detail below. The capsule is made from gelatin or other suitable material that is selected to be sufficiently tough to withstand insertion into tissue volume 22, but is relatively easily cut by the cutting tool used to remove the tissue volume, e.g., a conventional surgical scalpel or cutting tool 200 described below. Marker 30g provides a visual guide as to its location by releasing colored dye 78 when severed by a surgical cutting tool. In this regard, probe 32 and detector 34 are not used in connection with marker 30g.

Markers 30a, 30b and 30f may be made from a solid structure containing material having the desired detection characteristic. Alternatively, markers 30a, 30b and 30f may be made from a capsule filled with a dye, such as is used for marker 30g, containing material having the desired detection characteristic. As another alternative, all embodiments of markers 30 may include a dye contained in an outer capsule having the requisite toughness and severability characteristics noted above.

B. Probe and Detector

The probe 32 shown in FIG. 1 is one embodiment of an instrument, and the detector 34 shown in FIG. 1 is one embodiment of a user interface for any system in accordance with the invention. The design and configuration of the probe 32 and the detector 34 depend upon the embodiment of marker 30 used. However, for all embodiments of marker 30 (except marker 30g), detector 34 is designed to provide humanly recognizable information when probe 32 is positioned within a selected proximity, e.g., 1-5 cm, of a given marker. This information may take one of a variety of forms, including a burst of humanly perceivable sound, constant or intermittent illumination of a light, movement of a needle on a dial, a short burst of air, change of data in a visual display, increased image brightness or contrast (in the case when detector 34 is an ultrasound imaging system, as discussed below), a tactile response, or other humanly perceivable proximity information. In this regard detector 34 may include a dial 112, light 114, speaker 116, or other appropriate devices for generating the selected form of humanly perceivable information.

Preferably, although not necessarily, detector 34 provides humanly recognizable information that indicates changes in proximity of probe 32 to a given marker 30. Thus, rather than merely providing static or threshold information that probe 32 is within a predetermined range of a given marker 30, detector 34 preferably provides proximity information having an attribute or characteristic that varies as a function of changes in proximity of the probe relative to the marker. For example, if the proximity information is sound, the pitch is varied with changes in proximity. Or, as another example, if the proximity information is light, the brightness of the light changes with changes in proximity.

A probe and detector that may be satisfactorily employed as probe 32 and detector 34, respectively, when the latter is intended to detect maker 30a, is sold by Care Wise Medical Products Corporation of Morgan Hill, Calif., and is identified by the trademark C-TRAK. The C-TRAK probe, which is described in U.S. Pat. Nos. 5,170,055 and 5,246,005 to Carroll et al., which are incorporated herein by reference, provides a humanly audible sound, the pitch of which varies with changes in proximity of the probe to tissue labeled with gamma ray producing material.

Figure 7:
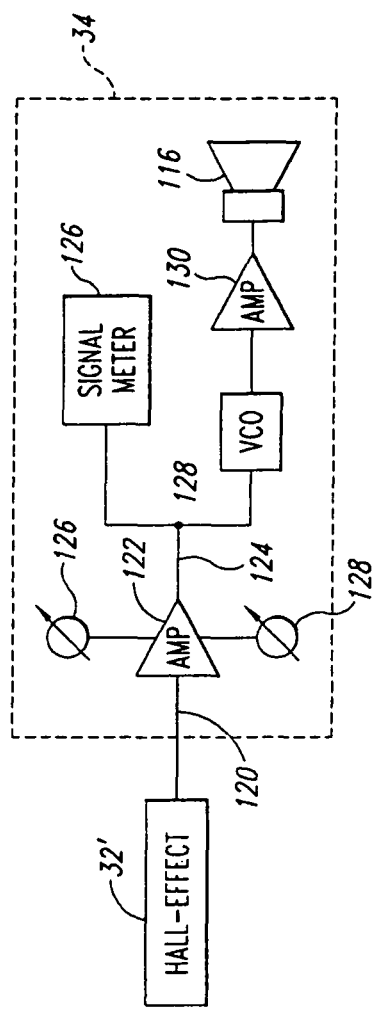
FIG. 7 is a block diagram of the probe and detector used with the marker illustrated in FIG. 2b.

Referring to FIGS. 1, 2b and 7, when probe 32 and detector 34 are intended for use in detecting marker 30b, which generates a magnetic field 42, probe 32' and detector 34' illustrated in FIG. 7 may be satisfactorily employed. Probe 32' includes a conventional Hall effect sensor (not shown) that provides an output signal on line 120, the voltage of which varies as a function of proximity of the probe to the magnetic field generated by a marker 30b. Detector 34' is connected to probe 32' via line 120, and includes an amplifier 122 connected to line 120 for amplifying the signal from the Hall effect sensor in probe 32'. Amplifier 122 includes an offset adjustment 126 and a gain adjustment 128. Offset adjustment 126 is provided to cancel the effects of any ambient magnetic fields, such as that of the earth. Gain adjustment 128 is provided to control the overall sensitivity of detector 34'. The amplified signal from amplifier 122 is delivered on line 124 to signal meter 126, which may comprise a dial with a movable needle, an LED or other device for representing signal strength. Also connected to line 124 is voltage-controlled oscillator 128, the output of which is provided to amplifier 130. The output of amplifier 130 drives speaker 116. The frequency of the output signal from voltage controlled oscillator 128 varies as function of changes in voltage of the signal delivered on line 124, which in turn causes the pitch of the sound produced by speaker 116 to vary as a function of changes in the voltage of the signal on line 124. As those of ordinary skill in the art will appreciate, other devices for providing humanly recognizable information representing changing proximity, e.g., a light, may be employed instead of speaker 116.

Figure 8:
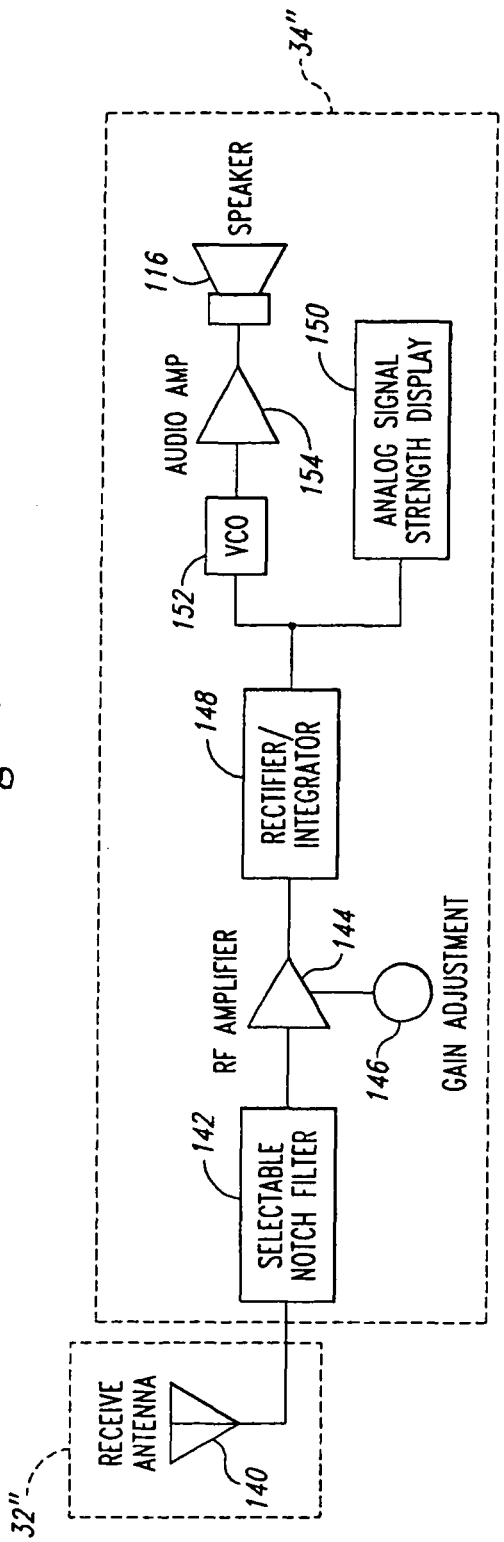
FIG. 8 is a block diagram of the probe and detector used with the marker illustrated in FIG. 2c.

Referring to FIGS. 1, 2c and 8, for markers 30c and 30d, which generate radio frequency energy, probe 32" and detector 34" are provided for use in detecting the markers. Probe 32" includes a conventional coil antenna 140 for receiving an RF signal. Detector 34" includes a selectable notch filter 142 connected to antenna 140 which permits tuning of the detector to the unique RF frequency of signal 44 emitted by markers 30c or 30d. A tuning knob or other user adjustable mechanism (neither shown) is attached to selectable notch filter 142 to permit a user to perform such tuning. The output of selectable notch filter 142 is provided to RF amplifier 144, the overall sensitivity of which may be controlled by gain adjustment 146 attached to the amplifier. The output of RF amplifier 144 is provided to rectifier/integrator circuit 148 which rectifies and time filters the signal. The output of rectifier/integrator circuit 148 is provided to analog signal strength display 150 which provides a visual indication of the proximity of probe 32" to marker 30c. In addition, the output of rectifier/integrator circuit 148 is provided to voltage oscillator 152 which generates an output signal, the frequency of which varies as a function of the voltage level of the signal provided by rectifier/integrator circuit 148. The output signal of the voltage control oscillator 152 is amplified by audio amplifier 154, which in turn drives speaker 116. Accordingly, the pitch of the sound generated by speaker 116 varies as a function of the strength of the RF signal received by probe 32", and hence as a function of the proximity of probe 32" to markers 30c or 30d.

A suitable probe 32 and detector 34 for use with the markers 30e and 30f is the ultrasound imaging system available from Dornier Surgical Products, Inc., Phoenix, Ariz., is identified by the name Performa, and generates ultrasound energy having a frequency of 7.5 MHz.

C. Tissue Anchor

Figure 9:
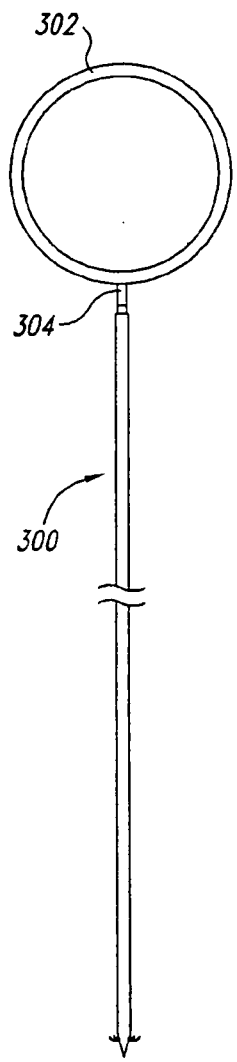
FIG. 9 is a front elevation view of a tissue anchor in accordance with one embodiment of the invention, with the cannula and rod of the cutter being shown in broken view to facilitate illustration.
Figure 10:
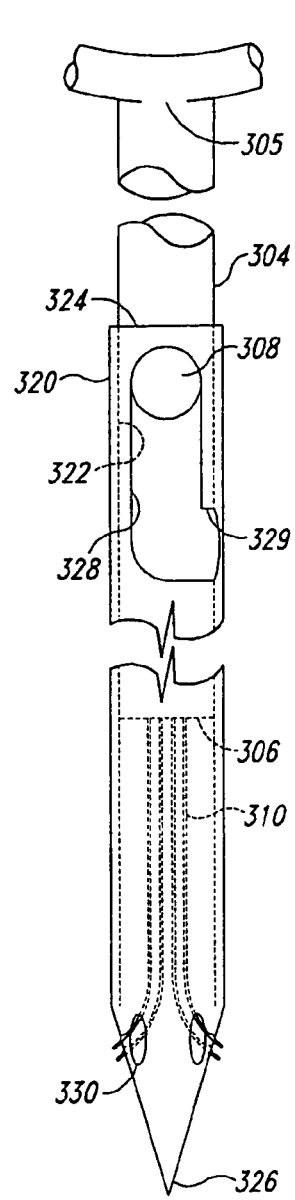
FIG. 10 is an enlarged view of the tissue anchor in FIG. 9, with the rod and cannula both being broken at first location and the rod alone being broken at a second location to facilitate illustration, also with the rod being shown in a retracted position relative to the cannula.
Figure 11:
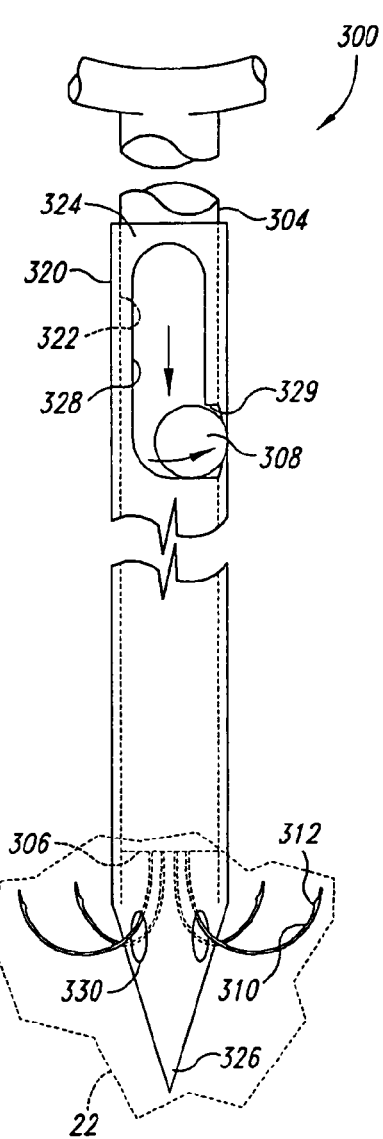
FIG. 11 is similar to FIG. 10, except that the rod is shown in the extended position relative to the cannula, with the anchor members attached to the end of the rod being shown in an extended position engaged in a portion of a tissue mass.

Turning now to FIGS. 9-11, another aspect of the present invention is tissue anchor 300. The latter is designed to stabilize tissue mass 26 during surgical removal of the mass using system 20, as described in more detail below.

Tissue anchor 300 includes a ring 302 sized to receive the thumb or finger of a user, and a rod 304. The latter includes a proximal end 305, which is attached to ring 302, and a distal end 306. Rod 304 includes an outwardly projecting pin 308 that serves as a stop, as described below. Tissue anchor 300 also includes a plurality of, e.g., four, anchor members 310 that are attached to rod 304 at or adjacent its distal end 306. Typically, anchor members 310 are attached to rod 304 so as to extend away from its distal end 306, as illustrated in FIGS. 9 and 10. However, as an alternative design, anchor member 310 may be attached to rod 304 so as to extend away from distal end 306 toward proximal end 305 (not shown). Each anchor member 310 may terminate with a barb 312 (FIG. 11), if desired. Anchor members 310 preferably have a curved configuration when in an unbiased state, as illustrated in FIGS. 9 and 11. Anchor members 310 are preferably made from spring steel, although other "memory" metal alloys made also be satisfactorily used. In certain applications it may be unnecessary to provide a curve in anchor member 310, i.e., the anchor member may be substantially straight.

Rod 304 preferably, although not necessarily, has a circular cross section. The outside diameter of rod 304 depends upon its intended application, but is typically in the range of 0.3-10 mm, preferably about 1-2 mm. The length of rod 304, as measured between proximal end 305 and distal end 306, also depends upon its desired application, but typically ranges from 5-20 cm.

Tissue anchor 300 also includes a cannula 320 having a central bore 322, a proximal end 324 and a pointed distal end 326. Central bore 322 has an inside diameter that is sized to receive rod 304 with a close sliding fit. Cannula 320 has an outside diameter that is selected based on the intended application but is typically in the range 0.5 mm-12 mm, preferably about 1-3 mm. Cannula 320 also includes an elongate slot 328 that runs parallel to the long axis of the cannula and is sized to receive pin 308 with a close sliding fit. The length of slot 328 is substantially the same as the length of anchor members 310. Slot 328 includes a pocket 329 at its end closest to distal end 326 of cannula 320 that extends orthogonally to the long axis of the slot and is sized to receive pin 308.

Cannula 320 also includes a plurality of apertures 330 extending through the wall of the cannula. Apertures 330 are positioned adjacent distal end 326 of cannula 320 when anchor members 310 are attached to rod 304 to extend away from distal end 306 as illustrated in FIGS. 10 and 11. If anchor members 310 extend from distal end 306 toward proximal end 305 (not shown), then apertures 330 are moved toward the proximal end so that they are spaced from the distal end 326 at least about the length of the anchor members. One aperture 330 is typically provided for each anchor member 310. The lengths of anchor members 310, cannula 320, and slot 328 are together selected so that a small portion, e.g., about 1 mm, of each anchor member 310 projects from its respective aperture 330 when tissue anchor 300 is in the retracted position illustrated in FIG. 10. In this position, pin 308 engages the end of slot 328 closest to proximal end 324. Anchor members 310 are sized in this manner to ensure the anchor members remain positioned in their respective apertures 330 when tissue anchor 300 is in the retracted position illustrated in FIG. 10.

The lengths of anchor members 310, cannula 320, and slot 328 are also together selected so that most, if not substantially the entire, length of the anchor members 310 projects from their respective apertures 330 when tissue anchor is in the extended position illustrated in FIGS. 9 and 11. In this position, pin 308 engages the end of slot 328 closest to distal end 326.

The elements of tissue anchor 300 are preferably made from stainless steel, a plastic such as polystyrene or polyurethane, or other materials suitable for the intended application of the tissue anchor (as described in more detail below) known to those skilled in the art. As noted above, in many cases it is desirable to make anchor members 310 from spring steel or a "memory" metal alloy.

D. Bracketing

Figure 12:
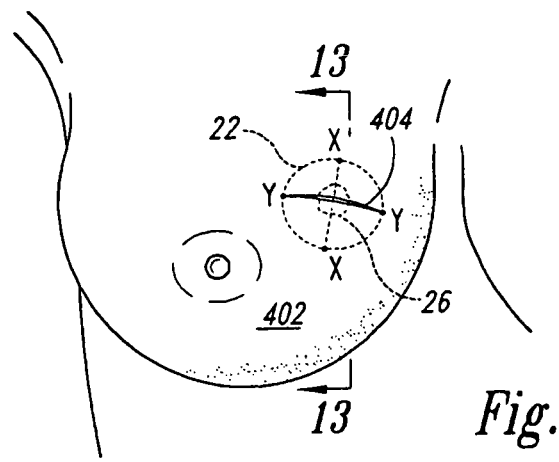
FIG. 12 is a top view of a breast of woman in a supine position, with a tissue mass being surrounded by markers of one embodiment of the present invention so as to define the tissue volume to be removed, and with an incision formed in the skin of the breast above the tissue volume.
Figure 13:
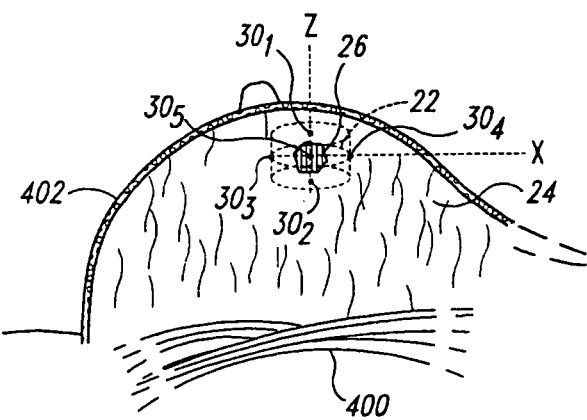
FIG. 13 is a cross-sectional view of the breast of FIG. 12 taken along line 13-13 in FIG. 12.

Referring now to FIGS. 1, 12 and 13, markers 30 may be used to bracket (i.e., define the boundaries of) tissue volume 22 in a tissue portion 24 in accordance with the following method. In the following description of the method of bracketing tissue volume 22, the latter is contained in a human breast. However, it is to be appreciated that tissue volume 22 may be present in other hollow or solid organs and structures, e.g., a liver, or may constitute an entire organ or structure. Additionally, a plurality of the markers 30 may be implanted to completely bracket the tissue volume 22, or one or more markers 30 can be used to bracket or otherwise mark the location of the tissue volume 22.

As the first step in bracketing tissue volume 22, a tissue mass 26 of interest is identified through conventional imaging methods, e.g., ultrasound, MRI, X-ray or CAT scan. Next, markers 30 are implanted in tissue portion 24 surrounding tissue mass 26 and defining outer boundaries of tissue volume 22. The number of markers 30 used, and the placement of the markers relative to tissue mass 26, will vary depending upon the location of the tissue mass relative to other types of tissue, e.g., bone or muscle, surgeon preference, size and configuration of the tissue mass and the desired amount of tissue margin 28 (FIG. 1) beyond the edge of tissue mass 26. However, in many applications, it may be desirable to use at least six markers 30 to bracket tissue volume 22, preferably two on each of axes X, Y and Z (see, e.g., FIGS. 1, 12 and 13). Two of the markers 30 can be positioned on each of axes X, Y and Z so as to lie on opposite boundaries of tissue volume 22. For example, as illustrated in FIG. 1, marker 30₁ lies on the Z-axis at the upper surface of tissue volume 22, marker 30₂ lies on the Z-axis at the lower surface of the tissue volume, marker 30₃ lies on the X-axis at a first location on the outer surface of the tissue volume, marker 30₄ lies on the X-axis at a second location on the outer surface of the tissue volume diametrically opposite marker 30₃, marker 30₅ lies on the Y-axis at a third location on the outer surface of the tissue volume, and marker 30₆ lies on the Y-axis at a fourth location on the outer surface of the tissue volume diametrically opposite marker 30₅.

Although the axes X, Y and Z can be mutually orthogonal, as illustrated, this is not mandatory and can be difficult to precisely implement in practice. In this particular embodiment, the tissue volume 22 should be completely surrounded by markers 30, i.e., the tissue volume should be defined in three dimensions by the markers. One notable exception to this that the marker 30, such as marker 30₂ shown in FIGS. 1 and 13, positioned at the base of, i.e., underneath, tissue volume 22 is not typically required when a different type of tissue, such as pectoral muscle 400 (FIG. 13) is located at or near where the marker would be positioned. The illustration of marker 30₂ in FIG. 13 is not inconsistent with this recommended placement regime for markers 30 because of the relatively great spacing between the marker 30₂ and pectoral muscle 400. Similarly, when the marker 30, such as marker 30₁ shown in FIG. 1, to be positioned on top of tissue volume 22 is near the skin overlying the tissue volume, such marker is not typically required. Also, while the X, Y and Z-axes are illustrated in FIG. 1 as intersecting at a common point centrally located within tissue mass 26, this is not required. For example, it may be desirable to offset the X and Y-axes somewhat, as measured along the Z-axis. Furthermore, in some cases it may be desirable to define tissue volume 22 with markers 30 in only two dimensions or in only one dimension.

Figure 1A:
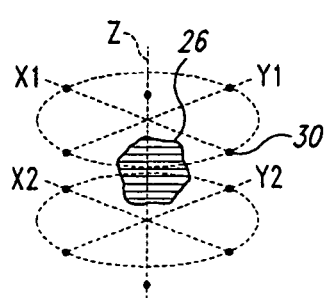
FIG. 1A is an isometric view of the tissue mass illustrated in FIG. 1, with two markers being positioned on opposite ends of each of mutually orthogonal X1, Y1 and Z-axes and with two markers being positioned on opposite ends of mutually orthogonal X2 and Y2-axes which are mutually orthogonal with respect to the Z-axis and offset along with Z-axis with respect to the X1 and Y1-axes.
Figure 1B:
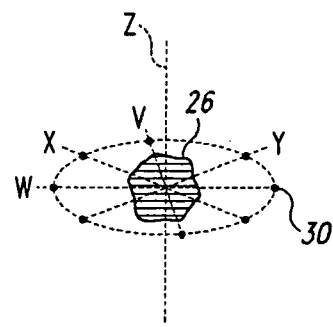
FIG. 1B is an isometric view of the tissue volume illustrated in FIG. 1, with two markers being positioned on opposite ends of each of V, W, X and Y-axes, all of which lie in a common plane and are mutually orthogonal with respect to a Z-axis, all of these axes intersecting the tissue mass.

In some cases, it will be desirable to use more than two markers 30 on X, Y and Z-axes. Referring to FIG. 1A, in a first case, ten markers 30 are used, two on the Z-axis, two on an axis $X_1$, two on an axis $X_2$ that is offset along the Z-axis with respect to axis $X_1$, two on an axis $Y_1$, and two on an axis $Y_2$ that is offset along the Z-axis with respect to axis $Y_1$. Referring to FIG. 1B, in a second case, ten markers 30 are used, two on the X-axis, two on the Y-axis, two on the Z-axis, two on the V-axis which bisects the X and Y-axes and two on the W-axis which also bisects the X and Y-axes, but at a different location. Other numbers and relative placements of markers are also encompassed by the present invention.

Markers 30 are preferably spaced from tissue mass 26 so as to define tissue volume 22 such that tissue margin 28 is large enough to ensure none of the tissue mass of interest lies outside the tissue volume. This precise spacing will vary with the nature of the tissue mass 26, the size of the tissue mass, surgeon preference and other factors. However, tissue margin 28, as measured outwardly along an axis extending perpendicular to a surface location on tissue mass 26, is generally about 0.5 cm to 3 cm, and is preferably about 1 cm to 2 cm. It will be appreciated that other margins may be more appropriate in other circumstances.

Markers 30 may be implanted in tissue portion 24 in a variety of different ways using a variety of different tools. In general, markers 30 are implanted using a conventional imaging system (not shown) that simultaneously generates an image of tissue mass 26 and the markers. By frequently comparing the location of markers 30 to tissue mass 26 during implantation of the markers into tissue portion 24, based on image information received from the imaging system, the markers may be positioned so as to define tissue volume 22 in the manner described above. As noted above, markers 30 are made from a material that provides good image contrast with respect to the imaging energy used. In other aspects of the invention, only one or two markers may be implanted in or proximate to the tissue mass 26, and the margin 28 can be defined on a display by a virtual line or shape based upon the relative location between at least one of the implanted markers and the tissue mass 26.

It is preferable to at least partially immobilize tissue portion 24 during implantation of markers 30. However, this is not necessary because, by comparing the relative location of a marker 30 to tissue mass 26, the desired relative placement can typically be achieved even if tissue portion 24 is moving during marker implantation.

E. Marker Implantation

Various techniques may be used to implant markers 30 in tissue portion 24. With reference to FIGS. 12 and 13, one approach is to insert markers 30 percutaneously through skin 402 overlying tissue portion 24 using known needle pushers or implanters (neither shown) of the type used to implant "seeds" of radioactive material for various cancer treatments. For example, needle pushers of the type sold by Best Industries of Springfield, Va., may be satisfactorily employed. These needle pushers include a central needle surrounded by an outer tube having an end plate or cup for supporting the radioactive "seed." Following insertion of the needle pusher into the selected tissue mass, the radioactive "seed" is released by pressing the central needle downwardly relative to the surrounding outer tube, with the point of the needle ejecting the "seed" from the end plate or cup of the outer tube.

To percutaneously insert marker 30 in accordance with this first approach, the marker is positioned on the end of the needle pusher (in place of the radioactive "seed"), is forced through skin 402 and, using feedback from the imaging system, is guided to the region where it is desired to implant the marker. Then the marker 30 is ejected from the needle pusher by urging the central needle forwardly into the inner tube.

A second approach for implanting markers 30 involves creating a small, e.g., 5-10 mm, incision (not shown) in the skin 402 overlying tissue portion 24. Next, a scalpel is inserted through the incision so as to form a slit in the underlying tissue portion extending to the position where it is desired to implant a maker 30. Then a marker 30 is inserted through the slit to such position using a tweezers, needle pusher, trocar or other suitable tool. Other markers 30 are implanted through separate incisions in skin 402 in similar manner so as to bracket tissue volume 22.

Figure 14:
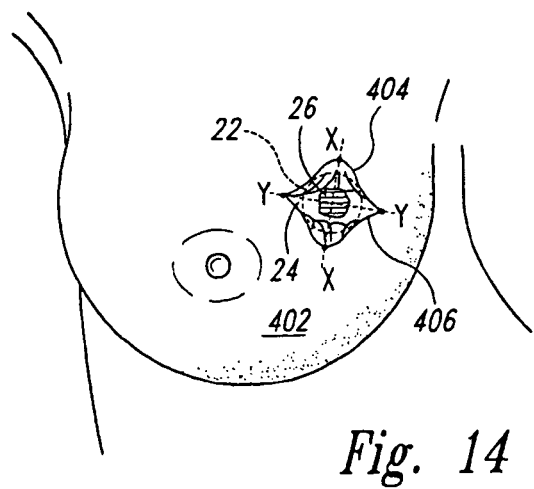
FIG. 14 is similar to FIG. 12, except that the skin adjacent the incision has been pulled apart to provide access to underlying breast tissue.

Referring now to FIGS. 1 and 12-14, a third approach for implanting markers 30 is to form a relatively large, e.g., 1-3 cm, incision 404 (see FIG. 12) in skin 402 overlying tissue mass 26. Next, incision 404 is pulled open as illustrated in FIG. 14 using retractors or other conventional devices to form a relatively large open region 406 above tissue mass 26. Markers 30 are then implanted into tissue portion 24 using either the first or second approaches described above. Other approaches for implanting markers 30 so as to bracket tissue mass 26 are also encompassed by the present invention. The speed and accuracy with which markers 30 may be implanted, and the trauma associated with implantation should be considered in selecting other approaches for implanting markers 30.

F. Marker Identification

Once tissue mass 26 has been bracketed or otherwise marked, tissue volume 22 can be removed. As described in more detail below, one procedure involves identifying the boundaries of tissue volume 22 using an embodiment of probe 32 and detector 34 that is appropriate for the type of marker 30 used, as discussed above. Using information from detector 34 regarding such boundaries, tissue volume 22 is then removed using a scalpel or other tool, with tissue anchor 300 preferably, but not necessarily, being used to stabilize the tissue volume during removal. Another procedure is similar to the first, except that tissue anchor 300 is not used.

For both of these procedures, as the first step the surgeon typically identifies the boundaries of the tissue volume using system 20 or otherwise marks the location of the tissue mass 26 as described in more detail below. This step is generally needed because in practice markers 30 will often be implanted by another doctor, e.g., a radiologist, as a separate procedure. The boundaries of tissue volume 22 are identified by moving probe 32 in the general region of the tissue volume and then monitoring the detection information (e.g., sound, light, dial movement, image clarity and the like) provided by detector 34. As noted above, detector 34 may provide this information when probe 32 is moved within a predetermined proximity of a given marker 30, or may provide this information in a form that changes with changes in proximity of the probe to the marker (e.g., a light gets brighter as the probe is moved toward a marker and dimmer as it is moved away).

The interaction between marker 30 and probe 32 and detector 34 depends upon the detection characteristic of the marker. In the case of marker 30a, which emits gamma radiation 40 (FIG. 2a) on a continuous basis, a probe and detector of the type described in U.S. Pat. Nos. 5,170,055 and 5,246,005 to Carroll et al. (the "C-TRAK probe"), as discussed above, may be satisfactorily used to detect the markers. The C-TRAK probe includes a radiation detector, e.g., a scintillation crystal, which provides an output signal that is believed to vary as a function of the flux density of the gamma rays 40 emitted by marker 30a. Changes in this output signal are then converted into humanly recognizable detection information, e.g., sound, having a characteristic, e.g., pitch or tempo in the case of sound, that varies with changes in gamma ray flux density. By observing the location of probe 32 when the detection information from detector 34 indicates the probe is closest to a given marker 30a, the surgeon can mentally note where the marker is located. Repetition of this process will result in identification of the location of all markers 30a.

Referring to FIGS. 2b and 7, in the case of marker 30b, which generates a magnetic field 42, probe 32' and detector 34' are used to detect the marker. To locate a marker 30b, the surgeon moves probe 32' in the general region of tissue volume 22, with the result that as the probe approaches a given marker 30b its Hall effect sensor (not shown) generates an output signal having a voltage that increases as the probe is moved toward the marker. Similarly the voltage of the output signal decreases as probe 32' is moved away from the marker 30b. The output signal of probe 32' is provided via line 120 to amplifier 122, which amplifies the output signal from the probe. As discussed above, the amplified voltage signal from probe 32' is displayed on signal meter 126 and is also delivered to voltage controlled oscillator 128. The latter generates an oscillating signal, the frequency of which varies as a function of the voltage of the amplified signal provided to voltage controlled oscillator 128. This signal is then amplified by amplifier 130, and the amplified signal then drives speaker 116 such that the pitch of the sound provided by the speaker 116 varies as a function of proximity of probe 32' to marker 30b. By observing signal meter 126 and/or listening to speaker 116, the surgeon can assess when the probe 32' is positioned closest to a selected marker 30b. Repetition of this process will result in identification of the location of all of markers 30b.

Turning now to FIGS. 2c, 3a, 3b and 8, marker 30c, which generates an RF signal 44, is identified using probe 32" and detector 34" in the following manner. RF exciter 60 is operated so as to produce an RF exciter signal 46. More particularly, radio frequency generator 62 (FIG. 3B) generates a radio frequency signal which is amplified by RF amplifier 64, following sensitivity adjustment using gain adjustment 66, with the amplified signal being provided to antenna 68 for transmission to markers 30c. RF exciter 60 is positioned sufficiently close to markers 30c that RF exciter signal 46 is received by antenna 52 of the markers and is of sufficient strength to drive radio frequency generator 56 of the markers. Following detection and regulation by circuit 54 (FIG. 3A) of the signal 46 received by antenna 52, radio frequency generator 56 generates an RF signal which is transmitted by antenna 52 as RF signal 44. Each marker 30c can transmit RF signal 44 at a frequency that is unique to the marker, while an RF exciter signal 46 having a single frequency can be used for all of the markers 30c, with the frequency of signal 46 being different than the frequencies of signals 44.

Once exciter 60 has been activated so as to cause marker 30c to generate RF signal 44, detection of the marker commences. This is achieved by positioning probe 32" (FIG. 8) on or adjacent skin 402 adjacent tissue volume 22, and then monitoring proximity information provided by analog signal strength display 150 and/or speaker 116 of detector 34". More specifically, following receipt of RF signal 44 by receive antenna 140 of probe 32", the signal is filtered by selectable notch filter 142 of probe 32". By correlating a given marker 30c, e.g., marker $30c_1$, with a corresponding representation on the adjustment knob (not shown) that controls selectable notch filter 142, e.g., the reference number "1," the surgeon can identify the location of the given marker. The knob for adjusting selectable notch filter 142 is then moved to a different position when detecting a second marker 30c, e.g., marker $30c_2$.

Signals from receive antenna 140 that are passed through selectable notch filter 142 are then amplified by RF amplifier 144 with the adjustment of the amplifier gain being provided as needed using gain adjustment 146. The amplified signal is then provided to rectifier/integrator 148 where the signal is rectified and time filtered. The strength of signal 144 detected by detector 34" is then displayed via analog signal strength display 150 and is provided to voltage controlled oscillator 152. The latter creates an oscillating signal, the frequency of which varies as a function of the voltage of the signal provided by rectifier/integrator 148. The output signal from voltage controlled oscillator 152 is then amplified by audio amplifier 154 and delivered to drive speaker 116. The pitch of the sound provided by speaker 116 will vary as a function of the frequency of the signal provided by voltage controlled oscillator 152, and as an ultimate function of the proximity of probe 32" to a given marker 30c. By observing the location of probe 32" when the detection information from detector 34" indicates the probe is closest to a given marker 30c, the surgeon can mentally note where the marker is located. By repeating this process for each of the markers 30c with appropriate adjustment of selectable notch filter 142, all of the markers 30c may be located.

Referring to FIGS. 2d, 3a, 3b and 8, marker 30d may also be detected using detector 34" in substantially the same manner discussed above with respect to marker 30c. One significant difference, however, is the fact that RF exciter 60 (FIG. 3B) is not used insofar as marker 30d contains its own power source.

Turning next to FIGS. 2e, 2f, and 4-6, for markers 30e and 30f, which are designed to provide high image contrast when imaged with ultrasound, probe 32 includes a conventional ultrasound transducer (not shown) that generates ultrasound in a conventional frequency range, e.g., 7.5 MHz, and receives back reflection of the ultrasound signal. Detector 34 is the image processor and display (neither shown) of a conventional ultrasound apparatus which is connected to the ultrasound transducer. Markers 30e or 30f are identified by scanning the general region of tissue volume 22 with probe 32, and monitoring the ultrasound image of the markers provided by detector 34. This ultrasound image permits the surgeon to identify the placement of all of the markers, and hence the boundaries of tissue volume 22.

In the case of marker 30e, the latter is caused to vibrate at a frequency that is generally significantly less than that of the ultrasound generated by the ultrasound transducer in probe 32. This creates, through what is believed to be a Doppler shift phenomenon, enhanced image contrast in the ultrasound signal reflected off markers 30e. Vibration of a marker 30e is effected by operating RF exciter 92 so that radio frequency generator 94 generates a radio frequency signal which is amplified by amp 96 and then transmitted by antenna 100. Antenna 80 of marker 30e receives this RF signal, which is detected and regulated by circuit 84 so as to generate an oscillating electrical signal that is provided to piezoelectric device 86. This signal causes the piezoelectric device 86 to mechanically oscillate, which oscillations are transferred via support 88 to outer housing 90 of marker 30e, thereby causing the housing (and hence the marker) to vibrate.

G. Tissue Removal

Following identification of tissue volume 22 using the procedures outlined above, surgical removal of the tissue volume commences. Referring to FIGS. 12 and 14, the first of the two procedures for removing tissue volume 22 referenced above commences with the formation of an incision 404 (FIG. 12) in skin 402 above tissue volume 22. The length of incision 404 is typically about equal to, or slightly greater than, the distance between two markers 30 lying on a given axis, e.g., the Y-axis as illustrated in FIG. 12. Next, portions of skin 402 adjacent incision 404 are pulled apart by retractors or other known devices, so as to form open region 406 (FIG. 14) and expose tissue portion 24 beneath.

Figure 15:
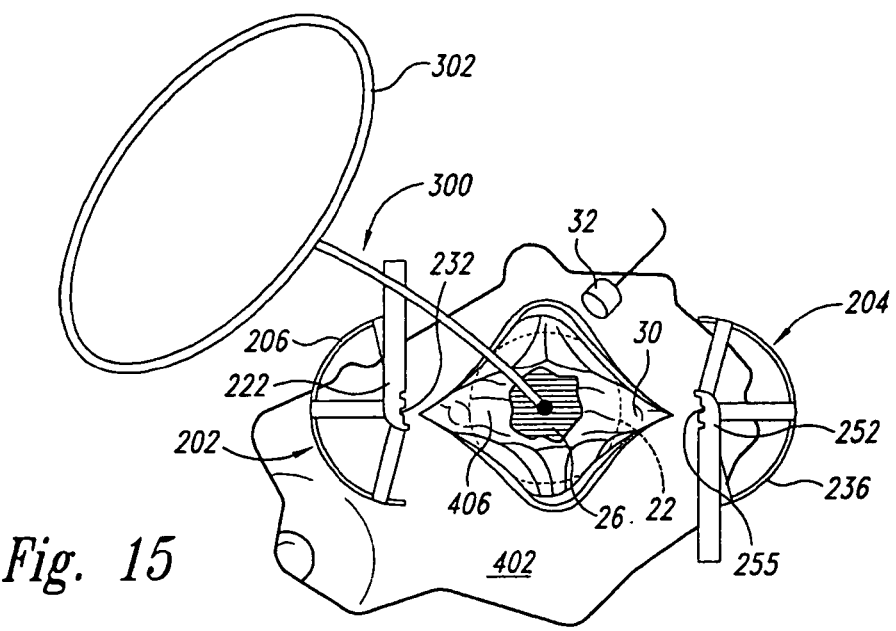
FIG. 15 is an enlarged view of the incision of FIG. 14, with the tissue anchor illustrated in FIGS. 9-11 being positioned in the tissue mass, and the two portions of a cutter illustrated being positioned adjacent the surgical cavity.
Figure 16:
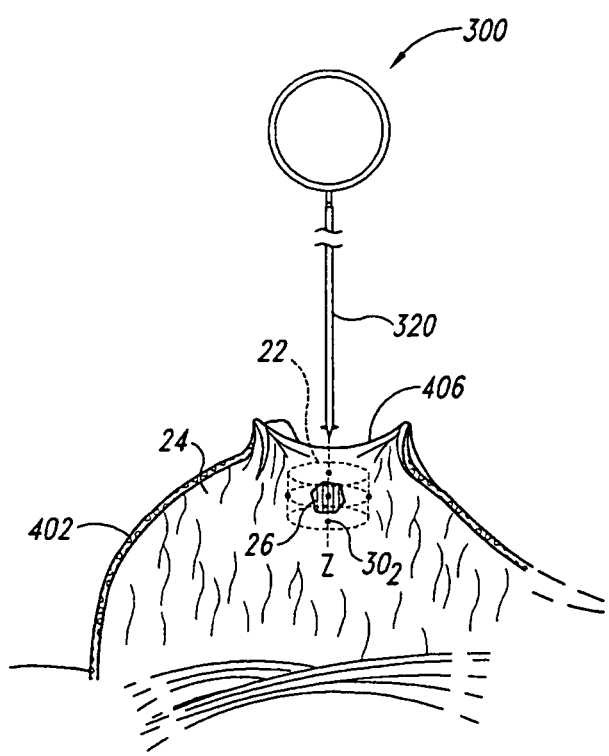
FIG. 16 is similar to FIG. 13, except that an incision has been formed in the skin of the breast and retracted to provide access to the underlying tissue mass to be removed and the tissue anchor has been positioned above the breast.
Figure 17:
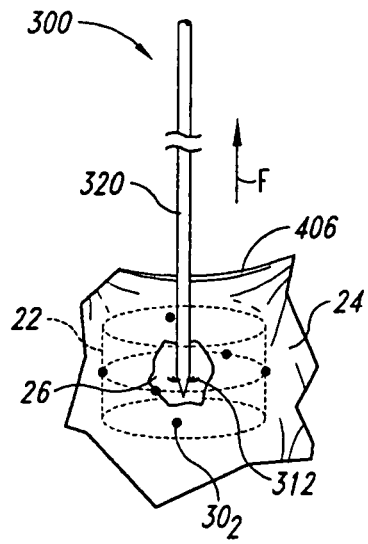
FIG. 17 is an enlarged view of the portion of the breast illustrated in FIG. 16 containing the tissue mass to be removed, with the tissue anchor being positioned in the tissue mass in the extended position so that the anchor members of the tissue anchor engage the tissue mass.

Referring now to FIGS. 9-11 and 15-17, as the next step, tissue anchor 300 is inserted in tissue mass 26 so as to assume the extended position illustrated in FIG. 11. This is achieved by inserting a finger into ring 302, then pulling rod 304 upwardly (as illustrated in FIG. 10) with respect to cannula 320 so that pin 308 moves in slot 328 toward the end thereof closest to proximal end 324 of the cannula. In this retracted position, cannula 320 is grasped and is inserted through open region 406 into tissue volume 22 so that its distal end 326 is positioned substantially in the center of tissue mass 26. This placement may be achieved under the guidance of an imaging system (not shown) that is capable of imaging tissue anchor 300, e.g., ultrasound or X-ray imaging systems. Alternatively, using system 20, the location a marker 302 lying beneath tissue volume 22, as illustrated in FIGS. 16 and 17, is identified using the procedure described above to identify the tissue volume. By identifying the depth at which marker 302 is located and comparing this to the length of cannula 320 inserted into tissue volume 22, distal end 326 may be positioned centrally within tissue mass 26.

Next, ring 302, and hence rod 304 attached thereto, is forced downwardly (as viewed in FIG. 15) relative to cannula 320 until pin 308 contacts the end of slot 328 closest to distal end 326. As rod 304 moves within cannula 320 toward this extended position, anchor members 310 are forced out through apertures 330 and into tissue mass 26 (see FIG. 17). Then, ring 302, and hence rod 304, is rotated slightly so as to cause pin 308 to move into pocket 329.

Figure 18:
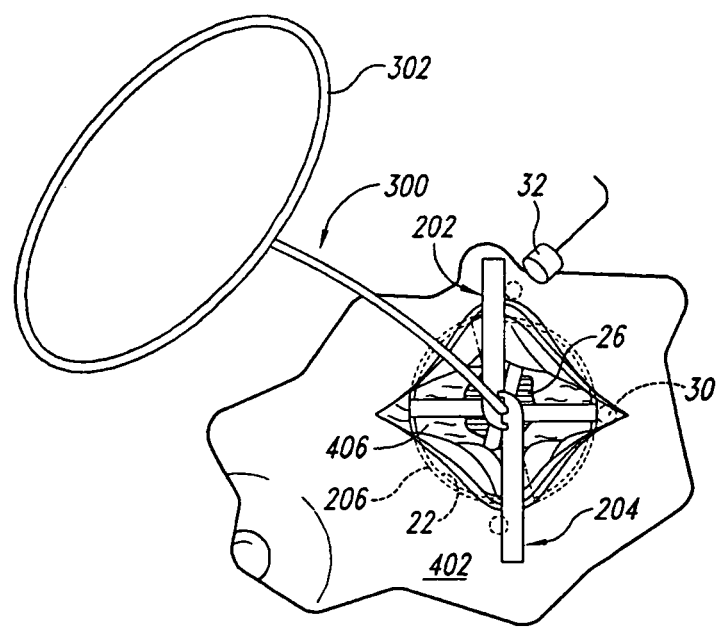
FIG. 18 is similar to FIG. 15, except that two portions of a cutter are illustrated in engaged, cooperative relationship and are positioned under the skin in contact with the tissue volume to be removed.

The next step in the removal of tissue volume 22 is assembly and placement of a cutter 200 in open region 406. Referring to FIGS. 15 and 18-20, the cutter 200 includes cutter portions 202 and 204 that can be positioned adjacent open region 406, as illustrated in FIG. 15. Next, the cutter portion 202 is positioned in open region 406, and a curved plate 206 of the cutter portion 202 is inserted under portions of skin 402 adjacent the open region, as illustrated in FIG. 18. Next, the cutter portion 204 is similarly positioned in open region 406. Then, cutter portions 202 and 204 are moved toward one another so that cannula 320 of tissue anchor 300 is received in an elongate groove 232 in a central handle section 222 and in an elongate groove 255 in a central handle section 252. Cutter portions 202 and 204 are moved even closer to one another so that central handle sections 222 and 252 engage one another. When positioned in this manner, ends of curved portion 206 of cutter portion 202 engage ends of curved portion 236 of cutter portion 204 so as to form a substantially continuous curved cutting edge. Also when positioned in this manner, a longitudinal axis of cutter 200 extends substantially parallel to the elongate axis of cannula 320, both of which are substantially co-axial with the Z-axis extending through tissue volume 22. (See FIGS. 16 and 19).

Figure 19:
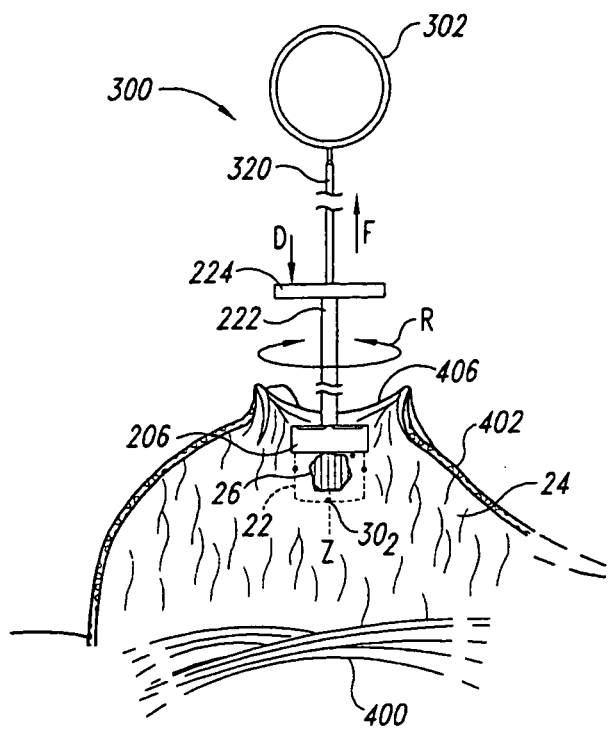
FIG. 19 is similar to FIG. 16, except that the tissue cutter is illustrated surrounding the tissue anchor and in cutting engagement with the tissue volume to be removed.

Next, the position of cutter 200 relative to markers 30 is determined by comparing the location of markers, which is typically determined by using probe 32 and detector 34 in the manner described above, to the position of the cutter. Then, the location of cutter 200 is adjusted so that the longitudinal axis of cutter 200 is substantially co-axial with the Z-axis of the tissue volume 22, as illustrated in FIG. 19. In some cases the surgeon will recall the location of markers 30 from the prior marker identification step, and so it will be unnecessary to again locate the markers. However, when tissue portion 24 is amorphous and pliable, as is the case when breast tissue is involved, it is recommended that this alignment of cutter 200 with tissue portions 30 using probe 32 and detector 34 be performed before any cutting of tissue volume 22 commences.

In connection with the initial insertion of cutter 200 in open portion 406, an appropriately sized cutter 200 is selected such that the radius of curved plates 206 and 236, as measured radially outwardly from the longitudinal axis, is substantially the same as the radius of tissue volume 22 as measured radially outward from the Z-axis. While this relationship between the radii of curved plates 206 and 236 of cutter 200 and the radius of tissue volume 22, as measured with respect to Z-axis, is preferred, in some cases it may be satisfactory to use a cutter having a radius that is greater than or less than the radius of the tissue volume 22. Also, the height of curved portions 206 and 236 is another factor considered in selecting an appropriate cutter 200.

Referring to FIGS. 16-20, as the next step in the removal of tissue volume 22, ring 302 of tissue anchor 300 is typically pulled upwardly in the direction of arrow F (see FIGS. 17 and 19) sufficiently to tension tissue volume 22 and adjacent portions of tissue portion 24. By this tensioning of tissue volume 22 and tissue portion 24 the tendency of the tissue portion to compress under the force of a cutting device is reduced. Also, this tensioning of tissue volume 22 serves to stabilize the tissue volume during the surgical removal process.

In some cases, sufficient tissue stabilization can be achieved merely by holding tissue anchor 300 in a substantially fixed position relative to tissue volume 22. In other words, no force in the direction of arrow F is applied to tissue anchor 300 except as may be necessary to hold the tissue anchor in a stable position.

Figure 21:
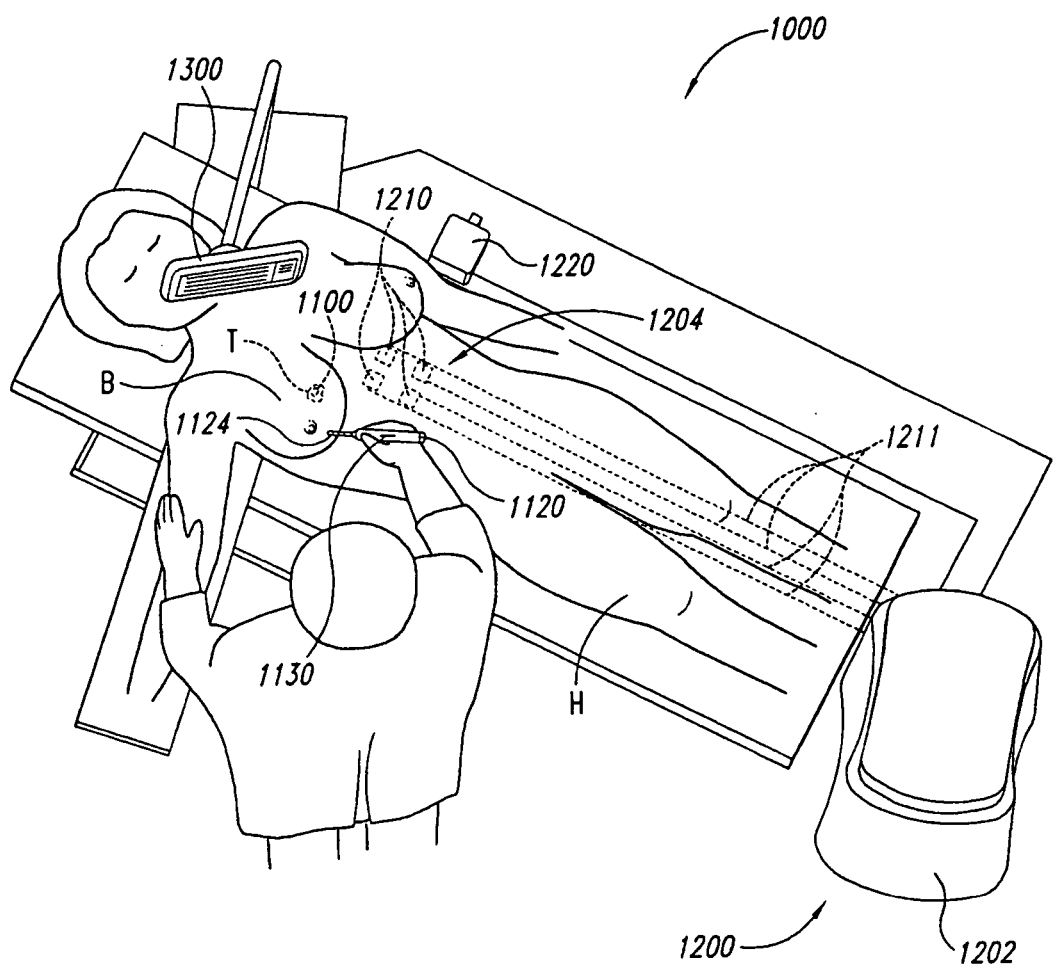
FIG. 21 is an isometric view of a system for locating and defining a target location within a human body in accordance with an embodiment of the invention.

Then, while stabilizing tissue volume 22 with tissue anchor 300, preferably, but not necessarily by maintaining an upward force on the tissue anchor, the surgeon grips cutter 200 and begins pressing downwardly toward tissue volume 22, i.e., in the direction of arrow D (see FIG. 21). At the same time, the cutter is rotated about its longitudinal axis in either or both a clockwise and counterclockwise direction, e.g., in the direction indicated by curved arrow R (see FIG. 19). The elongate grooves 232 and 255 (FIG. 15) are sized to permit cutter 200 to rotate relatively freely about cannula 320 positioned therein.

As cutter 200 is rotated about its longitudinal axis and is urged downwardly towards tissue volume 22, it cuts tissue volume 22 along its outer boundary. Progress in removing tissue volume 22 is generally periodically determined by comparing the position of curved plates 206 and 236 of cutter 200 relative to markers 30 using probe 32 and detector 34 to identify the locations of markers 30 and then comparing such locations with the location of the cutter. In particular, a determination can be made as to when tissue volume 22 has been severed from tissue portion 24 to a depth defined by marker 302 (FIG. 21) defining the bottom or innermost portion of the tissue volume. Thus, by iteratively comparing the position of cutter 200 to the locations of markers 30 using marker location information acquired from detector 34 based on proximity information provided by the detector, a surgeon can determine when the cutting operation is completed and cutter 200 can be removed from tissue portion 24, as indicated in FIG. 20.

Figure 20:
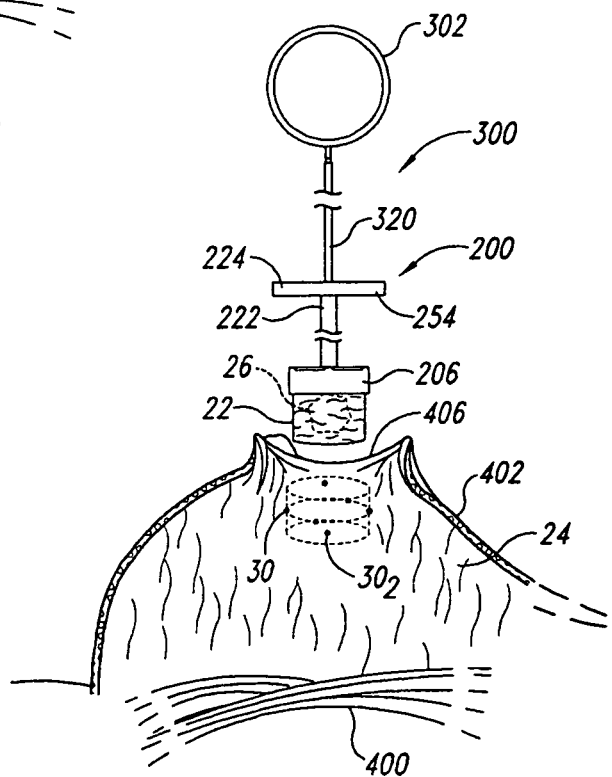
FIG. 20 is similar to FIG. 19, except that the tissue volume has been completely removed from the breast and is illustrated immediately above the surgical opening in engagement with the tissue anchor and cutter.

Depending upon the size of cutter 200 relative to the placement of markers 30, the latter may remain in place in tissue portion 24 following removal of tissue volume 22, as indicated in FIG. 20. If such as the case, markers 30 are then subsequently removed by first locating the markers using probe 32 and detector 34 and then removing the markers with a suitable instrument, e.g., tweezers. In other cases, the markers will be included in the tissue volume 22.

In some cases, it will be necessary to sever the bottom or innermost portion of tissue volume 22 from tissue portion 24 so as to permit removal of the tissue volume. A scalpel or other conventional tool may be used to perform this final severing of the tissue volume. The precise location where this final incision is made may be determined by again locating the position of marker 302 using probe 32 and detector 34. By leaning tissue anchor 300 and cutter 200 to one side, a surgeon can typically follow the incision created by cutter 200 with a scalpel or other tool down to the region where marker 302 is located and tissue volume 22 remains attached to tissue portion 24.

As noted above, in some circumstances a marker 302 is not required when the bottom or innermost portion of tissue volume 22 is positioned immediately above a different type of tissue, e.g., a pectoral muscle 400. In such case, the surgeon can assess when cutter 200 has been inserted sufficiently deep into tissue portion 24 by merely observing when bottom cutting edges of the cutter are about to engage the different type of tissue.

Referring to FIG. 1A, by inserting markers 30 at staggered locations along the Z-axis, the relative depth of cutter 200 in tissue portion 24 can be determined by locating specific markers using probe 32 and detector 34. The location of such markers 30 is then compared with the location of cutter 200 to determine the depth of the cut. For example, if markers 30c are installed at positions $X_1$ and $X_2$ in FIG. 1a, and each marker has a unique frequency, these markers can be uniquely identified by detector 34" (FIG. 8) in the manner described above.

Referring to FIG. 1B, by positioning more than four markers, e.g., eight markers as illustrated in FIG. 1B, the boundaries of tissue volume 22 can often be more readily defined during the removal of the tissue volume. This is so because increasing the number of markers 30 used increases the quantity of information received from detector 34 regarding the boundaries of tissue volume 22.

While the use of cutter 200 in connection with the removal tissue volume 22 often expedites removal of the tissue volume, many other cutters or instruments can be used to remove, treat, monitor, or otherwise perform some procedure on the tissue volume. In this regard, a conventional scalpel may often be satisfactorily employed in place of cutter 200. Also, under certain circumstances it may be desirable to initiate an incision with cutter 200, and then complete the incision with a scalpel. It will be appreciated that other types of cutters and systems for manipulating the tissue can be used, such as using as vacuum to pull-up on the tissue, extending an "umbrella" at the end of a stabilizer to pull-up on the tissue, vibrating the cutter to cut the tissue (either in lieu of or in addition to rotating the cutter), and using rotational electrocautery.

The process of removing tissue volume 22 using a scalpel also preferably commences by inserting tissue anchor 300 in tissue volume 22 in the manner described above. The location of markers 30 are also determined prior to and during the removal of tissue volume 22 by scalpel in the manner described above. Thus, during the removal of tissue volume 22, the boundaries thereof may be repeatedly identified by locating markers 30 using probe 32 and detector 34. As noted above, it is generally advantageous to use tissue anchor 300 when removing tissue volume 22 with a scalpel because by stabilizing the tissue volume and surrounding regions of tissue portion 24, it is easier to maintain alignment of the scalpel with the boundaries of the tissue volume. However, it is to be appreciated that the use of tissue anchor 300 is a preferred, but not essential, aspect of the present method of bracketing and removing tissue volume 22.

Referring now to FIG. 2g and FIG. 13, as noted above, probe 32 and detector 34 are not used in connection with marker 30g. The detection characteristic of markers 30g is the release of a colored dye 78 in surgical cavity adjacent the markers. In an alternative embodiment, the markers can be capsules that each have a different color, and the colored markers can be implanted in a manner to define the desired margin for guidance during a percutaneous biopsy procedure, excisional procedures, and other procedures. Removal of a tissue volume 22 bracketed by markers 30g differs from the removal of tissue volume when bracketed by the other embodiments of marker 30 in that the location of marker 30g is not determined by the surgeon prior to initiation of the removal of tissue volume 22. Practically speaking, this is more a difference in the process for removing tissue volume 22 than a difference in the composition and construction of marker 30g. This is so because for implantation purposes, marker 30g must necessarily be imageable by some form of imaging system, which imaging system could, in most cases, also be used by the surgeon to identify the location of marker 30g prior to and in connection with the removal of tissue volume 22. For example, if marker 30g is initially implanted by imaging the marker using an ultrasound system, then marker 30g is actually a marker 30f. Thus, in connection with the following description of the process of removing tissue volume 22 bracketed with markers 30g, it is assumed the markers are not located by the surgeon prior to, or in connection with, the removal of tissue volume other than by visual observation, as discussed below.

Removal of tissue volume 22 bracketed by markers 30g also preferably commences by installing tissue anchor 300 as described above. Again, the use of tissue anchor 300 is preferred, but not mandatory. Next, the surgeon commences cutting the general region of tissue volume 22, which can be defined by colored marks, Kopanz needles or other known techniques. Then, the removal of tissue volume 22 proceeds using either cutter 200, or a scalpel or other cutting device. As this removal of tissue volume 22 is performed, tissue anchor 300, if used, is manipulated to stabilize tissue volume 22 in the manner described above. As cutter 200, the scalpel or other cutting device (e.g., a vacuum assisted cutting device) encounters a marker 30g, the capsule of the marker is severed releasing the colored dye 78. This advises the surgeon that a boundary of tissue volume 22 has been encountered. It may be advantageous to use a given color of dye in markers 30g defining one side of the boundary of tissue volume 22, while the markers 30g defining an opposite side include a different color of dye. By defining the boundary of tissue volume 22 with a sufficient number, e.g., 10-25, of markers 30g, the boundary of tissue volume 22 can typically be identified by iteratively cutting and observing whether dye appears in the surgical cavity.

As noted above, marker embodiments 30a-30f may all include colored dye 78 within an outer capsule that is sufficiently tough to withstand insertion and yet is relatively easily cut by cutter 200, a scalpel or other cutting device. Such use of dye in markers 30 provides another source of information for the surgeon regarding the boundary of tissue volume 22.

One advantage of certain embodiments of the tissue bracketing system 20 is that they permit the relatively precise identification of the boundaries of tissue volume 22 without the need for needles, wires or other cumbersome apparatus projecting from tissue portion 24. As such, bracketing system 20 permits a surgeon to relatively quickly and easily identify the tissue boundary of tissue volume 22 and remove the tissue volume. In addition, system 20 is ideally adapted for bracketing a tissue volume 22 in amorphous, pliable tissue, such as breast tissue.

Another advantage of certain embodiments of the cutter 200 is that they permit a tissue volume 22 of relatively large diameter to be removed through a relatively small incision 404 or percutaneously. This advantage is useful in this era when tissue-conserving therapies are being emphasized.

By stabilizing tissue volume 22 using tissue anchor 300, the accuracy with which a surgeon can remove tissue volume 22 is also enhanced compared to techniques that do not use a tissue stabilizer or anchor. Also, the accuracy of removing tissue may be further enhanced by docking the tissue stabilizer or anchor to the first implanted tissue marker by using a first marker in the tissue stabilizer and the position detection system. This advantage of the present embodiment arises because tensioning of the tissue volume 22 by pulling upwardly on tissue anchor 300 serves to retain the tissue portion in a relatively stable position. Indeed, even holding tissue anchor 300 in a substantially fixed position relative to the tissue volume 22 with which it is engaged typically provides beneficial stabilization of the tissue volume.

While cutter 200 and tissue anchor 300 may be advantageously employed in connection with the present method of bracketing and removing tissue volume 22, it is to be appreciated that the cutter and tissue anchor have application in many other contexts. More specifically, in any application in which it is desired to remove a volume of tissue through as small an incision as possible, cutter 200 has utility. Similarly, when it is desired to stabilize a piece of tissue in connection with surgical removal or other treatment of the piece of tissue, whether or not within the bracketing context of the present invention, tissue anchor 300 also has important application. Likewise, the system of bracketing a tissue mass is also useful in other applications, such as radiation therapy, and in connection with other body parts.

Certain changes may be made in the above apparatus and processes shown in FIGS. 1-20 without departing from the scope of the present invention. As such, it is intended that all matter contained in the preceding description or shown in the accompanying drawings shall be interpreted in an illustrative and not in a limiting sense. For example, as explained below with reference to FIGS. 21-61, additional embodiments in accordance with other aspects of the invention are also useful for locating, monitoring, and or treating tissue masses and other body parts within a human body.

II. Alternate Systems and Methods for Locating, Monitoring and/or Treating Target Locations Within a Human Body

A. Overview of System Components and Operation

FIG. 21 is an isometric view of a system 1000 for locating a target location T within a human body H in accordance with one embodiment of the invention. The target location T shown in FIG. 21 can be a lesion, tumor, or other area of interest on or within a soft tissue region (e.g., a breast "B"), an organ, the colon, a bone structure, or another body part. The particular components of the system 1000 are best understood in light of the relationship between the components and the operation of the system. Therefore, the following description will initially explain an overview of the components and the general operation of the system 1000.

In one embodiment, the system 1000 includes a wireless implantable marker 1100, an instrument 1120, a position detection system 1200, and a user interface 1300. The wireless implantable marker 1100 can be implanted at a precise location with respect to the target location 1000 using stereotactic imaging systems and other procedures known in the art as explained above. In operation, the position detection system 1200 determines the location of the wireless implantable marker 1100 and the location of the instrument 1120 relative to a reference location to determine the relative position between the target location T and the instrument 1120. The position detection system 1200 is coupled to the user interface 1300 to convey the relative position between the target location 1000 and the instrument 1120 in a manner that allows a surgeon to intuitively understand the position and the orientation of the instrument 1120 relative to the target location 1000 without additional imaging equipment. As a result, the system 1000 is particularly useful for applications in which the patient cannot immediately proceed from an imaging procedure to another procedure, or when intraoperative imaging is not practical or economical.

Figure 22:
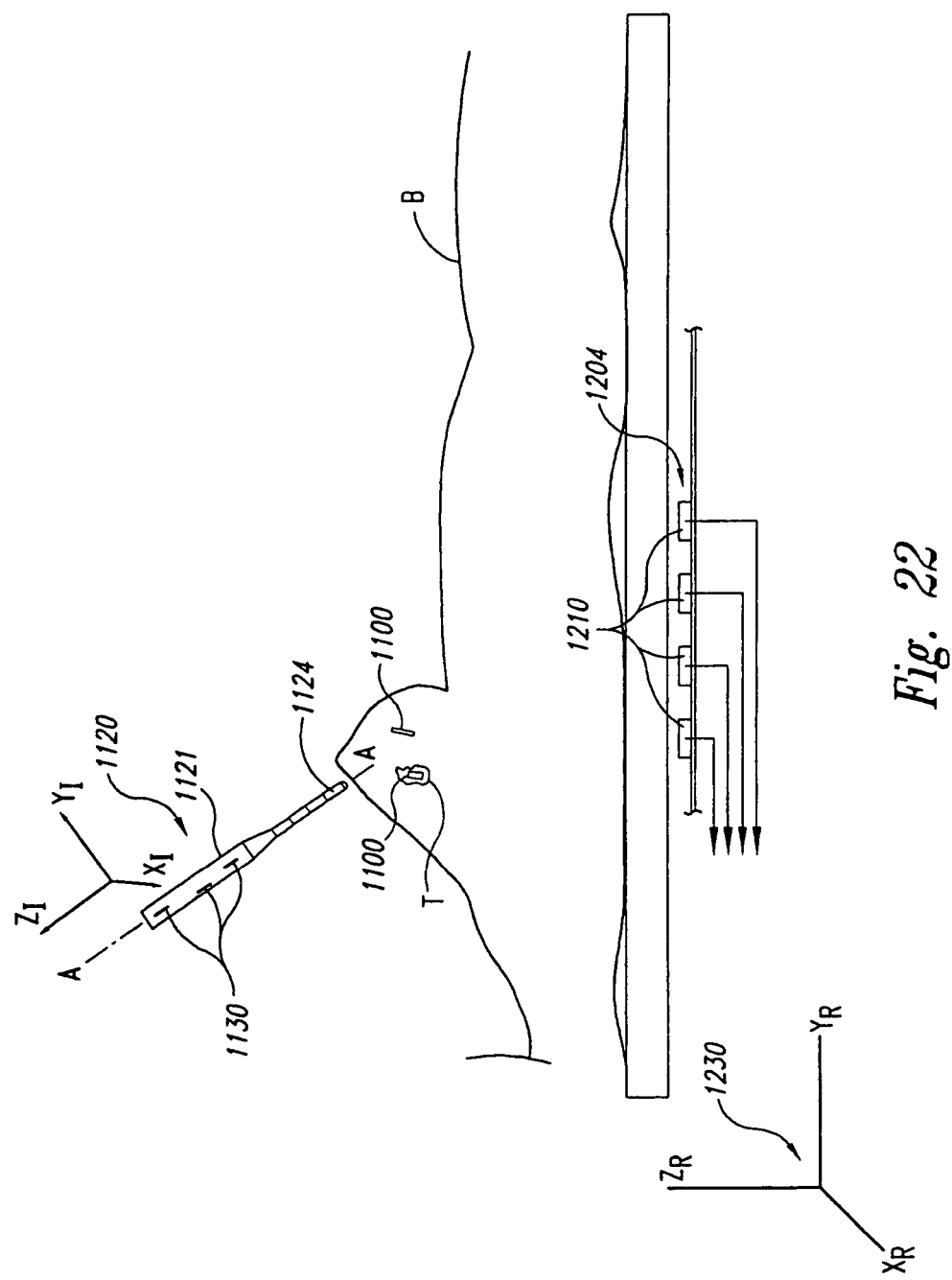
FIG. 22 is a schematic elevation view illustrating a portion of a system for locating and defining a target location within a human body.

FIG. 22 is an elevational view illustrating selected embodiments of the wireless implantable marker 1100, the instrument 1120, and a portion of the position detection system 1200 in greater detail. The wireless implantable marker 1100 can be one of the markers described above with reference to FIGS. 1-20. Alternatively, the wireless implantable marker 1100 can be a resonating marker or another type of marker as described below in more detail with reference to FIGS. 23A-33. In general, at least one wireless implantable marker 1100 is implanted at a location relative to the target location 1000. In the embodiment shown in FIG. 22, one wireless implantable marker 1100 is implanted within the target location T and another wireless implantable marker 1100 is implanted adjacent to the target location T. In several embodiments, the wireless implantable markers 1100 emit a response energy in reaction to an excitation energy emitted by the position detection system 1200. The position detection system 1200 can sense the intensity of the response energy and determine the location of the individual implantable markers 1100 relative to a reference location.

This implementation could be used with a device that is at a known location relative to the position detection system reference location. For example, an external beam radiation could be applied to a target location defined by the first implantable marker or otherwise monitored when the position of the beam applicator is known relative to the reference location of the position detection system. A suitable external beam radiation device is the PRIMIS Linear Accelerator from Siemens Medical of Concord, Calif.

The instrument 1120 can include a handle 1121, a function-site 1124 coupled to the handle 1121, and at least one instrument marker 1130. The function-site 1124 can be a tip of the instrument 1120 or a portion of the instrument 1120 that cuts, ablates, deposits, images or otherwise treats or monitors the target location T. Several embodiments of various types of instruments with different function-sites are described in more detail below with reference to FIGS. 40-52. The instrument markers 1130 can be the same type of wireless markers as the implantable marker 1100, or alternatively the instrument markers 1130 can be a different type of wireless marker. The instrument markers 1130 can also be "wired" markers that are directly coupled to the position detection system 1200. The position detection system 1200 can also gauge the instrument markers 1130 to determine the position of the instrument relative to a reference location.

In the embodiment shown FIG. 22, the instrument 1120 includes three instrument markers 1130 including two instrument markers 1130 that are attached to the instrument 1120 along an alignment axis A-A, and a third instrument marker 1130 that is offset from the alignment axis A-A. By knowing the distance between the function-site 1124 and the array of instrument markers 1130, the position detection system 1200 can determine the position and the orientation of the function-site 1124 based upon the positions of the three instrument markers 1130.

Referring to FIGS. 21 and 22 together, the position detection system 1200 (FIG. 21) can include a processor 1202 (FIG. 21), a detection array 1204 having a plurality of sensors 1210, and a transmitter 1220 (FIG. 21). The transmitter 1220 can emit an excitation energy that causes the implantable markers 1100 to emit a response energy. Each sensor 1210 can include three coils arranged orthogonally around a magnetic core to measure the response energy emitted from the implantable markers 1100 and instrument 1130. The processor 1202 calculates the distance between each sensor 1210 and each of the markers 1100 and 1130 based upon the intensity of the response energy measured by the sensors 1210. The processor 1202 also correlates the distance measurements between each of the markers 1100 and 1130 to determine the individual locations of the markers 1100 and 1130 relative to a reference location 1230 (e.g., a reference coordinate system). Based upon this data, the processor 1202 and/or another processor of the user interface 1300 can determine the relative position between the function-site 1124 of the instrument 1120 and the target location T. Suitable position detection systems 1200 and resonating signal elements that can be adapted for use with the implantable markers 1100 and/or the instrument markers 1130 are available from Polhemus, Inc. of Burlington, Vt.

B. Embodiments of Wireless Markers

Figure 23A:
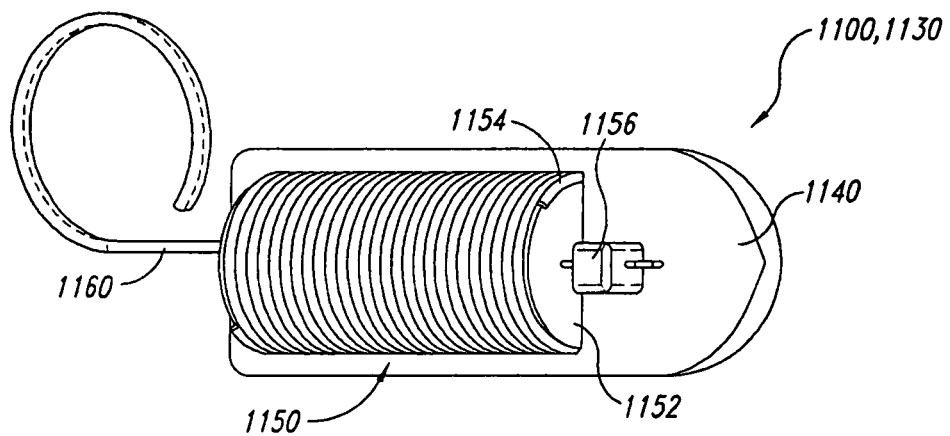
FIGS. 23A-D are isometric cut-away views of wireless resonating markers in accordance with embodiments of the invention.

FIG. 23A is a cut-away isometric view of a resonating marker that can be used for the implantable markers 1100 and/or the instrument markers 1130 in accordance with one embodiment of the invention. In this embodiment, the resonating marker includes a casing 1140 composed of a biocompatible material, a signal element 1150 within the casing 1140, and a fastener 1160. The biocompatible material of the casing 1140 can be a suitable polymeric material, metal, medical grade epoxy, glass, or other compound that can reside within a human body for a period of time. The signal element 1150 can be a resonating circuit that includes a core 1152, a coil 1154 wrapped around the core 1152, and a capacitor 1156 connected to the coil 1154. The core 1152 may be a magnetically permeable material, such as a ferrite. The signal element 1150 emits a response signal in reaction to an excitation energy at the resonate frequency of the circuit. As explained above, the excitation energy can be generated by the transmitter 1220 (FIG. 21) of the position detection system 1200. In other embodiments, the signal element 1150 can be a mechanical resonator (e.g., piezoelectric actuator), an RF emitter, a fluorescent material, a bipolar semiconductor, or another suitable device or material that emits a response signal in reaction to an excitation energy. The fastener 1160 can have several different embodiments. In this particular embodiment, the fastener 1160 is a shape-memory material that is straight in a stored position and coils to form a loop in a deployed position. The shape-memory material can be a spring, or it can be a substance that is straight at room temperature and coils at body temperature.

Figure 23B:
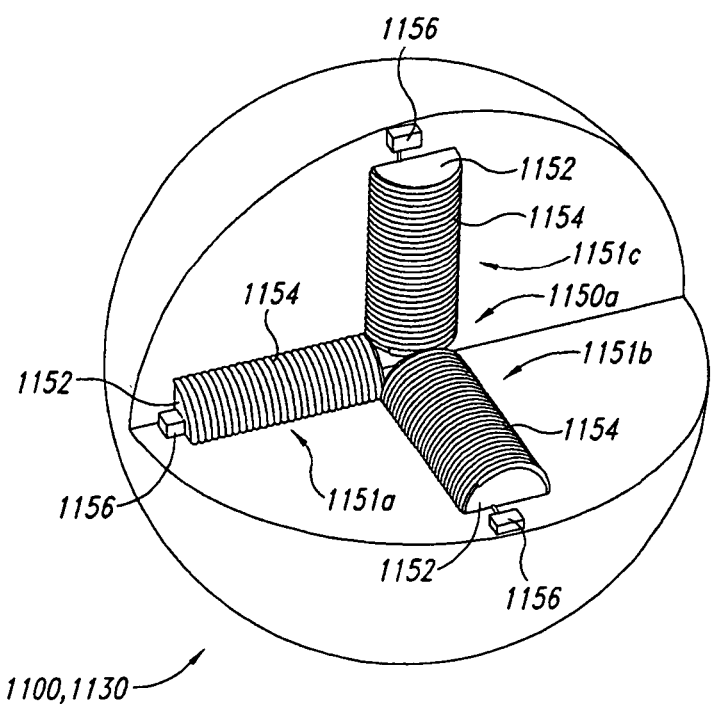

FIG. 23B is an isometric cut-away view of another resonating marker in accordance with an embodiment of the invention. In this embodiment, the resonating marker includes a biocompatible casing 1140 and a signal element 1150a. The marker can also include a fastener (not shown in FIG. 23B). The signal element 1150a has three resonating members 1151a-c arranged orthogonally with respect to each other. The resonating members 1151a-c can also be configured in a non-orthogonal arrangement or any other suitable arrangement. Additionally, the signal element 1150a can include two or more resonating members such that this embodiment of the resonating marker is not limited to having three resonating members 1151a-c. Each resonating member 1151a-c can have a ferrite core 1152, a coil 1154 wrapped around the core 1152, and a capacitor 1156 coupled to each coil 1154. Each resonating member 1151a-c can be tuned to resonate at the same frequency or at different frequencies. When the resonating members 1154a-c resonate at different frequencies, this embodiment of a resonating marker can thus provide three different signals from a single marker so that the position detection system can detect not only the point position of the marker (e.g. an X-Y-Z location), but also the pitch, roll and yaw of the marker relative to a coordinate system.

Figure 23C:
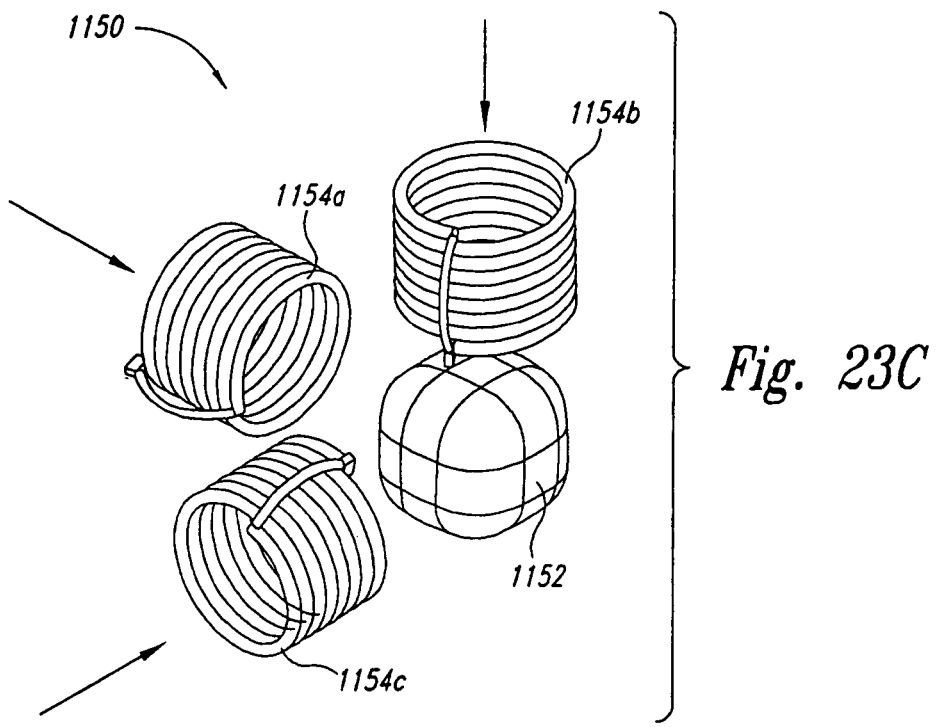
Figure 23D:
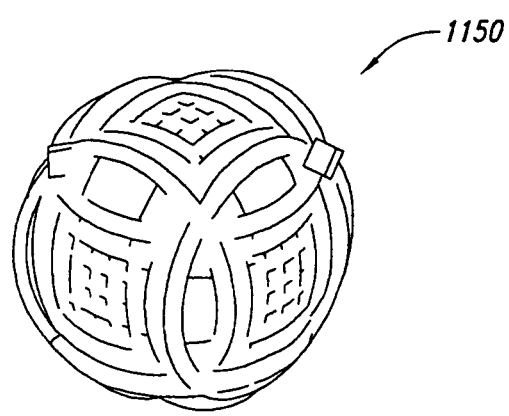
Figure 24:
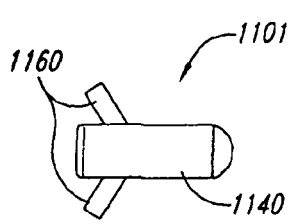
FIGS. 24-30 are side elevation views of several wireless implantable markers in accordance with embodiments of the invention.
Figure 25:
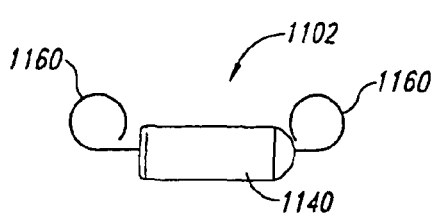

FIGS. 23C and 23D illustrate a resonating marker in accordance with still another embodiment of the invention. In this embodiment, the resonating marker has a single core 1152 and three coils 1154a-c. Each coil 1154a-c can be coupled to a capacitor (not shown), and each coil 1154a-c can generate a different signal. As such, this marker can be located in a manner similar to the marker described above with reference to FIG. 23B. The core 1152 can accordingly be a ferrite block, and the coils 1154a-c can be wrapped around the block orthogonally to each other as shown in FIG. 23D.

The resonating markers shown in FIGS. 23A and 23B are particularly useful because they can remain within a human body for a long period of time. These resonating markers can also have frequencies that are useful in applications in which a plurality of wireless markers 1100 are implanted. In such situations, it may be necessary to distinguish the implanted markers from one another. By using resonating markers that resonate at different frequencies, the position detection system 1200 can identify the "signature" of each marker by its unique frequency. A surgeon, therefore, can easily identify the relative location between a particular implanted marker 1100 and an instrument 1120.

FIGS. 24-30 are side elevation views of several implantable markers 1101-1107 in accordance with embodiments of the invention. Each implantable marker 1101-1107 shown in FIGS. 24-30 has a biocompatible casing 1140. Additionally, the implantable markers 1101-1107 can also include a signal element 1150 or 1150a for emitting a resonating signal, such as a magnetic resonator, a mechanical resonator (e.g., a piezoelectric actuator), an RF emitter, a magnet, a fluorescent material, or other suitable elements that can emit a signal for detection by the position detection system 1200 (FIG. 21).

Figure 26:
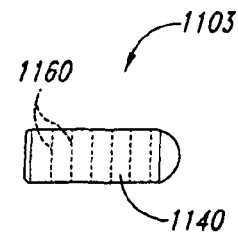
Figure 27:
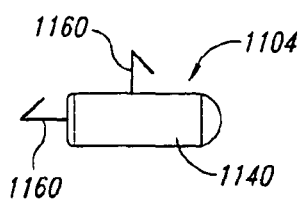
Figure 28:
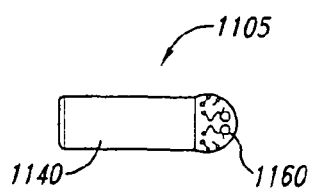
Figure 29:
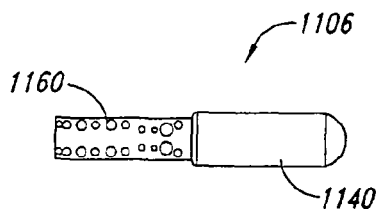
Figure 30:
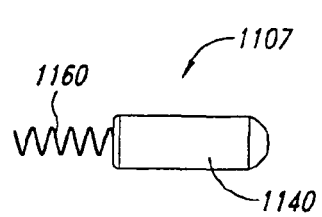

The implantable markers 1101-1107 have different types of fasteners 1160. The implantable marker 1101 shown in FIG. 24 includes a fastener 1160 defined by legs that project away from the casing 1140 in the deployed position. The legs can be molded projections of the casing 1140, or the legs can be small springs that are biased to project away from the casing 1140. The implantable marker 1102 shown in FIG. 25 includes a fastener 1160 defined by shape-memory loops on both ends of the casing 1140. In FIG. 26, the implantable marker 1103 has a fastener 1160 defined by a surface texture, such as scales, that project away from the casing 1140. The surface texture of the implantable marker 1103 can be integrally formed with the casing 1140. Referring to FIG. 27, the implantable marker 1104 can include a fastener 1160 defined by one or more barbs or hooks. Referring to FIGS. 28 and 29, the implantable markers 1105 and 1106 have fasteners 1160 defined by a perforated material through which tissue can grow, such as a mesh. The implantable marker 1105 shown in FIG. 28 has a perforated tip, and the implantable marker 1106 shown in FIG. 29 has a perforated tail. Referring to FIG. 30, the implantable marker 1107 includes a fastener 1160 defined by a spring or a serpentine element extending from the rear of the casing 1140. It will be appreciated that the fasteners 1160 can have different configurations than the particular types of fasteners 1160 shown in FIGS. 24-30.

Figure 31:
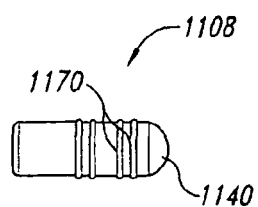
FIGS. 31-33 are side elevation views of several wireless implantable markers in accordance with additional embodiments of the invention.
Figure 32:
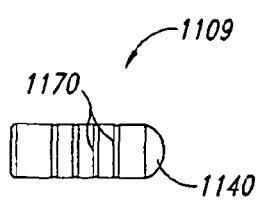
Figure 33:
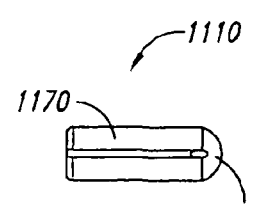

FIGS. 31-33 are side elevation views of several embodiments of implantable markers 1108-1110 in accordance with additional embodiments of the invention. The implantable markers 1108-1110 can include the biocompatible casing 1140 for implantation into a human body. The implantable markers 1108-1110 also include at least one identifier 1170 that is on and/or in the casing 1140. The identifier 1170 can be a radiopaque material that reflects radiation energy, an echogenic material that reflects ultrasound energy, and/or a groove or channel in the casing 1140 that can be observed by an imaging system. Alternatively, the identifiers 1170 can be a color or other marking that is visually distinguishable for viewing with a human eye. The identifiers 1170 provide another feature for distinguishing one marker from another that can be used in addition to, or in lieu of, using signal elements 1150 that emit different frequencies. The implantable markers 1108-1110 can also include fasteners 1160 as described above with reference to FIGS. 24-30, and/or signal elements 1150 or 1150a as described above with reference to FIGS. 23A and 23B.

FIGS. 34 and 35 are isometric views of arrangements for implanting the wireless implantable markers 1100 relative to the target location T in accordance with embodiments of the invention. FIG. 34 illustrates an embodiment in which only a first wireless implantable marker 1100a is implanted in the target location T, and FIG. 35 shows an embodiment in which only the first wireless implantable marker 1100a is implanted adjacent to or otherwise outside of the target location T. In either embodiment, the location of the implantable marker 1100a relative to the target location T is determined when the marker 1100a is implanted or at another imaging procedure so that the marker 1100a provides a reference point for locating the target location T in subsequent procedures. The user interface 1300 can electronically generate a virtual margin 1301 relative to the target location based upon parameters defined by the physician and the location of the implantable marker 1100a. In other embodiments, it is not necessary to generate the virtual margin 1301 relative to the target location T. The physician can determine the shape of the virtual margin 1301 so that it defines a boundary for performing a particular procedure at the target location T. The virtual margin 1301 is typically configured so that it defines the desired boundary for the particular procedure at the target location T without unduly affecting adjacent areas. In the case of a lesion in a soft tissue region, for example, the physician can define a virtual margin 1301 that encompasses the lesion and an appropriately sized safety zone around the lesion that mitigates collateral damage to tissue proximate to the lesion. The virtual margin 1301 can be spherical as shown in FIGS. 34 and 35, or it can have any desired shape including rectilinear shapes, oval shapes, or compound shapes.

FIGS. 36-39 are isometric views of additional arrangements for implanting the wireless implantable markers 1100 relative to the target location T in accordance with other embodiments of the invention. FIG. 36 illustrates an embodiment in which six individual implantable markers 1100a-1100f are implanted in pairs along three orthogonal axes to define an excision boundary or another type of margin around the target location T. FIG. 37 shows an embodiment in which two individual implantable markers 1100a and 1100b define a cylindrical margin around the target location T. FIG. 38 illustrates an embodiment in which individual implantable markers 1100a and 1100b define an ovoid margin around the target location T, and FIG. 39 illustrates an embodiment in which four implantable markers 1100a-1100d define a rectilinear margin around the target location T. The individual implantable markers 1100a-1100f can define an actual margin by bracketing the target location T, or the positions of one or more of the individual markers 1100a-1100f can be used to generate a virtual margin 1301 for use with the user interface. Additionally, it will be appreciated that other arrangements for implanting the implantable markers 1100 and other types of margins can be used depending upon the particular procedure, the type of body part, and the shape of the target location T.

C. Embodiments of Instruments

Figure 40:
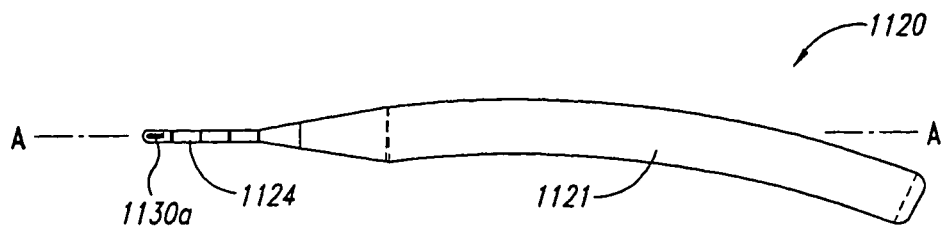
FIGS. 40-43 are side cut-away views of instruments in accordance with embodiments of the invention.
Figure 41:
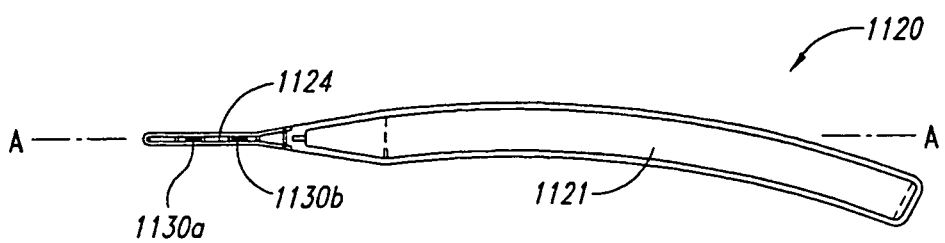
Figure 42:
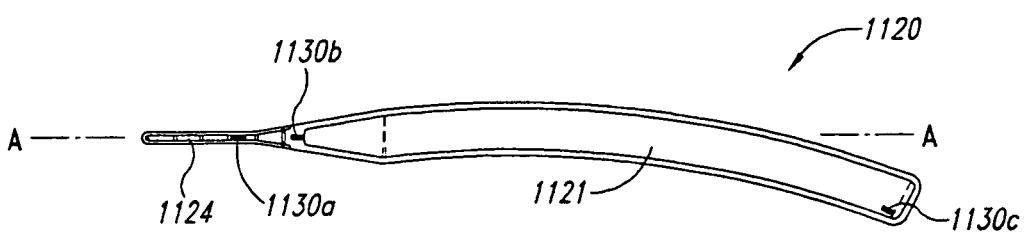

FIGS. 40-42 are cut-away side elevation views of instruments 1120 in accordance with embodiments of the invention. The instruments 1120 include the handle 1121, the function-site 1124 coupled to the handle 1121, and at least one instrument marker 1130. The position detection system 1200 (FIG. 1) can determine the position of the instrument markers 1130 relative to a reference location. Referring to FIG. 40, this embodiment of the instrument 1120 includes a single instrument marker 1130a at a predetermined location relative to the function-site 1124. The embodiment of the instrument 1120 shown in FIG. 40 provides at least a single position point for tracking by the position detection system 1200. When the instrument marker 1130 is a single-axis marker, such as the marker shown in FIG. 23A, the instrument 1120 can be displayed as a single point by the user interface 1300 (FIG. 1). The orientation of this particular embodiment of the instrument 1120 cannot be displayed by the user interface 1300 because the single-axis marker does not provide sufficient data to determine the angle of the alignment axis A-A relative to a plane through the target location T (FIG. 1) or the rotational position of the instrument 1120 around the alignment axis A-A. It may be possible, though, to have a single instrument marker 1130 define the location and orientation of the instrument 1120 if the position detection system 1200 and the instrument marker 1130 are sensitive enough to pinpoint the location and orientation of the single instrument marker 1130. For example, the multiple-axis markers shown in FIGS. 23B-D are expected to provide sufficient data to define the location and orientation of the instrument 1120 using a single marker.

FIG. 41 illustrates another embodiment of the instrument 1120 having a first instrument marker 1130a and a second instrument marker 1130b. The first instrument marker 1130a is positioned at a first predetermined location relative to the function-site 1124, and the second instrument marker 1130b is positioned at a second predetermined location relative to the function-site 1124. The first and second instrument markers 1130a and 1130b can be positioned along the alignment axis A-A as shown in FIG. 41, or at least one of the markers 1130a or 1130b can be offset from the alignment axis A-A. The embodiment of the instrument 1120 shown in FIG. 41 accordingly provides two position points that the position detection system 1200 can track. As a result, the position detection system 1200 can determine the angle of the alignment axis A-A relative to a reference plane so that the user interface 1300 can display the instrument 1120 as (a) a vector of varying length when the alignment axis A-A is not normal to the reference plane, or (b) as a point when the alignment axis A-A is at least approximately normal to the reference plane. When the instrument markers 1130a and 1130b are multiple-axis markers, the rotational orientation of the instrument 1120 relative to the alignment axis A-A can be determined such that both the position of the function-site 1124 and the orientation of the instrument 1120 can be displayed by the user interface 1300.

FIG. 42 illustrates yet another embodiment of the instrument 1120 having a first instrument marker 1130a, a second instrument marker 1130b, and a third instrument marker 1130c. The first and second instrument markers 1130a and 1130b can be positioned along the alignment axis A-A, but the third instrument marker 1130c is offset from the alignment axis A-A. This embodiment of the instrument 1120 provides three position points for tracking by the position detection system 1200. As a result, the position detection system 1200 can determine (a) the angle of the alignment axis A-A relative to a reference plane, and (b) the rotational orientation of the instrument 1120 around the alignment axis A-A. The embodiment of the instrument 1120 shown in FIG. 42 accordingly permits the user interface 1300 to show the angle of the function-site 1124 relative to a reference plane, and the orientation of a leading edge of the function-site 1124 relative to the motion of the instrument 1120.

Figure 43:
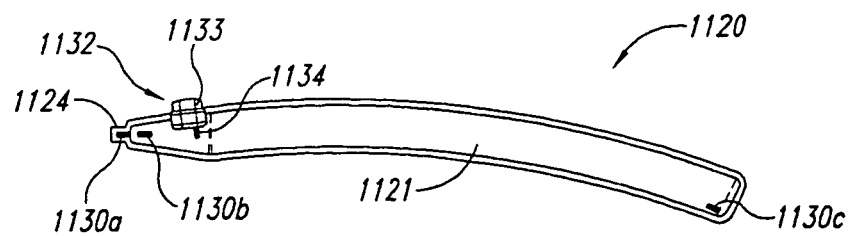

FIG. 43 is a side elevational view of an embodiment of the instrument 1120 including a wireless control 1132 for controlling an aspect of (a) the instrument 1120, (b) the position detection system 1200, and/or (c) the user interface 1300 in accordance with another embodiment of the invention. The instrument 1120 shown in FIG. 43 has three instrument markers 1130a-c, but will be appreciated that the instrument 1120 can have any of one or more instrument markers 1130. The wireless control 1132 includes an actuator 1133 and a transmitter 1134 coupled to the actuator 1133. The transmitter 1134 transmits or otherwise emits a signal indicating a control parameter. The transmitter 1134, for example, can be another marker that the position detection system 1200 can track. In one particular embodiment, the transmitter 1134 is a resonating magnetic marker having a signal element 1150 as set forth above with respect to FIG. 23. One advantage of using a resonating marker for the transmitter 1134 is that the system 1000 (FIG. 21) can be controlled by a wireless instrument 1120 using the position detection system 1200 without additional types of receivers (e.g., RF systems) that add to the complexity and cost of the system 100. Alternatively, the transmitter 1134 can be an RF device, a mechanical resonator, a permanent magnet, or another type of device that emits a frequency or another form of energy. When the transmitter 1134 is a marker, the position detection system 1200 detects the position of the transmitter 1134 and generates a control signal according to the position of the transmitter 1134.

Figure 44:
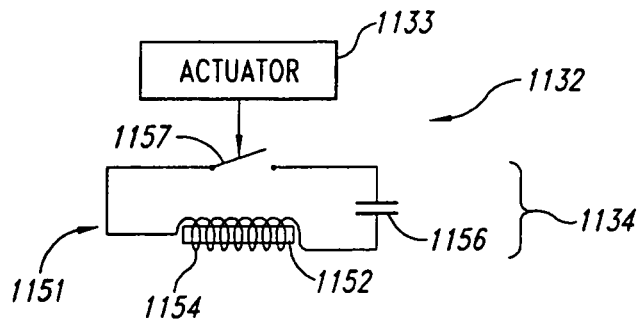
FIGS. 44 and 45 are schematic views of wireless controls for instruments in accordance with embodiments of the invention.

FIG. 44 is a schematic view of one embodiment of the wireless control 1132. In this embodiment, the transmitter 1134 of the wireless control 1132 is a resonating marker having a resonating signal element 1150b similar to one of the signal elements 1150 or 1150a shown above in FIG. 23A or 23B. The signal element 1150b includes a ferrite core 1152, a coil 1154 wrapped around the core 1152, a capacitor 1156 coupled to the coil 1154, and a cut-off switch 1157 between the coil 1154 and the capacitor 1156. The actuator 1133 can be a push-button coupled to the cut-off switch 1157 that breaks the circuit to deactivate the signal element 1150b. In operation, the physician can press the actuator 1133 to close the cut-off switch 1157 so that the signal element 1150b emits a resonating signal. The position detection system 1200 detects the signal from the signal element 1150b and generates a control signal that changes a parameter of the system 1000. The position detection system 1200, for example, can send a message to the user interface 1300 to change a display of the user interface 1300 to show the relative position between the instrument 1120 and one of several implanted markers 1100. This is particularly useful when a plurality of markers 1100 are implanted, such as the implanted markers 1100a-f in FIG. 36, and the physician needs to know the position relative to a particular marker. In one embodiment, the control 1132 can be used to cycle through the various markers 1100a-f by depressing the actuator 1133 to move from one marker to the next. The wireless control 1132 can also have several other applications that allow the position detection system 1200 to control other aspects of the system 1000 based upon input at the instrument 1120.

Figure 45:
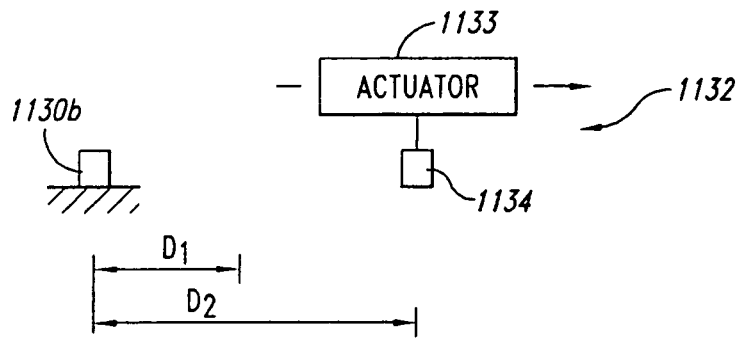

FIG. 45 is a schematic view of another embodiment of the wireless control 1132. In this embodiment, the actuator 1133 is a slider mechanism that moves along the handle 1121, and the transmitter 1134 is another marker that can be detected by the position detection system 1200. The actuator 1133, for example, can be a linear slider or a rotational slider that has "click-stops" to indicate various control positions. In operation, the relative distance between the transmitter 1134 and a fixed marker attached to the instrument (e.g., the second instrument marker 1130b) is determined by the position detection system 1200. A parameter of the instrument 1120, the position detection system 1200, and/or the user interface 1300 can be controlled according to the relative distance between the transmitter 1134 and the fixed marker. For example, if the distance between the transmitter 1134 and the second instrument marker 1130b is $D_1$, the user interface 1300 may display the distance between the function-site 1124 of the instrument 1120 and a first implanted marker. Similarly, if the distance between the transmitter 1134 and the second instrument marker 1130b is $D_2$, the user interface 1300 may display the relative distance between the function-site 1124 and a second implanted marker.

FIGS. 46-52 illustrate several instruments 1120a-g in accordance with various embodiments of the invention. The instruments 1120a-g can each include a handle 1121, a function-site 1124 coupled to the handle 1121, and at least one instrument marker 1130 similar to the instruments 1120 described above with reference to FIGS. 40-42. The instruments 1120a-g can also include a wireless control similar to the wireless controls 1132 described above with reference to FIGS. 43-45. The differences between the instruments 1120a-g is generally the type of function-site 1124.

Figure 46:
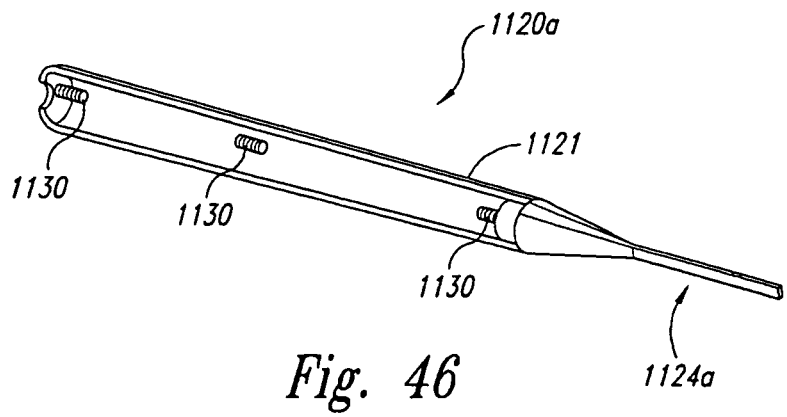
FIGS. 46-52 are isometric views illustrating several instruments in accordance with various embodiments of the invention.
Figure 47:
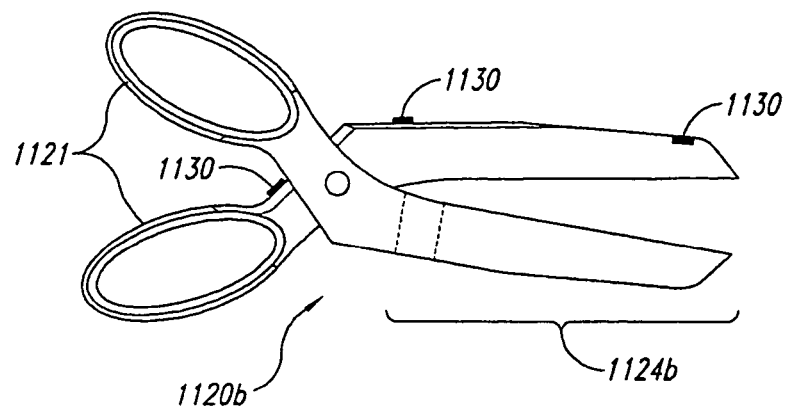
Figure 48:
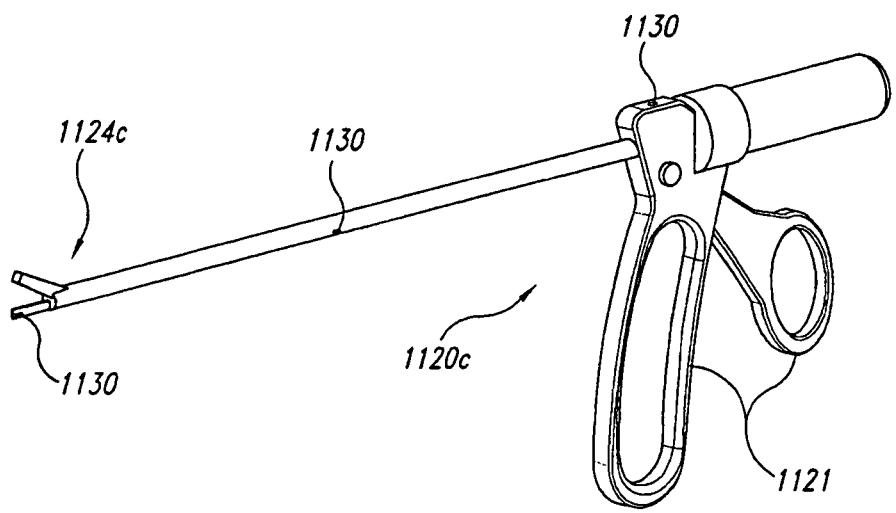
Figure 49:
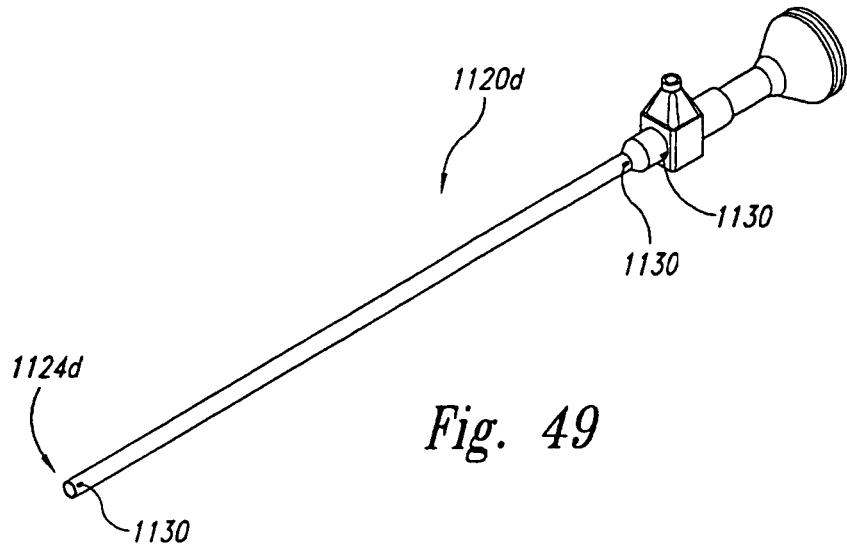
Figure 50:
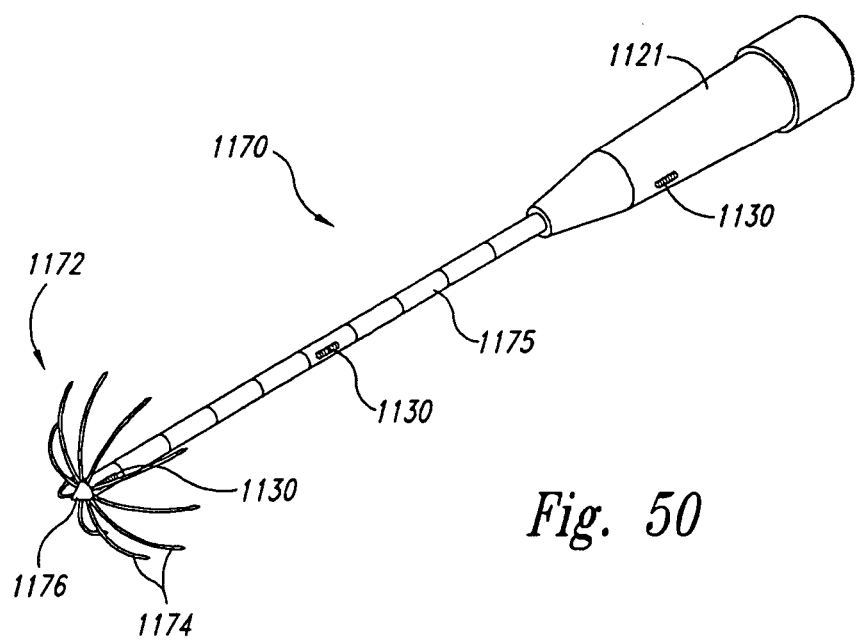
Figure 51:
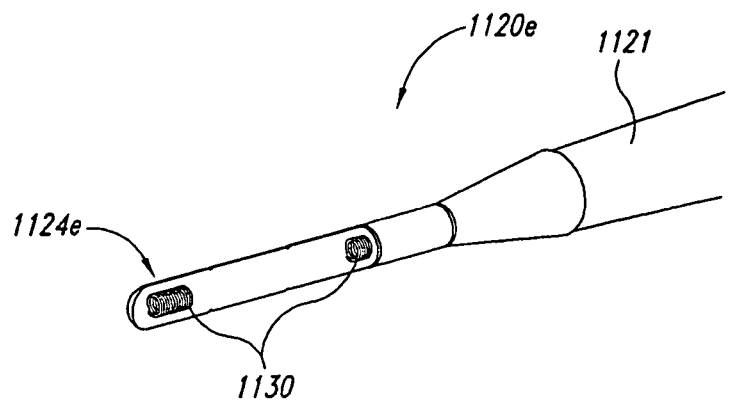
Figure 52:
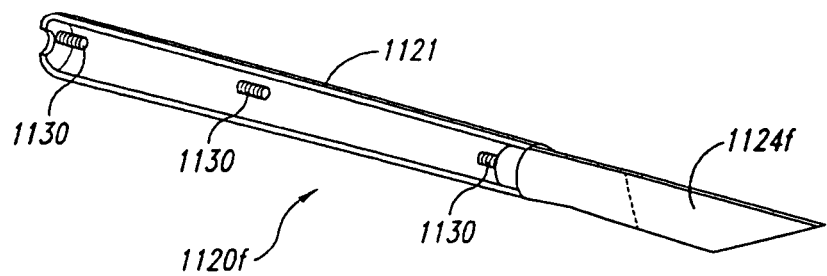

FIG. 46 illustrates a smart Bovie 1124a that has a function-site 1124a defined by an RF cutting blade. Suitable RF cutting devices without the instrument markers 1130 are available from Valley Lab of Boulder, Colo., under the part number E2516 Reusable Electrosurgical Pencil. FIG. 47 illustrates a scissors 1120b that has a function-site 1124b defined by the cutting blades. FIG. 48 illustrates a harmonic scalpel 1120c having a function-site 1124c defined by a harmonic cutting tip. Suitable harmonic scalpels without the instrument markers 1130 are available from Ethicon Endo Surgery of Cincinnati, Ohio, under the part name ULTRACISION HARMONIC SCALPEL®. FIG. 49 illustrates a laproscope 1120d having a function-site 1124d defined by a distal end of the laproscope. Suitable laproscopes without the instrument markers 1130 are available from US Surgical of Norwalk, Conn., under the part name SURGIVIEW® Multi-Use Disposable Laproscope. FIG. 50 illustrates an RF ablation device 1120e having a function-site 1124e with RF elements 1137 through which RF energy is delivered to the target site T. The RF elements 1137 can be retractable into a cannula in a manner similar to the tissue anchors 310 described above with reference to FIGS. 10 and 11. Suitable RF ablation devices 1120e without the instrument markers 1130 are available from Radio Therapeutics Sunnyvale, Calif., under the part name LeVeen Needle Electrodes. FIG. 51 illustrates a robotic probe 1120f having a function-site 1124f defined by a distal tip of the probe 1120f. The probe 1120f can be used to mark reference fiducials just prior to a surgical procedure to map out a desired cutting path. FIG. 52 illustrates a scalpel 1120g having a function-site 1124g defined by a cutting blade. Suitable scalpels without instrument markers 1130 are available from Bard-Parker of Franklin Lake, N.J., such as single-use Scalpel No. 11. It will be appreciated that FIGS. 46-52 illustrate only a few of the types of instruments for use with the system 1000 (FIG. 21), and that other types of instruments can be used with the system 1000 by adding instrument markers 1130 that the position detection system 1200 can track.

D. Embodiments of User Interfaces

FIGS. 53-61 illustrate several embodiments of user interfaces 1300 and methods for using the systems 20 and 1000 in accordance with the invention. The user interfaces 1300 can be used with any of the implantable markers 30 and 1100, and any of the instruments 200, 300 and 1120 described above with reference to FIGS. 1-52. The user interface 1300 is generally a computer display for graphically illustrating or otherwise presenting the position data generated by the position detection system 1200 to a user. The user interface 1300 can alternatively be an audio signal, a visual pattern based on light and/or color, a tactile or mechanical signal (e.g., vibrational), or other indicators that can inform a physician of the relative position between the instrument and the target location.

Figure 53:
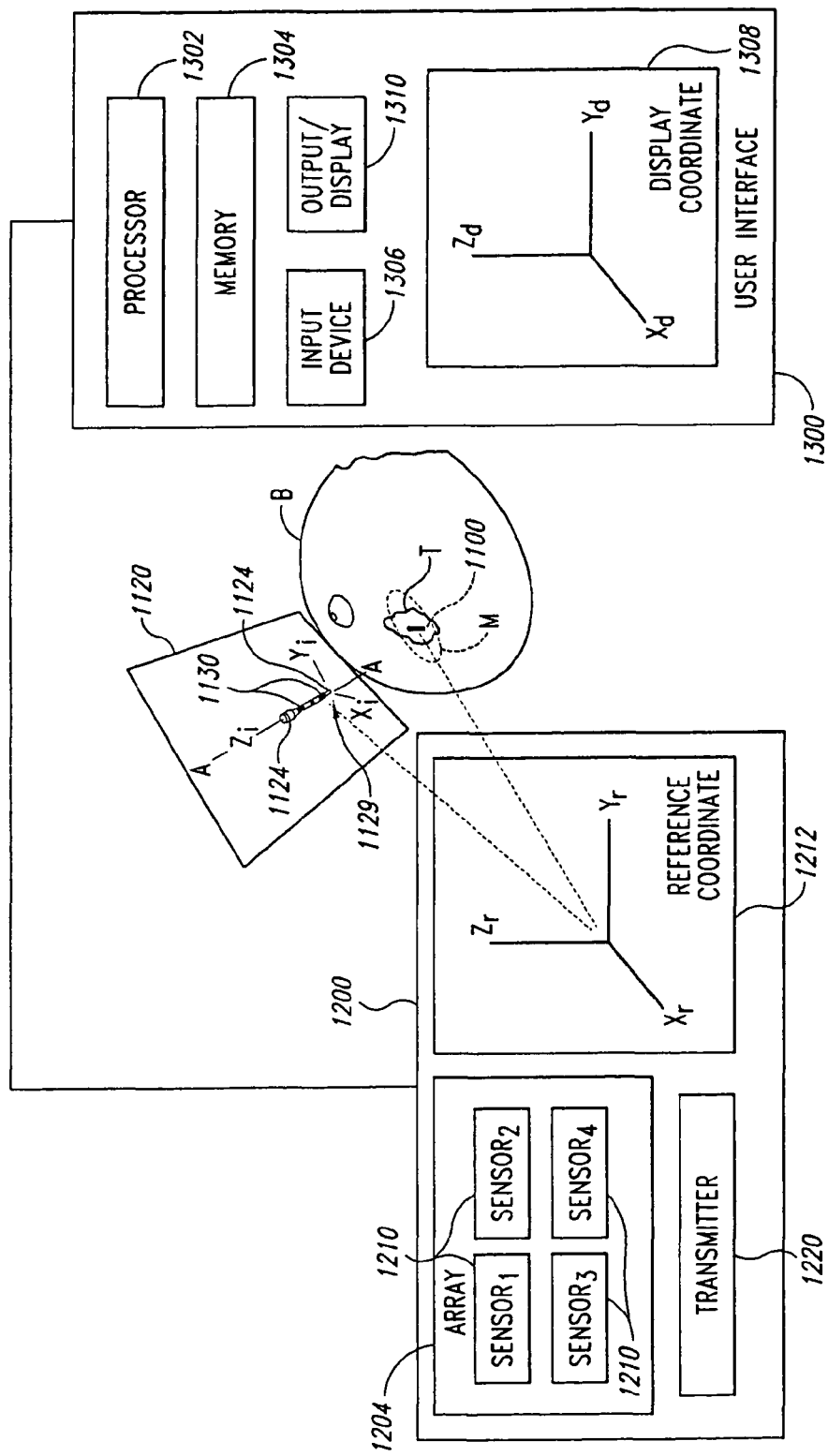
FIG. 53 is a partially schematic view illustrating an aspect of operating a system for locating and defining a target location within a human body in accordance with an embodiment of the invention.

FIG. 53 is a schematic diagram illustrating an embodiment of the system 1000 for displaying the relative position between an instrument 1120 and the target location T. In this embodiment, the system 1000 includes an implantable marker 1100 implanted in the body part B, an instrument 1120 for performing a procedure on the target location T, the position detection system 1200, and the user interface 1300. The implantable marker 1100 and the instrument 1120 can be any one of the embodiments of these devices described above. The instrument 1120, more specifically, has an instrument coordinate system 1129 defined by the orthogonal axes $X_i$-$Y_i$-$Z_i$. The $Z_i$-axis is aligned with the alignment axis A-A, and the $X_i$-axis and $Y_i$-axis define an operating plane normal to the $Z_i$-axis. The instrument coordinate system 1129 moves with the instrument during the procedure. The position detection system 1200 generally includes the same components described above with reference to FIGS. 21 and 22. As such, the position detection system 1200 can include an array 1204 having sensors 1210 and a transmitter 1220 for emitting an excitation energy that drives the implanted marker 1100 and the instrument markers 1130. The position detection system 1200 can also include a reference coordinate system 1212 defined by three orthogonal axes $X_r$-$Y_r$-$Z_r$. In operation, the position detection system 1200 determines the position of the implanted marker 1100 and the positions of the instrument markers 1130 relative to the reference coordinate system 1212 to determine the relative position between the function-site 1124 of the instrument 1120 and the target location T. The position detection system 1200 can also include a processor.

The user interface 1300 provides a display or another type of indicator of the relative position between the function-site 1124 and the target location T based on data from the position detection system 1200. In this embodiment, the user interface 1300 includes a processor 1302, a memory 1304 coupled to the processor 1302, an input device 1306 for controlling parameters of the system 1000, and an output display 1310. The processor 1302 and the memory 1304 can be a computer available from many sources. The input device 1306 can be a keyboard, a computer mouse, a touch screen, or any other suitable device for inputting commands to the processor 1302. The output display 1310 is preferably a display screen, but it can also be another type of output device that generates an output that can be detected and understood by a user. The user interface 1300 also includes a display coordinate system 1308 defined by three orthogonal axes $X_d$-$Y_d$-$Z_d$. The display coordinate system 1308 can initially correspond to the reference coordinate system 1212 of the position detection system 1200. In many applications, however, it may not be desirable to view the display 1310 based upon the reference coordinate system 1212. The processor 1302 can accordingly calibrate the display coordinate system 1308 so that the display 1310 shows a desired two-dimensional plane or a desired three-dimensional space.

In operation, the user interface 1300 processes data from the position detection system 1200 in real-time to show the relative motion between the function-site 1124 and the target location T. For example, the processor 1302 receives signals from the position detection system 1200 and produces output signals that can be represented by the output display 1310. As explained in more detail below, the user can set the parameters for generating the virtual margin 1301 and controlling other aspects of the user interface 1300 using the input device 1306.

FIG. 53 also illustrates an orientation between the instrument 1120 and the target location T that generally corresponds to a calibrating stage of a procedure for treating, probing, or monitoring the target location T. The surgeon typically holds the instrument 1120 so that the alignment axis A-A of the instrument 1120 defines a desired $Z_i$ elevation axis along which the surgeon moves the instrument 1120 up and down relative to the target location T. The $X_i$-$Y_i$ plane normal to the $Z_i$-axis defines the desired operating plane in which the surgeon moves the instrument 1120 along a margin M around the target location T during a procedure. When the physician holds the instrument 1120 relative to the target location T in a desired orientation for performing the procedure, the instrument coordinate system 1129 ($X_i$-$Y_i$-$Z_i$) may not be aligned with the reference coordinate system 1212 ($X_r$-$Y_r$-$Z_r$) and the display coordinate system 1308 ($X_d$-$Y_d$-$Z_d$). The user interface 1300 accordingly calibrates the display coordinate system 1308 to coincide with the instrument coordinate system 1129 so that the user interface 1300 indicates movement of instrument 1120 (a) along the alignment axis A-A as an elevation relative to the target location T, and (b) through the operating plane $X_i$-$Y_i$ as a location in an X-Y grid of the display 1310.

Figure 54A:
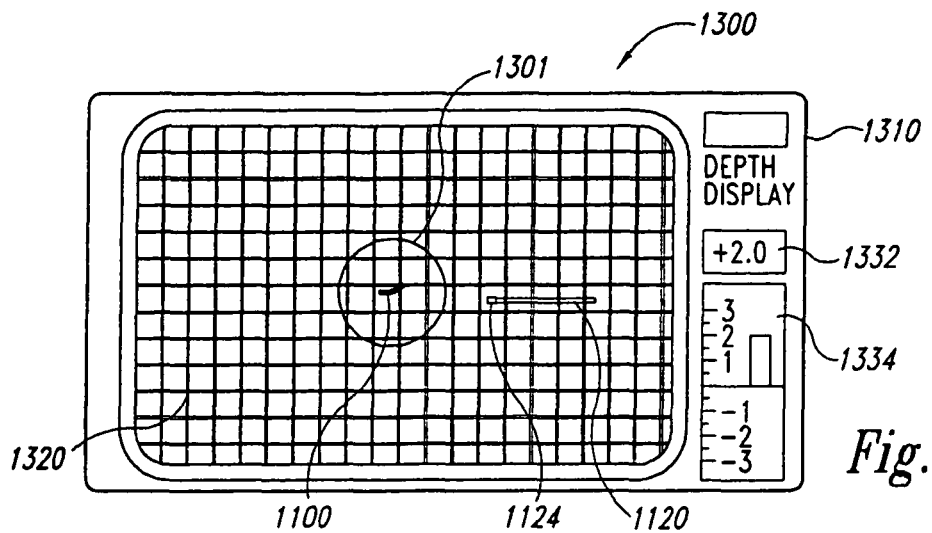
FIG. 54A is a front elevation view of an embodiment of a user interface in accordance with the invention.

FIG. 54A illustrates one embodiment of the user interface 1300 showing the relative position between the instrument 1120 and the target location T before calibrating the position detection system 1200 to align the display coordinate system 1308 (FIG. 53) with the instrument coordinate system 1129 (FIG. 53). In this embodiment, the display 1310 has a two-dimensional grid 1320 that shows the $X_d$-$Y_d$ plane of the display coordinate system 1308. The display 1310 can also include a numerical elevation indicator 1332 and/or a graphical elevation indicator 1334. The elevation indicators 1132 and 1134 show the position along the $Z_d$-axis of the display coordinate system 1308. The instrument 1120 is displayed as a line on the grid 1320 because the user interface 1300 has not yet been calibrated to align the display coordinate system 1308 with the instrument coordinate system 1129. The function-site 1124 of the instrument 1120 appears as a point at one end of instrument 1120, and the elevation of the function-site 1124 relative to the target location T is displayed by one or both of the elevation indicators 1332 and 1334. At this stage before calibrating the user interface 1300, it may be difficult for a physician to determine the relative position between the function-site 1124 and the target location T because moving the instrument 1120 along the alignment axis A-A simultaneously changes the position of the function-site 1124 on the grid 1320 and on the elevation indicators 1332 and 1334. Therefore, to provide a more intuitive display of the motion of the instrument 1120, the position detection system 1200 aligns the display coordinate system 1308 with the instrument coordinate system 1129.

Figure 54B:
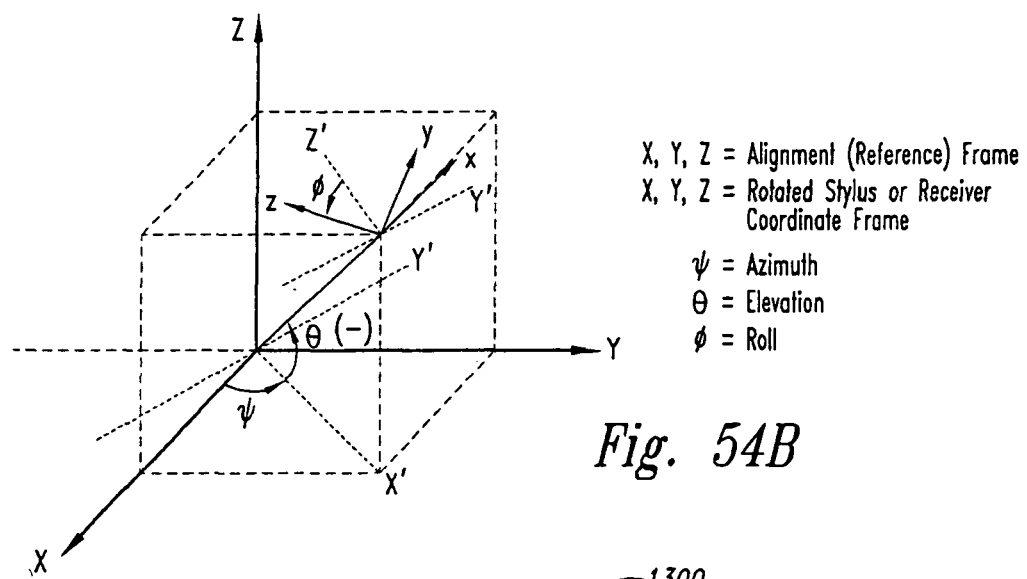
FIG. 54B is a graphical representation of calibrating a display coordinate system.

Referring to FIG. 54B, an example of an algorithm for performing the calibration transformation is described as follows. The definitions include Azimuth=$\psi$; Elevation=$\theta$; Point before transformation=(a,b,c). The mathematical equation to convert this point into the X',Y',Z' coordinate system; (a',b', c'). In the user interface, the marker would be at (0,0,0) after the implementation of the algorithms. The X, Y, Z axis would still be oriented with the original coordinate system of the system reference. First rotate about the z-axis by the azimuth angle or $\psi$. The point in this intermediary coordinate system is now defined as:

$$p = a^*\cos(\psi) + b^*\sin(\psi)$$

$$q = b^*\cos(\psi) - a^*\sin(\psi)$$

$$r = c$$

Next, rotate about the y-axis so that the z-axis is in line with the probe. Effectively rotation will be about the y-axis by the elevation angle −90° or ($\theta$−90°). The point in the X',Y',Z' coordinate system would now be defined as:

$$a' = p^*\sin(\theta) - r^*\cos(\theta)$$

$$b' = q$$

$$c' = p^*\cos(\theta) + r^*\sin(\theta)$$

Substituting the values of p, q, and r into these equations the following equation is obtained in terms of the original coordinates and the azimuth and elevation angles:

$$a' = [a^*\cos(\psi) + b^*\sin(\psi)]^*\sin(\theta) - c^*\cos(\theta)$$

$$b' = b^*\cos(\psi) - a^*\sin(\psi)$$

$$c' = [a^*\cos(\psi) + b^*\sin(\psi)]^*\cos(\theta) + c^*\sin(\theta)$$

The point (a',b',c') represents the original point (a,b,c) transformed into the new coordinate system. The user interface display probe tip projection math length projection on X-Y display plane is defined by the equation:

Display Length=length probe tip*cosine(Elevation angle)

Based on these algorithms, a person skilled in the art can program the user interface 1300 to perform the calibration without undue experimentation.

Figure 55:
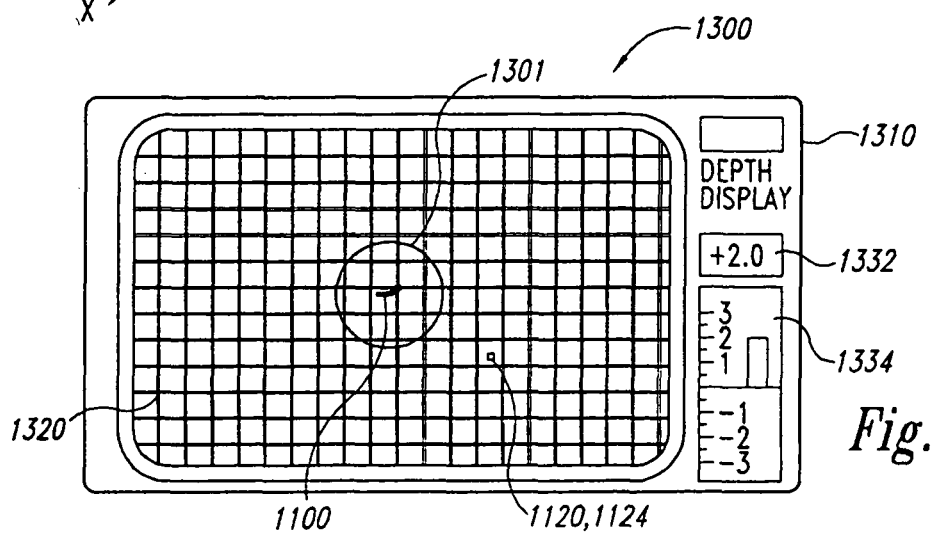
FIGS. 55-57 are front elevation views of several embodiments of user interfaces in accordance with various embodiments of the invention.

FIG. 55 illustrates an embodiment of the user interface 1300 of FIG. 54 after the position detection system 1200 calibrates the user interface 1300 to align the display coordinate system 1308 with the instrument coordinate system 1129. In this embodiment, the instrument 1120 and the function-site 1124 are both displayed as a point location on the grid 1320. The elevation of the function-site 1124 relative to the target location T still appears as a numeric or graphical readout on the elevation indicators 1332 and 1334. After calibrating the coordinate systems, the user interface 1300 accordingly shows (a) movement of the instrument 1120 solely along the alignment axis A-A by changing only the readout on the elevation indicators 1332 and 1334 without changing the location of the instrument 1120 on the grid 1320, and (b) movement of the instrument 1120 solely through the operating plane $X_i$-$Y_i$ by changing only the location of the instrument 1120 on the grid 1320 without changing the readout on the elevation indicators 1332 and 1334. The position detection system 1200 and/or the user interface 1300 can alternatively continuously calibrate the system 1000 so that the display coordinate system 1308 continuously coincides with the instrument coordinate system 1129. In such an embodiment, the grid 1320 is continuously normal to the alignment axis A-A of the instrument 1120 such that the display 1310 continuously displays the instrument 1120 as a point location (as shown in FIG. 55) irrespective of the orientation of the instrument 1120.

FIGS. 54A and 55 also illustrate one embodiment for defining a virtual margin 1301 relative to the target location T for use on the display 1310 of the user interface 1300. As described above with reference to FIGS. 34-39, the virtual margin 1301 can be generated based upon the position of an implantable marker 1100 or a plurality of implantable markers 1100. The virtual margin 1301 is generally defined by a physician based upon information from an imaging procedure, such as when the markers 1100 are implanted. The virtual margin 1301 can be configured to include a lesion, tumor, or other mass that defines the area of interest at the target location T. The virtual margin 1301 should be configured to avoid removing or otherwise performing a procedure on material outside of the virtual margin 1301. As such, after determining the relative position between the implantable marker 1100 and the target location T using an imaging process (e.g., radiation, MRI, ultrasound, etc.), the physician determines the desired virtual margin 1301 to input into the user interface 1300.

The physician can input the desired virtual margin 1301 into the user interface 1300 using the input device 1306 of the user interface 1300 or an instrument 1120 (e.g., the probe 1120f shown in FIG. 51). In one embodiment using a keyboard, the physician can enter a desired radius relative to the target location T to define a spherical or cylindrical virtual margin 1301 that is displayed as a circle on the grid 1320 of the display 1310. As explained above, the virtual margin 1301 can also be configured to be rectilinear, a compound shape, or any other suitable two-dimensional or three-dimensional shape that is defined by the physician. The user interface 1300 accordingly displays the selected a virtual margin 1301 to define a boundary relative to the target location T. For example, the virtual margin 1310 is often configured to completely surround or encompass a tissue mass or other body part within the target location T. Referring still to FIGS. 54 and 55, this embodiment of the invention illustrates a single implantable marker 1100 disposed in the target location T and a spherical or cylindrical virtual margin 1301 around the implantable marker 1100.

Figure 56:
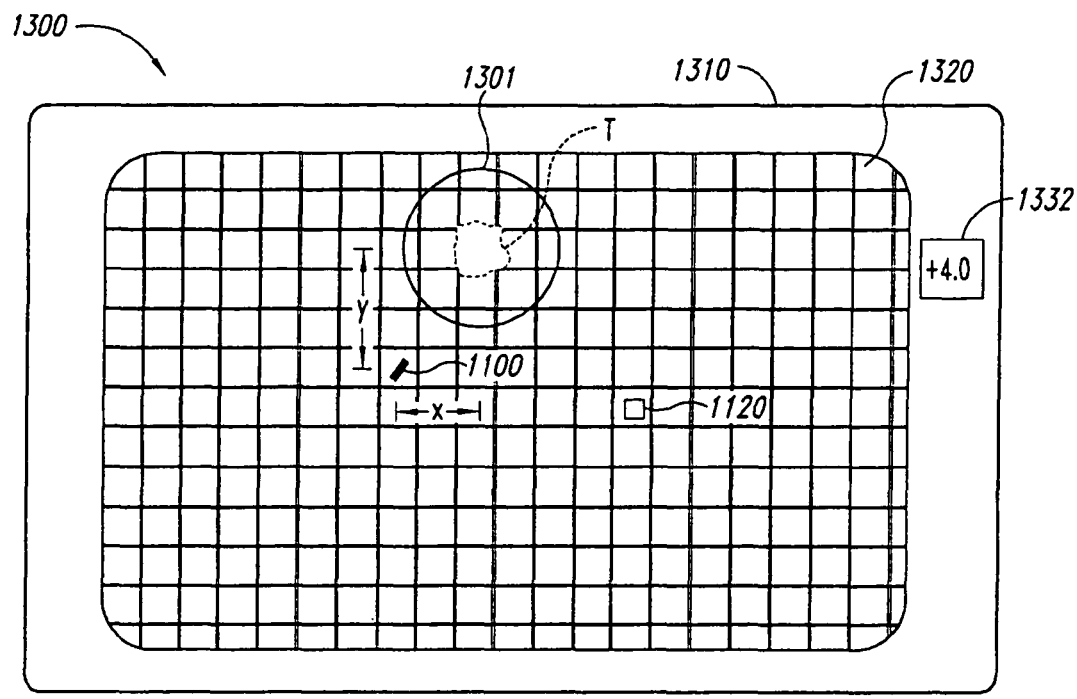

FIG. 56 illustrates another embodiment for defining a virtual margin 1301 relative to a target location T. In this embodiment, the user interface 1300 can display an outline of the target location T (shown in broken lines), but it will be appreciated that the target location T may not be displayed on the grid 1320. This embodiment of the invention illustrates a single implantable marker 1100 disposed outside of the target location T by an offset distance having coordinate differentials of "X" along an X-axis of the grid 1320, "Y" along the Y-axis of the grid 1320, and "Z" (not shown) along an axis normal to a plane defined by the grid 1320. The offset distance can be determined during a previous imaging procedure or when the implantable marker 1100 is implanted using known radiation, MRI, ultrasound and other imaging techniques. Based upon the position of the implantable marker 1100 and the offset distance between the implantable marker 1100 and the target location T, the user interface 1300 can generate the virtual margin 1301 around the actual location of the target location T. One advantage of implanting the marker 1100 outside of the target location T is that the implantable marker 1100 does not pierce the tissue mass or other body part of the target location T. This feature can be particularly useful in applications for removing cancerous tissue masses or other types of tissue/bone masses that are desirably left intact until they are removed from the patient.

Figure 57:
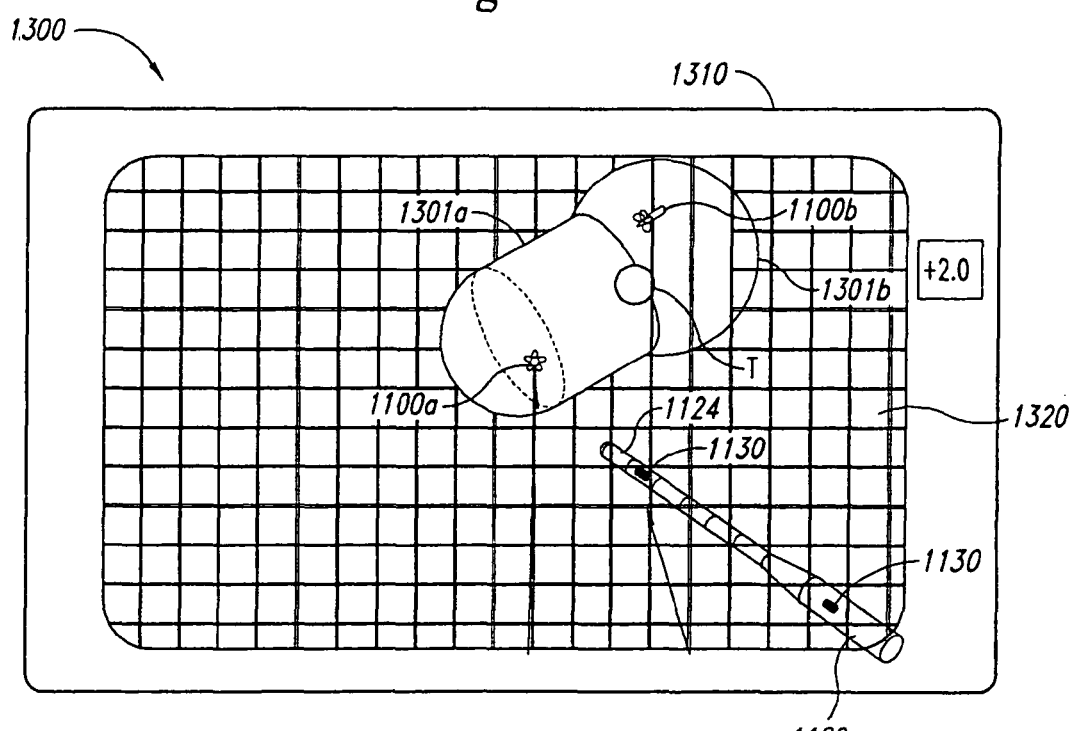

FIG. 57 illustrates another embodiment for defining a virtual margin 1301 relative to the target location T. In this embodiment, two implantable markers 1100a and 1100b have been implanted at two separate offset distances relative to the target location T. The physician can input two separate virtual margins 1301a and 1301b relative to the individual implantable markers 1100a and 1100b, respectively. In this particular embodiment, the virtual margin 1301a is relative to the first implantable marker 1100a and defines a cylindrical boundary. Similarly, the virtual margin 1301b is relative to the second implantable marker 1100b, but it defines a spherical boundary. The virtual margins 1301a and 1301b together define a compound virtual margin relative to the target location T. It will be appreciated that several other virtual margins can be developed using different combinations of one or more implantable markers, and different combinations of markers that are implanted in and/or offset from the target location T. In any of the embodiments of the virtual margins 1301 described above, the physician can manipulate an instrument 1120 relative to the target location T using the user interface 1300 to display the relative position between the function-site 1124 of the instrument 1120 relative to the virtual margin 1301.

Figure 58A:
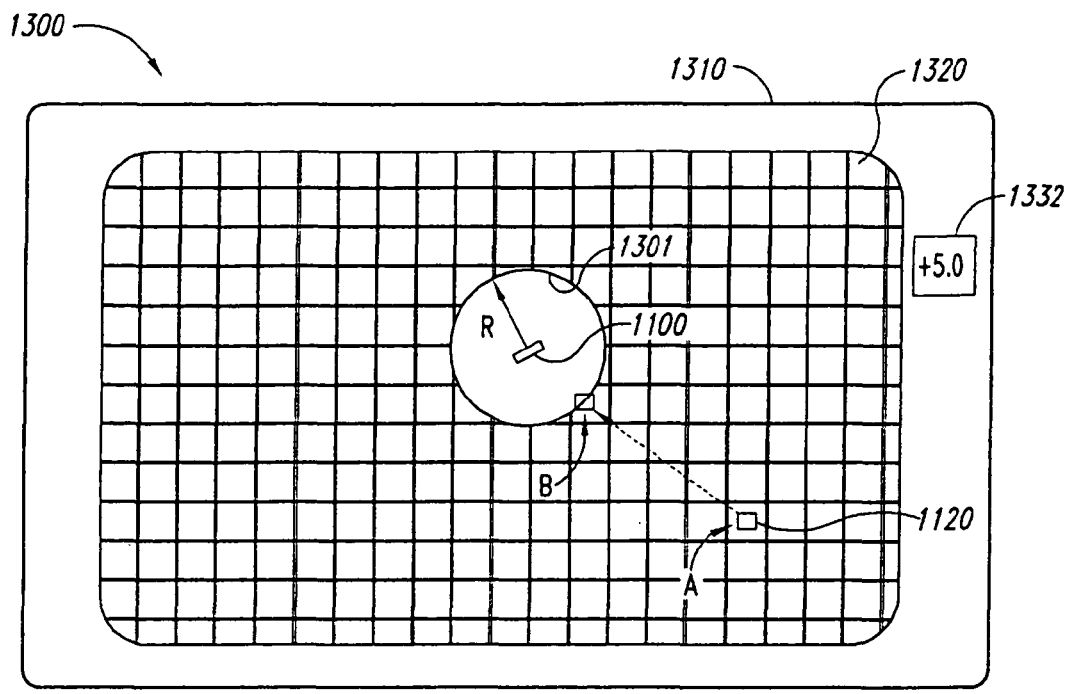
FIGS. 58A-58C are front elevation views of an embodiment of a user interface illustrating a method of operating the system in accordance with an embodiment of the invention.
Figure 58B:
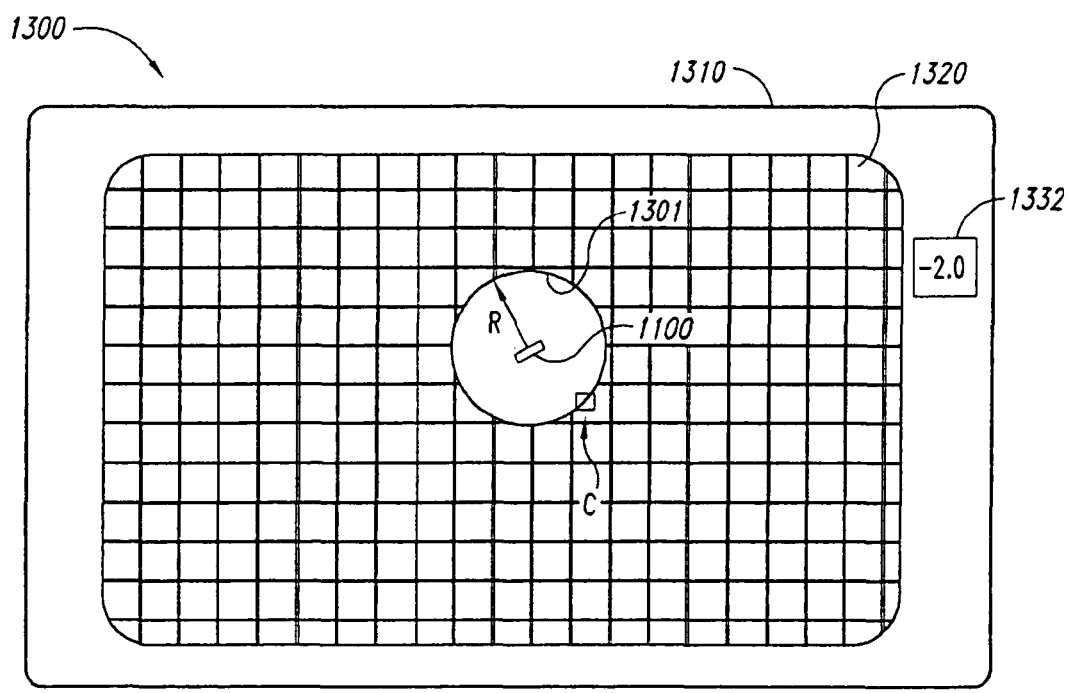
Figure 58C:
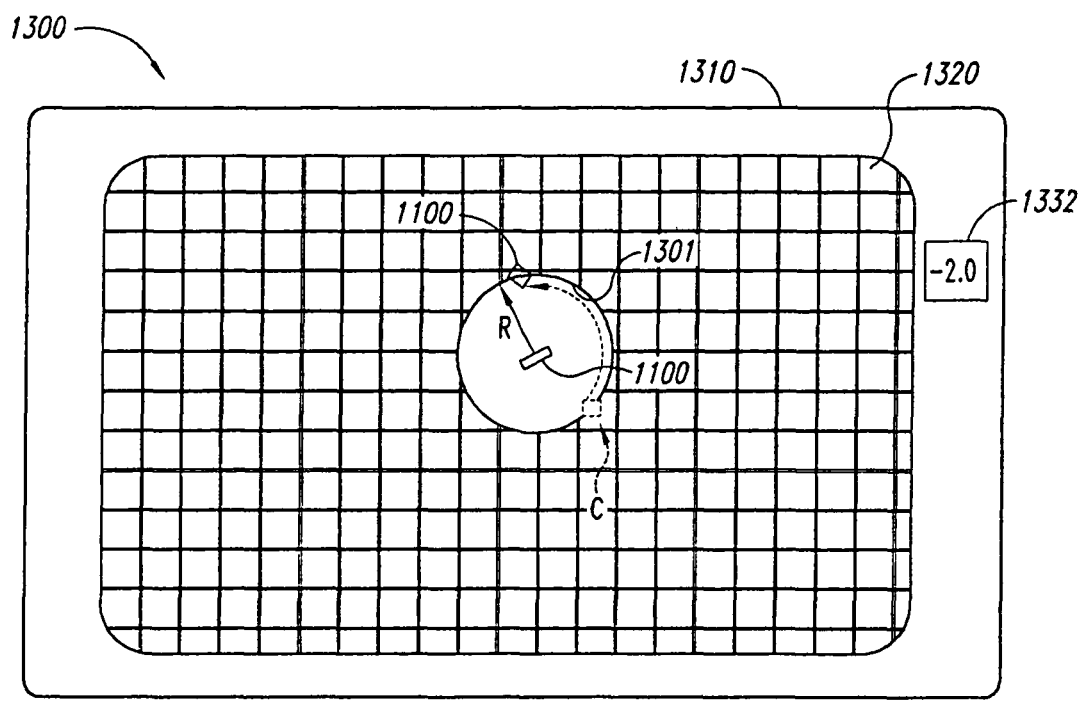

FIGS. 58A-58C illustrate a procedure for operating the system 1000 in accordance with one embodiment of the invention. In this example, a single implantable marker 1100 has been implanted within the target location T and the user interface 1300 has generated a cylindrical or spherical virtual margin 1301 around the target location T. Referring to FIG. 58A, the instrument 1120 is shown after the display coordinate system has been calibrated to be aligned with the instrument coordinate system in the manner explained above with reference to FIGS. 53-55. The user interface 1300 initially displays the instrument 1120 as a point at a location A. Based upon this display, the physician understands that the alignment axis A-A of the instrument 1120 is normal to the grid 1320 of the display 1310, and that the function-site 1124 of the instrument 1120 is at an elevation of 5 cm above a predetermined reference plane relative to the target location T and/or the implanted marker 1100 (see the elevation indicator 1332). The physician then moves the instrument 1120 transverse relative to the alignment axis A-A to a location B on the virtual margin 1301. In this particular embodiment, the physician held the instrument 1120 at a constant elevation of 5 cm above the reference plane shown by the elevation indicator 1132.

FIG. 58B illustrates a subsequent stage of operating the system 1000. After moving the instrument 1120 from location A to location B (FIG. 58A), the physician inserts the function-site 1124 of instrument 1120 into the body part to move the function-site 1124 from the location B to a location C. Referring to both FIGS. 58A and 58B, the elevation indicator 1132 shows that the elevation of the function-site 1124 relative to the reference plane has moved from 5 cm above the reference plane to 2 cm below the reference plane. In an application in which the physician wants to excise a cylindrical tissue mass having a base 2 cm below the reference plane, the instrument 1120 at location C is accordingly ready to be moved along the virtual margin 1301 to excise a mass of tissue. Referring to FIG. 58C, the user interface 1300 displays the motion of the instrument as the physician or robot moves it along the virtual margin 1301. The virtual margin 1301 accordingly provides a guide to the physician that allows the physician to excise a precise volume of tissue without cutting into the target mass or damaging tissue outside of the target location T.

Figure 59:
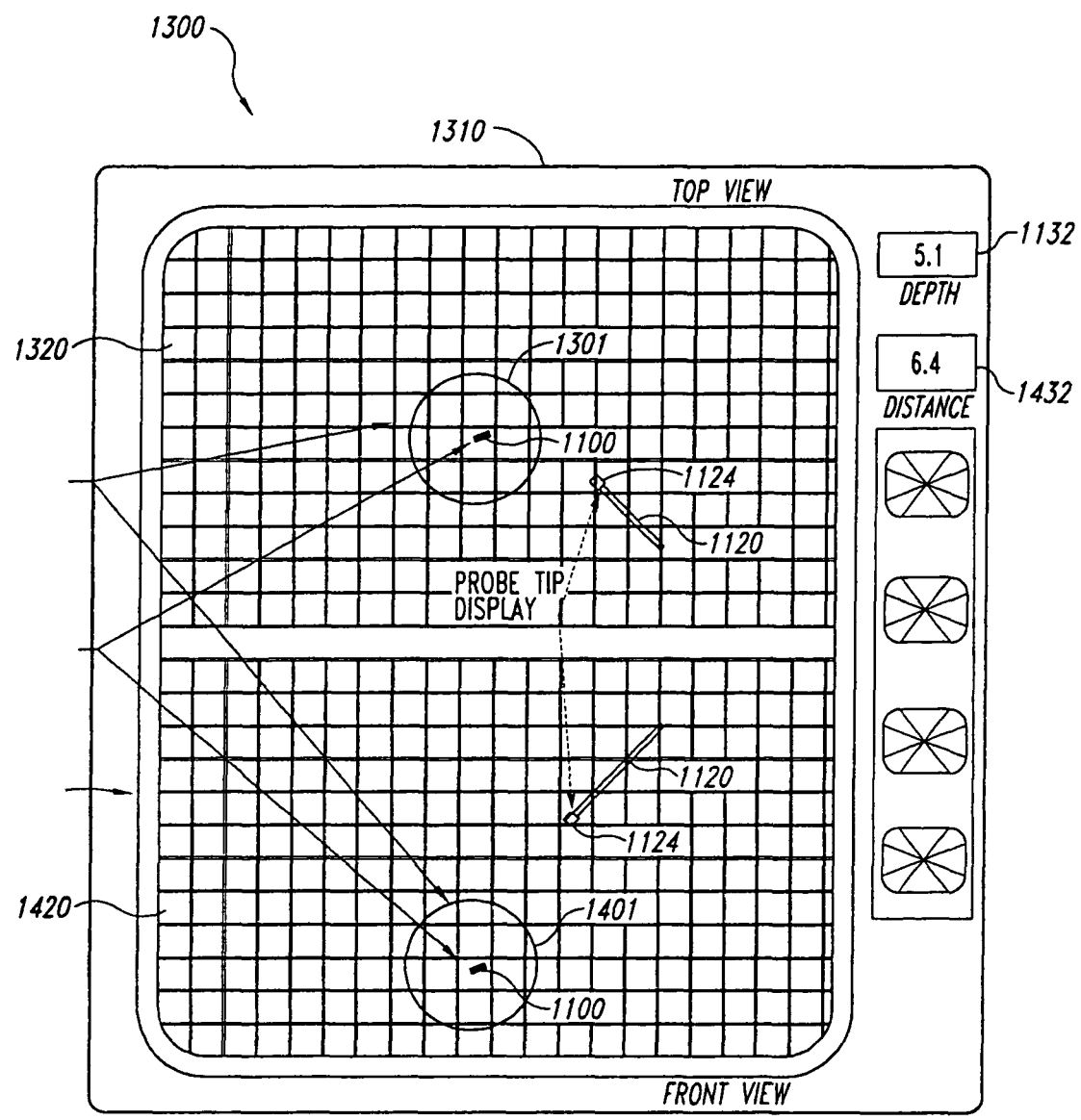
FIGS. 59-61 are front elevation views of several additional user interfaces in accordance with more embodiments of the invention.

FIG. 59 illustrates another embodiment of the user interface 1300 in accordance with the invention. In this embodiment, the display 1310 includes a first grid 1320 illustrating a top view relative to a reference plane and a second grid 1420 illustrating a front view normal to the reference plane. For purposes of convention, the reference plane can be parallel to the table on which the patient is positioned during a procedure, but it can also be at an angle to the table. The display 1310 can also include an elevation indicator 1132 showing the elevation of the function-site 1124 relative to the target location T and a distance indicator 1432 showing the point-to-point distance between the function-site 1124 and the target location T. The embodiment of the display 1310 shown in FIG. 59 provides the physician two separate views that the physician can use to more accurately position the function-site 1124 relative to the target location T. The operation and the advantages of the display 1310 illustrated in FIG. 59 are expected to be similar to those described above with reference to FIGS. 55-57.

Figure 60:
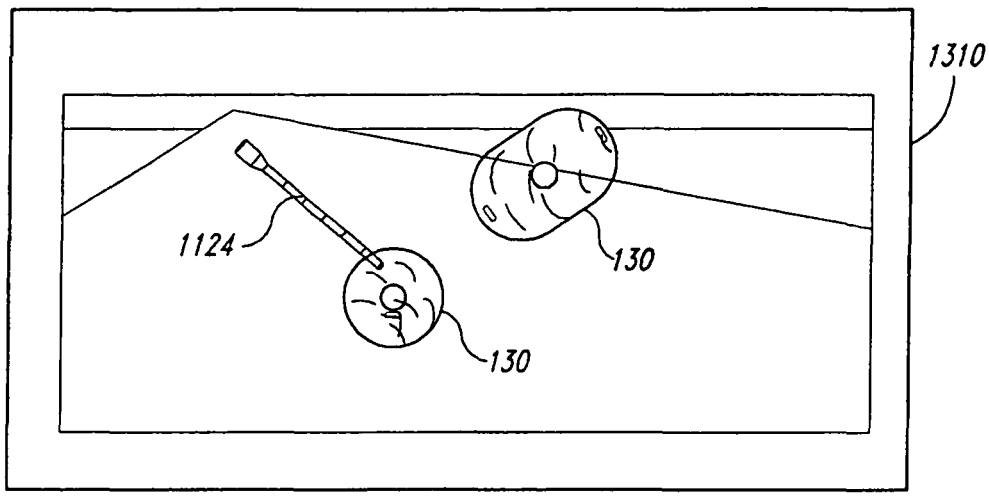
Figure 61:
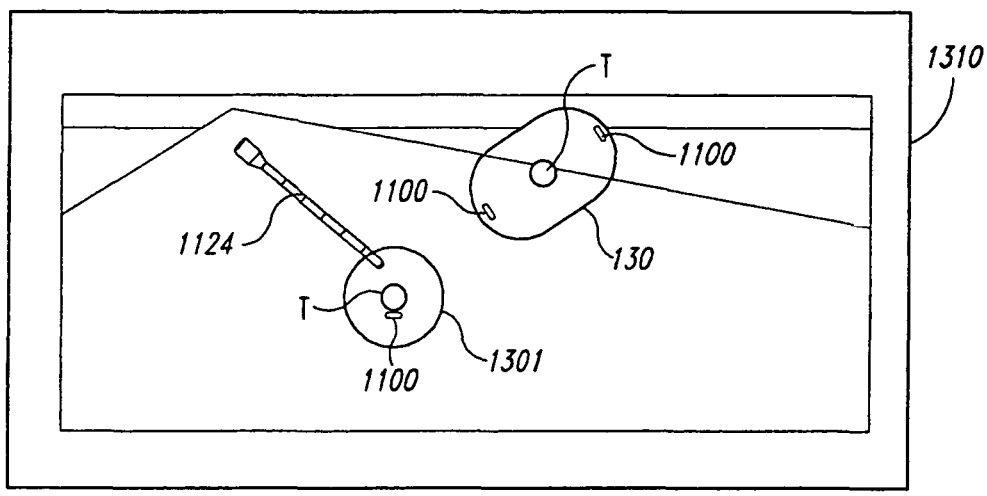

FIGS. 60 and 61 illustrate additional embodiments of the user interface 1300 in accordance with the invention. Referring to FIG. 60, the display 1310 provides a three-dimensional solid or opaque representation of the virtual margin 1301. FIG. 61 illustrates an embodiment in which the display 1310 provides a holographic representation of the virtual margin 1301 such that the target location T can be represented within the holographic representation. Suitable software for generating the three-dimensional representations of the virtual margin 1301 illustrated in FIGS. 60 and 61 is available from Medical Media System of West Lebanon, N.H. The three-dimensional representations of the virtual margin 1301 also provide a physician with an intuitive understanding of the relative position between the function-site 1124 of the instrument 1120 and the virtual margin 1301 relative to the target location T. It is expected, therefore, that the three-dimensional virtual margins 1301 will also allow physicians to accurately perform procedures or monitor internal target locations within a human body without additional imaging equipment or procedures.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

What is claimed is:

1. A wireless marker for use in localizing a target of a patient, comprising:
   a magnetic signal element including a core and a coil around the core, wherein the signal element produces a wireless resonating signal at a predetermined resonant frequency in response to a wireless excitation energy wherein the resonating signal response is used to localize the signal element;
   a biocompatible casing housing the signal element and being configured to be implanted in the patient relative to the target, wherein the casing includes a cylindrical section with a diameter of 1-2 mm; and
   an external fastener configured to hold the marker at a reference location relative to the target.

2. The marker of claim 1 wherein the signal element further comprises a capacitor electrically coupled to the coil.

3. The marker of claim 1 wherein the fastener comprises a protrusion integral with the casing.

4. The marker of claim 1 wherein the fastener comprises a biasing member that expands from a stored position to a deployed position.

5. The marker of claim 1 wherein the fastener comprises a biasing member that contracts from a stored position to a deployed position.

6. The marker of claim 1 wherein the fastener comprises a spring that forms a loop configured to grasp tissue in a deployed position.

7. The marker of claim 1, further comprising an identifier on and/or in the casing that can be observed by an imaging system to distinguish the casing from other items in the patient.

8. The marker of claim 7 wherein the identifier comprises metal bands.

9. A wireless marker for use in localizing a target of a patient, comprising:
   a signal element including a core and a coil configured to produce a wireless resonating signal at a predetermined resonant frequency in response to a wireless excitation energy wherein the resonating signal response is used to localize the signal element; and
   a biocompatible casing housing the signal element and being configured to be implanted in the patient relative to the target, the casing providing a fastener to hold the marker at a reference location relative to the target, wherein the casing includes a cylindrical section with a diameter of 1-2 mm.

10. The wireless marker of claim 9 wherein the signal element comprises a magnetic resonator.

11. The wireless marker of claim 10 wherein the magnetic resonator comprises a core, a coil around the core, and a capacitor electrically coupled to the coil.

12. The marker of claim 9 wherein the fastener comprises a protrusion integral with the casing.

13. The marker of claim 9 wherein the fastener comprises a biasing member that expands from a stored position to a deployed position.

14. The marker of claim 9 wherein the fastener comprises a biasing member that contracts from a stored position to a deployed position.

15. The marker of claim 9 wherein the fastener comprises a spring that forms a loop configured to grasp tissue in a deployed position.

16. The marker of claim 9, further comprising an identifier on and/or in the casing that can be observed by an imaging system to distinguish the casing from other items in the patient.

17. The marker of claim 16 wherein the identifier comprises metal bands.

18. A plurality of wireless markers for use in localizing a target of a patient, each of the plurality of wireless markers comprising:
   a magnetic signal element including a core and a coil around the core, wherein the signal element produces a wireless resonating signal in response to a wireless excitation energy wherein the resonating signal response is used to localize the signal element, and wherein a first marker of the plurality of wireless markers produces a wireless resonating signal at a first predetermined frequency and a second marker of the plurality of wireless markers produces a wireless resonating signal at a second predetermined frequency, wherein the first frequency is different from the second frequency; and
   a biocompatible casing housing the signal element and being configured to be implanted in the patient relative to the target the casing providing a fastener to hold the marker at a reference location relative to the target, wherein the casing includes a cylindrical section with a diameter of 1-2 mm.

19. A wireless marker for use in localizing a target of a patient, comprising:
   a magnetic signal element including a core and a coil around the core, wherein the signal element produces a wireless resonating signal in response to a wireless excitation energy wherein the resonating signal response is a known resonant frequency and used to localize the signal element; and
   a biocompatible casing housing the signal element and being configured to be implanted in the patient relative to the target the casing including a fastener—configured to hold the marker at a reference location relative to the target, wherein the casing includes a cylindrical section with a diameter of 1-2 mm.

* * * * *